(12) United States Patent
Cardone et al.

(10) Patent No.: US 9,345,700 B2
(45) Date of Patent: *May 24, 2016

(54) COMPOSITIONS AND METHODS USEFUL FOR TREATING DISEASES

(71) Applicant: Eutropics Pharmaceuticals, Inc., Cambridge, MA (US)

(72) Inventors: Michael H. Cardone, Dorchester, MA (US); Andrew F. Kolodziej, Winchester, MA (US); David Richard, Littleton, MA (US)

(73) Assignee: Eutropics Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,875

(22) Filed: Apr. 30, 2015

(65) Prior Publication Data

US 2015/0352097 A1 Dec. 10, 2015

Related U.S. Application Data

(62) Division of application No. 14/003,733, filed as application No. PCT/US2012/028263 on Mar. 8, 2012, now Pat. No. 9,051,305.

(60) Provisional application No. 61/450,369, filed on Mar. 8, 2011.

(51) Int. Cl.
*A61K 31/4709* (2006.01)
*A61K 31/496* (2006.01)
*C07D 405/14* (2006.01)
*C07D 417/14* (2006.01)
*C07D 401/14* (2006.01)

(52) U.S. Cl.
CPC ............ *A61K 31/4709* (2013.01); *A61K 31/496* (2013.01); *C07D 401/14* (2013.01); *C07D 405/14* (2013.01); *C07D 417/14* (2013.01)

(58) Field of Classification Search
CPC ............. A61K 31/4709; A61K 31/496; C07D 405/14; C07D 417/14; C07D 401/14
See application file for complete search history.

(56) References Cited

U.S. PATENT DOCUMENTS

| | | | |
|---|---|---|---|
| 9,051,305 B2 * | 6/2015 | Cardone | C07D 405/14 |
| 2008/0199890 A1 | 8/2008 | Letai | |
| 2008/0300239 A1 | 12/2008 | Adams et al. | |
| 2009/0005416 A1 | 1/2009 | Munchhof et al. | |

FOREIGN PATENT DOCUMENTS

| | | |
|---|---|---|
| WO | WO 2004/080463 A1 | 9/2004 |
| WO | WO 2010/107765 A1 | 9/2010 |

OTHER PUBLICATIONS

Strigacova et al., "Some Biological Properties of New Quinoline-4-carboxylic Acid and Quinoline-4-carboxamide Derivatives," Folia Microbial. 45(4):305-309 (2000).
PubChem CID 49790728, Dec. 15, 2010, <URL:http://pubchem.ncbi.nlm.nihlgov/summary.cgi?cid=49790728.
Supplementary European Search Report, EP appl. No. 12755171.1, 5 pages (Sep. 11, 2014).
Written Opinion of the International Searching Authority, PCT appl. No. PCT/US2012/028263, 6 pages (Oct. 16, 2012).
International Search Report, PCT appl. No. PCT/US2012/028263, 4 pages (Oct. 16, 2012).

* cited by examiner

*Primary Examiner* — D M Seaman
(74) *Attorney, Agent, or Firm* — Cooley LLP; J. Dean Farmer; Fraser D. Brown

(57) ABSTRACT

The present invention relates to a compositions for and methods of cancer treatment in which compounds of Formula I or Formula II. In some aspects, the treatment of B-cell Lymphoma or other hematopoietic cancers is encompassed. In other aspects, the invention provides methods for treating particular types of hematopoietic cancers, such as B-cell lymphoma, using a combination of one or more compounds of Formula I or Formula II. Combination therapy with, for example, a class of therapeutics known as 26S proteasome inhibitors, for example, Bortezomib, are also included. In another aspect the present invention relates to autoimmune treatment with compounds of Formula I or Formula II. In another aspect, this invention relates to methods for identifying compounds, for example, compounds of the BH3 mimic class, that have unique in vitro properties that predict in vivo efficacy against B-cell lymphoma tumors and other cancers as well as autoimmune disease.

19 Claims, 10 Drawing Sheets

FIG. 1A

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 1 | 3.0 | 5 | N/A | 2.4 | 25 |
| 2 | 8.2 | >25 | N/A | N/A | >25 |
| 3 | 8.4 | N/A | N/A | N/A | N/A |
| 4 | 1.9 | N/A | N/A | N/A | N/A |
| 5 | 5.0 | 6.6 | N/A | N/A | 25 |
| 6 | 1.5 | N/A | 7.5 | N/A | 5.6 |
| 7 | 1.6 | N/A | >25 | N/A | >25 |

FIG. 1B

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 8 | 7.7 | 25 | N/A | 7.2 | >25 |
| 9 | 3.7 | 13.3 | N/A | 6.4 | 12.8 |
| 10 | 7.6 | 2.7 | N/A | N/A | 1.5 |
| 11 | 11.3 | >25 | N/A | N/A | >25 |
| 12 | 6.3 | 6.3 | N/A | 6.5 | >25 |
| 13 | 7.2 | N/A | N/A | N/A | N/A |

FIG. 1C

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 14 | 5.1 | N/A | N/A | >25 | >25 |
| 15 | 2.4 | N/A | N/A | N/A | >25 |
| 16 | 2.2 | N/A | N/A | 4.3 | 11.0 |
| 17 | 2.0 | N/A | N/A | >25 | >25 |
| 18 | 1.7 | 25 | N/A | 1.1 | 25 |
| 19 | 1.3 | N/A | N/A | >25 | >25 |

FIG. 1D

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 20 | 2.8 | N/A | N/A | >25 | >25 |
| 21 | 1.8 | N/A | N/A | >25 | >25 |
| 22 | 1.0 | N/A | N/A | >25 | >25 |
| 23 | 2.8 | N/A | >25 | >25 | >25 |
| 24 | 8.6 | N/A | N/A | N/A | 12.2 |
| 25 | 3.8 | N/A | 11.1 | 8.1 | 25 |

FIG. 1E

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 26 | 1.5 | N/A | 25 | 1.0 | >25 |
| 27 | 1.0 | N/A | 4.8 | 2.5 | 25 |
| 28 | 10.0 | N/A | N/A | N/A | N/A |
| 29 | 1.6 | N/A | N/A | N/A | N/A |
| 30 | 4.9 | 7.4 | N/A | 2.9 | 25 |
| 31 | 12.3 | N/A | N/A | N/A | N/A |

FIG. 1F

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 32 | 1.8 | N/A | >25 | 6.7 | >25 |
| 33 | 3.2 | 8.5 | N/A | 2.2 | >25 |
| 34 | 5.0 | 13.1 | N/A | 4.4 | 12.0 |
| 35 | 20.0 | N/A | N/A | N/A | N/A |
| 36 | 7.3 | >25 | N/A | >25 | >25 |
| 37 | 3.3 | 6.5 | N/A | 2.5 | 7.7 |

FIG. 1G

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 38 | 2.0 | >25 | N/A | >25 | >25 |
| 39 | 8.6 | N/A | N/A | N/A | N/A |
| 40 | 1.8 | N/A | N/A | N/A | N/A |
| 41 | 2.4 | N/A | 3.0 | 1.6 | 10.8 |
| 42 | 6.4 | N/A | 18.0 | 6.1 | >25 |
| 43 | 2.6 | N/A | >25 | 1.3 | 23.2 |

FIG. 1H

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 44 | 2.6 | N/A | N/A | N/A | N/A |
| 45 | 4.8 | N/A | N/A | N/A | N/A |
| 46 | 5.3 | N/A | N/A | N/A | N/A |
| 47 | 3.3 | N/A | N/A | N/A | N/A |
| 48 | 3.3 | N/A | N/A | N/A | N/A |
| 49 | 0.6 | N/A | N/A | N/A | N/A |

FIG. 1I

| Compound | MCL-1 IC$_{50}$(μM) (Biotin Assay) | NCIH929 EC$_{50}$ (μM) | DHL6 EC$_{50}$ (μM) | MCL-1 1780 EC$_{50}$ (μM) | DHL10 EC$_{50}$ (μM) |
|---|---|---|---|---|---|
| 50 | 4.6 | N/A | N/A | N/A | N/A |
| 51 | 4.9 | 25 | 1.8 | 1.0 | >25 |
| 52 | 2.5 | N/A | N/A | N/A | N/A |
| 53 | 2.2 | N/A | N/A | N/A | N/A |

```
                          SEQUENCE LISTING

<160> NUMBER OF SEQ ID NOS: 14

<210> SEQ ID NO 1
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 1

Glu Asp Ile Ile Arg Asn Ile Ala Arg His Leu Ala Gln Val Gly Asp
1               5                   10                  15

Ser Met Asp Arg
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 2

Met Arg Pro Glu Ile Trp Ile Ala Gln Glu Leu Arg Arg Ile Gly Asp
1               5                   10                  15

Glu Phe Asn Ala
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 3

Glu Asp Ile Ile Arg Asn Ile Ala Arg His Ala Ala Gln Val Gly Ala
1               5                   10                  15

Ser Met Asp Arg
            20

<210> SEQ ID NO 4
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 4

Leu Trp Ala Ala Gln Arg Tyr Gly Arg Glu Leu Arg Arg Met Ser Asp
1               5                   10                  15

Glu Phe Glu Gly Ser Phe Lys Gly Leu
            20                  25
```

<210> SEQ ID NO 5
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 5

```
Met Glu Gly Ser Asp Ala Leu Ala Leu Arg Leu Ala Cys Ile Gly Asp
1               5                   10                  15

Glu Met Asp Val
            20
```

<210> SEQ ID NO 6
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 6

```
Ala Glu Leu Pro Pro Glu Phe Ala Ala Gln Leu Arg Lys Ile Gly Asp
1               5                   10                  15

Lys Val Tyr Cys
            20
```

<210> SEQ ID NO 7
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 7

```
Pro Ala Asp Leu Lys Asp Glu Cys Ala Gln Leu Arg Arg Ile Gly Asp
1               5                   10                  15

Lys Val Asn Leu
            20
```

<210> SEQ ID NO 8
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 8

```
Ser Ser Ala Ala Gln Leu Thr Ala Ala Arg Leu Lys Ala Leu Gly Asp
1               5                   10                  15

Glu Leu His Gln
            20
```

<210> SEQ ID NO 9
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 9

```
Val Val Glu Gly Glu Lys Glu Val Glu Ala Leu Lys Lys Ser Ala Asp
1               5                   10                  15

Trp Val Ser Asp
```

```
                 20

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 10

Glu Gln Trp Ala Arg Glu Ile Gly Ala Gln Leu Arg Arg Met Ala Asp
1               5                   10                  15

Asp Leu Asn Ala
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 11

His Gln Ala Glu Val Gln Ile Ala Arg Lys Leu Gln Leu Ile Ala Asp
1               5                   10                  15

Gln Phe His Arg
            20

<210> SEQ ID NO 12
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 12

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 13

Leu Trp Ala Ala Gln Arg Tyr Gly Arg Glu Ala Arg Arg Met Ser Asp
1               5                   10                  15

Glu Phe Glu Gly Ser Phe Lys Gly Leu
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic Peptide
```

```
-continued

<220> FEATURE:
<221> NAME/KEY: MISC_FEATURE
<222> LOCATION: (1)..(1)
<223> OTHER INFORMATION: Xaa may be beta alanine
<220> FEATURE:
<221> NAME/KEY: MISC_FEATURE
<222> LOCATION: (1)..(1)
<223> OTHER INFORMATION: May be modified with biotin
<220> FEATURE:
<221> NAME/KEY: MISC_FEATURE
<222> LOCATION: (27)..(27)
<223> OTHER INFORMATION: May be modified with an amide group

<400> SEQUENCE: 14

Xaa Asp Met Arg Pro Glu Ile Trp Ile Ala Gln Glu Leu Arg Arg Ile
1               5                   10                  15

Gly Asp Glu Phe Asn Ala Tyr Tyr Ala Arg Arg
            20                  25
```

COMPOSITIONS AND METHODS USEFUL FOR TREATING DISEASES

PRIORITY

This application is a division of U.S. application Ser. No. 14/003,733 (§371(c) date: Mar. 18, 2014), now U.S. Pat. No. 9,051,305, which is a §371 National Phase Application of PCT/US2012/028263, filed Mar. 8, 2012, and claims the benefit of U.S. Provisional Application No. 61/450,369, filed Mar. 8, 2011. The entire disclosures of each are incorporated into this application by reference.

GOVERNMENT SUPPORT

Research leading to this invention was in part funded by SBIR grant number 1R43CA135915-01 from the National Cancer Institute, National Institutes of Health, Bethesda, Md.

SEQUENCE LISTING

The instant application contains a Sequence Listing which has been submitted in ASCII format via EFS-Web and is hereby incorporated by reference in its entirety. Said ASCII copy, created on Aug. 10, 2015, is named EUTR-00703US_ST25.txt and is 4,933 bytes in size.

FIELD OF THE INVENTION

This invention relates generally to compositions and methods for treating cancer and autoimmune diseases. Cancer may include hematological malignancies, such as Multiple Myeloma and B-cell lymphoma. More specifically, the invention relates to treating cancers including hematological malignancies, with compounds that inhibit the Bcl-2 family protein Mcl-1 as well as other of the Bcl-2 family proteins. In addition, this invention relates to methods for determining selectivity of newly classified "BH3 mimic" compounds to predict efficacy in treating hematological and other malignancies involving Mcl-1.

BACKGROUND

Currently the prevalence of Multiple Myeloma is 63,000 people in the U.S. with about 13,000 new cases per year. There are 360,000 cases of non-Hodgkin's lymphoma (NHL) in the United States and 550,000 worldwide, with about 56,000 cases diagnosed per annum and 23,000 deaths per annum (American Cancer Society, The SEER Cancer Statistics Review (CSR) web site, http://seer.cancer.gov/csr/1975_20021). Twenty percent of these do not respond to current therapy. In terms of all NHL cases, 60% are aggressive, of which 50% do not respond to front line therapy. In addition, chronic lymphocytic leukemia (CLL) is the most common form of adult leukemia in the U.S. and in most of Western Europe. There are approximately 70,000 cases of CLL in the U.S., with 10,000 new cases diagnosed per annum (www.cancer.gov/cancertopics/types/leukemia). CLL patients have a poor survival prognosis with a five-year survival rate of 46%.

Mcl-1 is a key regulator of lymphoid cancers including multiple myeloma (MM) (Zhang, et al. (2002), Blood 99:1885-1893), non-Hodgkin's lymphomas (Cho-Vega, et. al (2004) Hum. Pathol. 35(9): 1095-100) and chronic lymphocytic leukemia (CLL) (Michaels, et al. (2004), Oncogene 23: 4818-4827). Additionally, treatment of myeloma cells with the proteasome inhibitor Bortezomib (Velcade) has been shown to cause elevated Mcl-1 expression (Nencioni, et al. (2005), Blood 105(8): 3255-62) and this is seen in some myeloma patients (Podar, et al. (2008) Oncogene 27(6): 721-31). It is proposed that a Mcl-1 inhibitor would enhance the efficacy of Velcade treatment in MM patients.

Though Rituxan, which targets the B-cell surface protein CD-20, has proven to be a valuable front line therapeutic for many NHL and CLL patients, resistance to this drug has been shown to correlate with elevated expression of B-cell lymphoma 2 (Bcl-2) or Myeloid Cell factor-1 (Mcl-1) proteins (Hanada, et al. (1993) Blood 82: 1820-28; Bannerji, et al. (2003) J. Clin. Oncol. 21(8): 1466-71). Notably, there is a high correlation of elevated Mcl-1 with non-responsiveness to chemotherapies in B-cells from CLL patients. (Kitada, et al. (2002) Oncogene 21: 3459-74). Rituxan-resistant CLL cells also have a higher Mcl-1/Bax ratio than normal cells, while there is no significant correlation of the Bcl-2/Bax ratio. (Bannerji, et al. (2003) supra).

Moreover, approximately 30% of diffuse large cell lymphomas (DLCLs) have increased Bcl-2 expression levels. This correlates with poor patient response to treatment with combination chemotherapy (Mounier, et al. (2003) Blood 101: 4279-84). In follicular non-Hodgkin's lymphomas and plasma cell myeloma, Mcl-1 expression positively correlates with increasing grade of the disease (Cho-Vega, et al. (2004) Hum. Pathol. 35(9): 1095-100).

The value of Bcl-2 as a target in anti-tumor therapy has been well established. The literature also reports on Mcl-1 as a target in treating NHL, CLL, and acute mylogenous leukemia (AML) (Derenne, et al. (2002) Blood, 100: 194-99; Kitada, et al. (2004) J. Nat. Canc. Inst. 96: 642-43; Petlickovski, et al. (3018) Blood 105: 4820-28). Researchers have recognized that proteins in the Bcl-2 family regulate apoptosis and are key effectors of tumorigenesis (Reed, (2002) Nat Rev. Drug Discov. 1 (2): 111-21). Bcl-2 promotes cell survival and normal cell growth and is expressed in many types of cells including lymphocytes, neurons and, self-renewing cells, such as basal epithelial cells and hematopoietic progenitor cells in the bone marrow.

In many cancers, anti-apoptotic Bcl-2 proteins, such as Bcl-2 and Mcl-1, unfortunately block the sensitivity of tumor cells to cytostatic or apoptosis inducing drugs. These proteins are therefore targets for anti-tumor therapy. A recently described class of small molecules that inhibit Bcl-2 family proteins are the BH3 mimetic compounds (Andersen, et al. (2005) Nat. Rev. Drug Discov. 4: 399-409). These compounds function by inhibiting BH3 mediated protein/protein interactions among the Bcl-2 family proteins. Several studies have described BH3 mimetic small molecules that function as Bcl-2 inhibitors by blocking BH3 binding (reviewed in Reed, et al. (2005) Blood 106: 408-418). Compounds with BH3 mimic function include HA-14-1 (Wang, et al. (2000) Proc. Natl. Acad. Sci. USA 97: 7124-9), Antimycin-A (Tzung, et al. (2001) Nat. Cell. Biol. 3: 183-191), BH3I-1 and BH3I-2 (Degterev, et al. (2001) Nat. Cell. Biol. 3: 173-82), and seven un-named compounds (Enyedy, et al. (2001) J. Med Chem 44: 4313-24), as well as a series of terphenyl derivatives (Kutzki, et al. (2002) J. Am. Chem. Soc. 124: 11838-9), and two new classes of molecules (Rosenberg, et al. (2004) Anal. Biochem. 328: 131-8). More recently, a BH3 mimic compound has been tested in a mouse tumor model (Oltersdorf, et al. (2005) Nature 435: 677-81).

The promise for using BH3 mimetic compounds as anti-tumor therapeutics has been recognized. However, to date there are no conclusive reports from the clinic on the efficacy of any anti-cancer drug with this mode of action. While pharmacological manipulation of the Bcl-2 family proteins is a feasible approach to achieving therapeutic benefit for cancer patients, the complexity of the network of proteins that comprise this family makes this prospect difficult. Therefore, with the large unmet medical need for treating hematological malignancies, new approaches to assessing and utilizing the detailed activity of the BH3 mimetic molecules will have value in developing this class of therapeutics.

SUMMARY OF THE INVENTION

Accordingly, the present invention is based on the discovery of compounds and methods useful for treating cancer and autoimmune diseases.

Accordingly, in one aspect, compounds of Formula I are described:

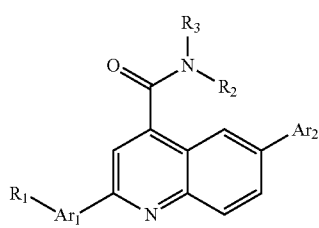

Formula I or a stereoisomer thereof, tautomer thereof, solvate thereof, or a pharmaceutically acceptable salt thereof, wherein:

$Ar_1$ is $C_{5-10}$ heteroaryl which is optionally substituted with one or more substituent $R_1$ wherein the substituents may be the same or different;

$Ar_2$ is phenyl or $C_{5-10}$ heteroaryl, each of which is optionally substituted with one or more substituent selected from $C_{1-6}$ alkyl, F, Cl, Br, I, cyano, $C_{1-6}$ alkoxy, or $C_{6-10}$ aryloxy, $C_{5-10}$ aryl wherein the substituents may be the same or different;

$R_1$ is independently selected from hydrogen or substituted or unsubstituted $C_{1-6}$ alkyl; and $R_2$ and $R_3$ are each independently selected from hydrogen, substituted or unsubstituted $C_{1-6}$ alkyl, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted $C_{1-10}$ aminoalkyl, substituted or unsubstituted $C_{5-10}$ aryl, substituted or unsubstituted saturated or unsaturated 3-11 member heteroaryl or heteroarylalkyl containing 1, 2, 3, or 4 heteroatoms selected independently from N, O, S, or $S(O)_2$ or $R_2$ and $R_3$ may be combined with the nitrogen to which they are attached to form a 3, 4, 5, 6, or 7 membered heterocyclein which one or more of the carbons may be substituted with a heteratom selected from O, N, or S and in which any of the hydrogens of the heterocycle may be substituted with $C_{1-6}$ alkyl, F, Cl, Br, I, cyano, $C_{1-6}$ alkoxy, or $C_{6-10}$ aryloxy.

In another aspect, there is provided compounds of Formula II:

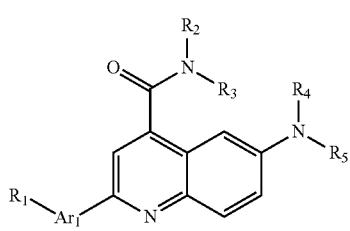

Formula II or a stereoisomer thereof, tautomer thereof, solvate thereof, or a pharmaceutically acceptable salt thereof, wherein:

$Ar_1$ is $C_{5-10}$ heteroaryl which is optionally substituted with one or more substituent $R_1$ wherein the substituents may be the same or different;

$R_1$ is independently selected from hydrogen or substituted or unsubstituted $C_{1-6}$ alkyl;

$R_2$ and $R_3$ are each independently selected from hydrogen, substituted or unsubstituted $C_{1-6}$ alkyl, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted $C_{1-10}$ amino alkyl, substituted or unsubstituted $C_{5-10}$ aryl, or substituted or unsubstituted saturated or unsaturated 3-11 member heteroaryl or heteroarylalkyl containing 1, 2, 3, or 4 heteroatoms selected independently from N, O, S, or $S(O)_2$ or $R_2$ and $R_3$ may be combined with the nitrogen to which they are attached to form a 3, 4, 5, 6, or 7 membered heterocyclein which one or more of the carbons may be substituted with a heteratom selected from O, N, or S and in which any of the hydrogens of the heterocycle may be substituted with $C_{1-6}$ alkyl, F, Cl, Br, I, cyano, $C_{1-6}$ alkoxy, or $C_{6-10}$ aryloxy; and $R_4$ and $R_5$ are independently selected from hydrogen, substituted or unsubstituted $C_{1-6}$ alkyl, substituted or unsubstituted $C_{1-6}$ aminoalkyl, or substituted or unsubstituted saturated or unsaturated 3-11 member heteroaryl or heteroarylalkyl containing 1, 2, 3, or 4 heteroatoms selected independently from N, O, S, or $S(O)_2$.

In addition to the compounds of Formula I or Formula II, the invention is also directed to the composition of and use in treating cancer and autoimmune diseases in patients with compounds having common substructures or scaffolds identified by analysis of common structural features of the compounds of Formula I or Formula II, including but not limited to the scaffolds defined in Formula I or Formula II.

In still another aspect, the invention is directed to methods of treating cancer in patients with compounds of Formula I or Formula II. Cancer may include, for example, hematological malignancies. Such hematological malignancies include, for example, Multiple Myeloma, B-cell lymphoma, acute myelogenous leukemia, and chronic lymphocytic leukemia. Treatment results in, for example, tumor regression. Tumor regression can include, for example, killing a cancer cell.

Another aspect of the invention is a method for treating particular types of hematopoietic cancers, using a compound of Formula I or Formula II. The use of these compounds for particular types of hematopoietic cancers have unexpected results in terms of, for example, efficacy and/or ability to inhibit particular anti-apoptotic (pro-survival) members of the Bcl-2 family or to mimic particular members of the pro-apoptotic Bcl-2 family proteins. Accordingly, hematological tumor cells that are hyper-dependent on a particular member of the Bcl-2 family of proteins will be highly impacted by BH3 mimics which targets that protein.

In a further aspect, the invention provides a method for killing a cancer cell comprising administering an amount of a compound of Formula I or Formula II effective to kill a cancer cell of a hematopoietic cancer. The types of hematopoietic cancer include, but are not limited to, Multiple Myeloma, B cell lymphoma, chronic lymphocytic leukemia, and acute myelogenous leukemia.

In another aspect, the invention provides a method for killing a cancer cell comprising administering an amount of compound of Formula I or Formula II in combination with a chemotherapeutic agent or agents that increases the level of Mcl-1 in the cancer cell. Such chemotherapeutic agents can include 26S proteasome inhibitors and inhibitors of the BH3 domain containing E3 ligase called Mule. Such agents may be, but not limited to, bortezomib or rituximab.

In one embodiment, the invention provides a method for killing a cancer cell comprising administering an amount of compound of Formula I or Formula II in combination with a 26S proteasome inhibitor to kill the cancer cell. A non-limiting exemplary proteasome inhibitor is bortezomib.

In another aspect, the invention provides a method for treating particular types of hematopoietic cancers using a compound of Formula I or Formula II. One or more of these compounds may inhibit the activity of the Bcl-2 family protein Mcl-1.

In one aspect, the compounds of Formula I or Formula II are used in a method for treating particular types of hematopoietic cancers, such as B-cell lymphoma, to inhibit the binding of a peptide comprised of the BH3 domain of Bak to the Bcl-2 family protein Mcl-1. This activity is unique among all of the BH3 mimics reported as of the time of filing this application and directs the use of this compound in treating certain hematological malignancies that are affected principally by the Bcl-2 family proteins and among those proteins, mostly by Mcl-1. Based on the unique ability of compounds of Formula I or Formula II to inhibit BH3 binding to Mcl-1, these compounds are useful in blocking the unwanted cell survival activity of Mcl-1 in tumorogenic lymphoid and myeloid cells, and therefore may be used as a therapy for treating Multiple Myeloma (MM), diffuse large B-cell lymphoma (DLBCL), chronic lymphocytic leukemia (CLL), acute myelogenous leukemia (AML), all of which are effected by elevated Mcl-1.

In another aspect, the invention provides a method for treating particular types of hematopoietic cancers using a combination of one or more compounds selected from the compounds of Formula I or Formula II, in combination with other therapies, for example, a class of therapeutics known as 26S proteasome inhibitors, such as, for example, Bortezomib (Velcade®).

In another aspect, the invention is directed to methods of treating autoimmune diseases in patients with compounds of formula identified in Formula I or Formula II. The autoimmune disease may be Type I diabetes, rheumatoid arthritis, osteo arthritis, psoriatic arthritis, psoriasis, neuromyaotonia, mayasthenia gravis, lupus erythematosus, endometriosis, Graves disease, granulomatosis, Crohn's disease, interstitial cystitis, or multiple sclerosis, among others.

In another aspect, the invention provides a method for determining whether a candidate compound mimics a ligand specific for a target, the method comprising the steps of (a) providing in a first reaction, the target, a first labeled peptide specific for the target, and a first unlabeled peptide specific for the target, (b) providing in a second reaction, the target, the first labeled peptide specific for the target, and a first candidate compound, (c) comparing binding specificity of the first unlabeled peptide with binding specificity of the first candidate compound to determine whether the candidate compound mimics the first unlabeled peptide. In other aspects of the invention, this method further comprises repeating steps (a), (b), and (c) wherein the first labeled peptide specific for the target is replaced with a second labeled peptide specific for the target. In some aspects, the target comprises a BH3 domain binding region, such as, for example, a hydrophobic pocket formed by the BH1, BH2, BH3 and BH4 domains of the anti-apoptotic Bcl-2 family of proteins.

In another aspect, the invention provides methods for identifying specific activity of BH3 mimic compounds. For example, these compounds can have varying potencies in inhibiting BH3-mediated binding of particular Bcl-2 family proteins, and the difference in potency can be identified by systematically ordering combinations of protein-protein interactions and comparing the blocking activity of BH3 mimic compounds to that of competing BH3 domain containing peptides. By matching the activity of the compound to a particular BH3 domain peptide, a biological activity can be assigned to that compound that correlates to the activity of the BH3 domain containing protein. This information can be used to predict the utility of a BH3 mimic compounds in treating a particular disease.

In one aspect, the invention provides an agent, which modulates apoptosis by binding to the Bcl-2 family proteins, including Mcl-1 and blocks BH3 domain binding.

In another aspect, the invention provides a method for using a compound of Formula I or Formula II to inhibit Mcl-1.

In another aspect, the invention provides a method for blocking binding of the BH3-only Bcl-2 family proteins or parts thereof, including Puma, Noxa, Bim, Bid and Bak, to Mcl-1.

In another aspect, the invention provides a method for using a compound of Formula I or Formula II as to target Mcl-1 as inhibitors to induce apoptosis in cells over expressing Mcl-1.

In another aspect, the invention provides a method for blocking binding of the BH3-only proteins or parts thereof, including Puma, Noxa, Bim, Bid and Bak, to Mcl-1.

In another aspect, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating cancer and cancer patients, including those with drug resistance, either alone or in combination with other anti-tumor agents.

In one embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating lymphoid malignancies either alone or in combination with other anti-tumor agents.

In another embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating myeloid cancer either alone or in combination with other anti-tumor agents.

In another embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating prostate cancer either alone or in combination with other anti-tumor agents.

In another embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating non-Hodgkin's lymphoma patients who are resistant to Rituxan either alone or in combination with other anti-tumor agents.

In another embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating Chronic Lymphocytic Leukemia patients who are resistant to Rituxan either alone or in combination with other anti-tumor agents.

In still another embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating breast cancer either alone or in combination with other anti-tumor agents.

In yet another embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating liver cancer either alone or in combination with other anti-tumor agents.

In another embodiment, the invention provides a method for using a specific BH3 mimic compound of Formula I or Formula II for inhibiting the activity of the Bcl-2 family protein Mcl-1 and other members of the Bcl-2 family of anti-apoptotic proteins for the purpose of treating ovarian cancer either alone or in combination with other anti-tumor agents.

In another aspect, the invention provides a method for treating cancer patients with a compound of Formula I or Formula II in combination with proteasome inhibitors.

In one embodiment, the invention provides a method for treating myelogenous leukemia with a compound of Formula I or Formula II in combination with Bortezomib or other proteasome inhibitors.

In another embodiment, the invention provides a method for treating chronic lymphocytic leukemia with a compound of Formula I or Formula II in combination with Bortezomib.

In still another embodiment, the invention provides a method for treating Non-Hodgkin's lymphoma with a compound of Formula I or Formula II in combination with Bortezomib.

In another embodiment, the invention provides a method for treating breast cancer with a compound of Formula I or Formula II in combination with Bortezomib.

In yet another embodiment, the invention provides a method for treating prostate cancer with a compound of Formula I or Formula II in combination with Bortezomib.

In a further embodiment, the invention provides a method for treating colon cancer with a compound of Formula I or Formula II in combination with Bortezomib.

In another embodiment, the invention provides a method for treating pancreatic cancer with a compound of Formula I or Formula II in combination with Bortezomib.

In another embodiment, the invention provides a method for treating liver cancer with a compound of Formula I or Formula II in combination with Bortezomib.

In another aspect, the invention provides a method for identifying a compound of the BH3 mimic class of small molecules that is an active against a subset of the BH3 domain containing proteins and therefore has predicted efficacy against particular tumor types.

In another aspect, the invention provides a method of treating a mammal suffering from migrating transformed B-cell tumors (non-Hodgkin's) comprising the steps of administering a compound of Formula I or Formula II and monitoring said mammal to determine the state of said cancer; wherein said cancer is a cancer sensitive to said chemical targeted to Bcl-2 family proteins; optionally wherein the amount administered is a quantity sufficient to constitute effective treatment, or wherein said cancer is chosen from a group of cancers comprising: lymphoma, breast cancer, leukemia, lung cancer, bone cancer, prostate cancer gastric cancer, colon cancer, rectal cancer, liver cancer, cervical cancer, renal cancer, bladder cancer, nasopharyngeal cancer, esophagus cancer, pituitary gland tumor, thyroid cancer melanoma, and pancreatic cancer.

In another aspect, the invention provides a method of preventing cancer comprising the step of administering a compound of Formula I or Formula II to persons having a high risk of cancer.

In another aspect, the invention provides a method for selecting specific activity of a BH3 mimic compound based on similar activity to a peptide comprised of a particular BH3 domain.

In various embodiments of the invention, a mammal is a human. In various embodiments of the invention, cancer is: Non-Hodgkin's Lymphoma; any other B-cell lymphomas; Small lymphocytic, consistent CLL; Follicular, predominantly small cleaved cell; Follicular, mixed small cleaved and large cell; Intermediate grade Follicular, large cell; Diffuse, small cleaved cell; Diffuse, mixed small cleaved and large cell; Diffuse, large cell (cleaved and non-cleaved); High grade; Large cell, immunoblastic; Lymphoblastic; Small non-cleaved cell; Burkitt's lymphoma; Non-Burkitt's lymphoma; Indolent NHL; B-cell CLL/small lymphocytic lymphoma; Marginal zone lymphoma; MALT; Splenic marginal 27. 27; zone lymphoma; Nodal marginal zone lymphoma; Lymphomplasmacytoid lymphoma/immunocytoma; Follicle center lymphoma, follicular type Grade I (0-5 centroblasts/hpf) or Grade II (6-15 centroblasts/hpf) or Grade III (>15 centroblasts/hpf); Aggressive NHL; Diffuse, large cell lymphoma; cancer is Mediastinal large cell lymphoma; Primary effusion lymphoma; Mantle cell lymphoma; Burkitt's lymphoma/high-grade Burkitt's-like; Precursor B-cell leukemia/lymphoma; Precursor T-cell leukemia/lymphoma; skin cancer; prostate cancer; gastric cancer; cancer is colon cancer; rectal cancer; liver cancer; cervical cancer; renal cancer; bladder cancer; nasopharyngeal cancer; esophagus cancer; pituitary gland tumor; thyroid cancer; melanoma; small-cell lung cancer; non-small cell lung cancer, or pancreatic cancer.

In various embodiments of the invention, a mammal is a human; cancer is Multiple Myeloma.

In addition, in various embodiments of the invention, a compound of the invention is administered by injecting it directly into a tumor; a compound of the invention is administered by injecting it into said mammal's blood stream; a compound of the invention is administered orally; a compound of the invention is administered through said mammal's skin; a compound of the invention is administered in combination with chemotherapy agents; or a compound of the invention are administered in combination with radiation therapy.

The details of the invention are set forth in the accompanying description below. Although methods are materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE DRAWINGS

The objects and features of the invention may be more fully understood by reference to the drawings as described below in which:

FIG. 1A-FIG. 1I is a table containing the chemical structures of BH3 domain inhibitor compounds 1-66, their MCL-1 inhibitory constants (IC$_{50}$, in μM), and EC$_{50}$ values obtained in cytotoxicity assays measuring in vitro activity of the compounds against four cancer cell lines (NCIH929, DHL6, MCL-11780, and DHL10) as described in Example 2.

DETAILED DESCRIPTION OF THE INVENTION

Figure 2:
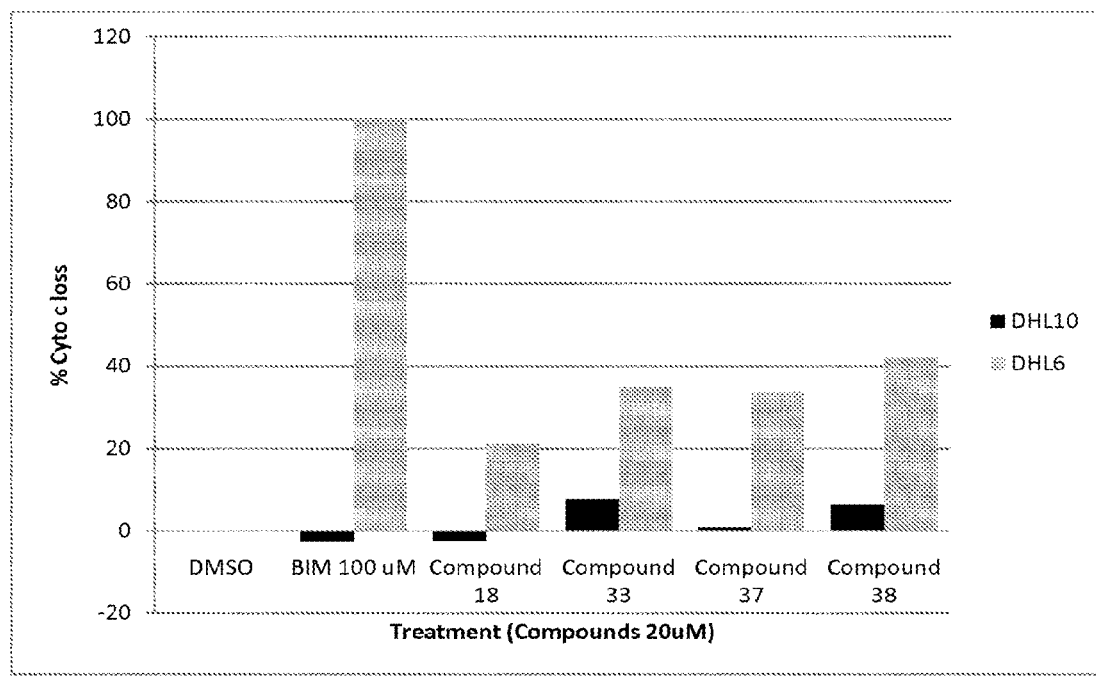
FIG. 2 is a table showing the response of mitochondria in semi-permeablized lymphoid cell lines SUDHL-6 and SUDHL-10 to compounds 18, 33, 37, and 38 (administered at 20 uM), demonstrating that these compounds cause release of cytochrome c in SUDHL-6 BAX/BAK-functional cell line but not BAX/BAK-deficient SUDHL-10 cell line, as described in Example 3.

This invention relates generally to compositions and methods for treating cancer, including hematological malignancies, such as Multiple Myeloma and B-cell lymphoma, and autoimmune diseases. Further, the invention relates to treating cancers and autoimmune diseases, with a compound that inhibits the Bcl-2 family protein Mcl-1 as well as other of the Bcl-2 family proteins. In addition, this invention relates to methods for determining selectivity of newly classified "BH3 mimic" compounds to predict efficacy in treating hematological and other malignancies involving Mcl-1.

DEFINITIONS

As used herein "anti-apoptotic-protein" is a protein, which when expressed in a cell, decreases cell death as compared to a cell that does not express the anti-apoptotic protein. In certain instances cell death in the cell containing the anti-apoptotic protein is decreased at least 10% to 90% relative to a control. For instance cell death may be decreased by about 90%, 80%, 70%, 60%, 50%, 40%, 30%, 20% and 10%.

As used herein "hematological malignancies" refers to any cancer of the blood or bone marrow, such as leukemia or lymphoma. Examples include, but are not limited to: Myclomas (e.g. Multiple myeloma and Giant cell mycloma), Acute lymphoblastic leukemia (ALL), Acute myelogenous leukemia (AML), Acute myelogenous leukemia (AML), Chronic myelogenous leukemia (CML), Acute monocytic leukemia (AMOL), Hodgkin's lymphomas (e.g., all four subtypes). In addition, Non-Hodgkin's lymphomas such as Diffuse large B-cell lymphoma (DLBCL), Follicular lymphoma (FL), Mantle cell lymphoma (MCL), Marginal zone lymphoma (MZL), Burkitt's lymphoma (BL), Burkitt's lymphoma (BL), and other NK- or T-cell lymphomas are included.

As used herein, the term "Bcl-2" refers to the protein originally discovered as the causal "oncogene" in lymphomas.

As used herein "pro-apoptotic protein" means a protein that when expressed in a cell increases cell death, as compared to a cell that does not express the pro-apoptotic protein. In certain instances cell death in the cell containing the pro-apoptotic protein is increased at least 10% to 90% relative to a control. For instance cell death may be increased by about 90%, 80%, 70%, 60%, 50%, 40%, 30%, 20% and 10%.

By "disrupts an interaction" it is meant that a test compound decreases the ability of two polypeptides to interact with each other. In certain instances the disruption results in at least a 99% decrease in the ability of the polypeptides to interact with each other. Disruptions can be identified using a combination of virtual screening for molecular structures, which fit the ideal structure of BH3 pocket, and competition binding studies using fluorescence polarization (FP).

"Fluorescence polarization assay" means an assay in which an interaction between two polypeptides is measured. In this assay, one polypeptide is labeled with a fluorescent tag, and this polypeptide emits non-polarized light when excited with polarized light. Upon an interaction of the tagged polypeptide with another polypeptide, the polarization of emitted light is increased, and this increased polarization of light can be detected.

"Interacts" means a compound that recognizes and binds to an anti-apoptotic protein but which does not substantially recognize and bind to other molecules in a sample.

"Heteroaryl" refers to mono, bicyclic, and tricyclic aromatic groups of 5 to 10 atoms containing at least one heteroatom and at least one aromatic ring. Heteroatom as used in the term heteroaryl refers to oxygen, sulfur and nitrogen. Examples of monocyclic $C_3$-$C_9$ heteroaryls include, but are not limited to, pyrrolyl, oxazinyl, thiazinyl, pyridinyl, diazinyl, triazinyl, tetrazinyl, imidazolyl, tetrazolyl, isoxazolyl, furanyl, furazanyl, oxazolyl, thiazolyl, thiophenyl, pyrazolyl, triazolyl, and pyrimidinyl. Examples of bicyclic $C_4$-$C_{10}$ heteroaryls include but are not limited to, benzimidazolyl, indolyl, indolinyl, isoquinolinyl, quinolinyl, quinazolinyl, benzothiophenyl, benzodioxolyl, benzo[1,2,5]oxadiazolyl, purinyl, benzisoxazolyl, benzoxazolyl, benzthiazolyl, benzodiazolyl, benzotriazolyl, isoindolyl and indazolyl.

"Alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it.

"Alkoxy" refers to the group R—O— where R is an alkyl group, as defined above. Exemplary $C_1$-$C_6$ alkoxy groups include but are not limited to methoxy, ethoxy, n-propoxy, 1-propoxy, n-butoxy and t-butoxy.

"Aryl" refers to an aromatic hydrocarbon group. If not otherwise specified, in this specification the term aryl refers to a $C_6$-$C_{14}$ aryl group. Examples of an $C_6$-$C_{14}$ aryl group include, but are not limited to, phenyl, 1-naphthyl, 2-naphthyl, 3-biphen-1-yl, anthryl, tetrahydronaphthyl, fluorenyl, indanyl, biphenylenyl, and acenaphthenyl, groups. An aryl group can be unsubstituted or substituted with one or more of the following groups: $C_1$-$C_6$ alkyl, $C_3$-$C_{10}$ cycloalkyl, $C_1$-$C_6$ perfluoroalkyl-, halo, haloalkyl-, hydroxyl, $C_1$-$C_6$ hydroxylalkyl-, —NH$_2$, aminoalkyl-, —COOH, carboxylic ester, primary, secondary, or tertiary carboxylic amide, urea, —C(O)O—($C_1$-$C_6$ alkyl), —OC(O)($C_1$-$C_6$ alkyl), N-alkylamido-, —C(O)NH$_2$, ($C_1$-$C_6$ alkyl)amido-, —S(O)$_2$N-alkyl, —S(O)$_2$N-aryl, alkoxy, or —NO$_2$.

"Aryloxy" refers to the group R—O— where R is an aryl group, as defined above. Exemplary $C_1$-$C_6$ alkoxy groups include but are not limited to methoxy, ethoxy, n-propoxy, 1-propoxy, n-butoxy and t-butoxy.

"Alkenyl" refers to a straight or branched chain unsaturated hydrocarbon containing at least one double bond.

"Alkynyl" refers to a straight or branched chain unsaturated hydrocarbon containing at least one double bond.

"Cycloalkyl" refers to a hydrocarbon ring containing the indicated number of carbon atoms.

"Cycloalkenyl" refers to a hydrocarbon ring containing the indicated number of carbon atoms and at least one double bond.

"Aminoalkyl" refers to an alkyl group, as defined above, wherein one or more of the alkyl group's hydrogen atoms has been replaced with N. This N may be further substituted with alkyl groups, aryl groups, heteroaryl groups, heteroarylalkyl groups, or aminoalkyl groups.

"Heteroarylalkyl" refers to an alkyl group, as defined above, wherein one or more of the alkyl group's hydrogen atoms has been replaced with a heteroaryl group as defined above.

"Heteroalkyl" refers to refers to a hydrocarbon chain that may be a straight chain or branched chain and contains at least one heteroatom consisting of N, O, or S.

The present invention relates to compositions and methods for the treatment of cancer and autoimmune disease. More specifically, the present invention relates to compositions and methods for treating hematological malignancies. Such hematological malignancies include, for example, Multiple Myeloma, B-cell lymphoma, acute myelogenous leukemia, and chronic lymphocytic leukemia. Such treatment, results in, for example, tumor regression in a mammal, such as a mouse or a human. Tumor regression can include, for example, killing a cancer cell.

The invention also relates to compounds of Formula I or Formula II.

The invention also relates to treating hematological malignancies with a compound of Formula I or Formula II, and/or a BH3 mimic compound that inhibits a broad range of the Bcl-2 family of proteins, most notably Mcl-1. It is contemplated that the activity against the protein Mcl-1 of a compound of Formula I or Formula II as well as derivative compounds will enable therapeutic utility of these compounds as anti-tumor agents in treating cancer, including blood cancers.

The invention, for example, provides a method for treating particular types of hematopoietic cancers, using a BH3 mimic compound of Formula I or Formula II. The use of these compounds for particular types of hematopoietic cancers may have unexpected results in terms of efficacy and/or ability to inhibit particular anti-apoptotic (pro-survival) members of the Bcl-2 family or to mimic particular members of the pro-apoptotic Bcl-2 family proteins. Accordingly, hematological tumor cells that are hyper-dependent on a particular member of the Bcl-2 family of proteins may be highly affected by that BH3 mimic which targets that protein.

A compound Formula I or Formula II may be particularly useful in a method of treating hematopoietic cancers, by inhibiting the binding of the activator BH3 only proteins of the Bcl-2 family to protein Mcl-1. The high affinity of these compounds towards MCL-1 (<20 µM) directs the use of these compounds in treating certain hematological malignancies that are affected principally by the Bcl-2 family proteins and among those proteins, mostly by Mcl-1. Based on the unique ability of a compound of Formula I or Formula II to inhibit BH3 binding to Mcl-1, these compounds may be particularly effective in blocking the unwanted cell survival activity of Mcl-1 in tumorogenic lymphoid and myeloid cells. This feature of compounds of Formula I or Formula II will direct their use as a potential therapeutic agents for treating Multiple Myeloma (MM), diffuse large B-cell lymphoma (DLBCL), chronic lymphocytic leukemia (CLL), acute myelogenous leukemia (AML), all of which are effected by elevated Mcl-1. Similar activity in derivatives of compounds of Formula I or Formula II, may direct the use of those compounds in treating lymphoid and myeloid malignancies.

This invention also relates to using a compound of Formula I or Formula II to cause tumor regression and enhance survival in B-cell lymphomas. Accordingly, in one embodiment, this invention describes a method for using a compound of Formula I or Formula II for the treatment of non-Hodgkin's B-cell lymphoma, including CLL, Burkett's, Indolent and Aggressive non-Hodgkin's lymphomas, Multiple Myelomas, or other cancers that are affected by Bcl-2 family of proteins, and in particular the protein Mcl-1.

These treatments may be accomplished utilizing a compound of Formula I or Formula II alone, or in combination, with other chemotherapy agents or with radiation therapy. Accordingly, the invention provides a method for treating particular types of hematopoietic cancers using a combination of one or more compounds of Formula I or Formula II, in combination with other therapies, for example, a class of therapeutics known as 26S proteasome inhibitors. In some embodiments, the 26S proteasome inhibitor is Bortezomib (Velcade®).

In addition, this invention relates to methods for determining selectivity of a compound of Formula I or Formula II and BH3 mimic compounds to predict efficacy in treating hematological and other malignancies involving Bcl-2 family proteins. For example, these compounds can have varying potencies in inhibiting BH3 mediated-binding of particular Bcl-2 family proteins, and the difference in potency can be identified by systematically ordering combinations of protein-protein interactions and comparing the blocking activity of BH3 mimic compounds to that of competing BH3 domain-containing peptides. By matching the activity of the compound to a particular BH3 domain peptide, a biological activity can be assigned to that compound that correlates to the activity of the BH3 domain-containing protein. This information can be used to predict the utility of a BH3 mimic compounds in treating a particular disease.

This invention also relates to cancer treatments, Multiple Myeloma treatments directed to Bcl-2 and Bcl-xL and Mcl-1 and A1 and Bcl-w (referred as a group as an anti-apoptotic Bcl-2 family) activity.

The present invention also relates to determining a cellular state with respect to programmed cell death. This state has been named "primed for death". In addition to alive and dead states, cells may be primed for death in that they require tonic antiapoptotic function for survival.

Previous work demonstrated a method called BH3 profiling (Certo, et al. (2006) Cancer Cell 9(5): 351-65; Deng, et al. (2007) Cancer Cell. 12(2): 171-85; U.S. Patent Publication No. 2008/0199890). This method uses a panel of peptides derived from BH3 domains of BH3-only proteins that selectively antagonize individual BCL-2 family members BCL-2, BCL-XL, BCL-w, MCL-1 and BFL-1. It was shown that cellular "addiction" to individual antiapoptotic proteins can be diagnosed based on mitochondrial response to these peptides. This panel of peptides is shown in Table 1 and are referred to herein as BH3 domain peptides. Antiapoptotic proteins BCL-2, BCL-XL, MCL-1, BFL-1 and BCL-w each bear a unique pattern of interaction with this panel of proteins. Cellular dependence on an antiapoptotic protein for survival is decoded based on the pattern of mitochondrial sensitivity to this peptide panel. This strategy is called BH3 profiling.

TABLE 1

BH3 Domain Peptides

| | Amino Acid Sequence | SEQ ID NO |
|---|---|---|
| BID | EDIIRNIARHLAQVGDSMDR | 1 |
| BIM | MRPEIWIAQELRRIGDEFNA | 2 |
| BID mut | EDIIRNIARHAAQVGASMDR | 3 |
| BAD | LWAAQRYGRELRRMSDEFEGSFKGL | 4 |
| BIK | MEGSDALALRLACIGDEMDV | 5 |

TABLE 1-continued

BH3 Domain Peptides

|        | Amino Acid Sequence    | SEQ ID NO |
|--------|------------------------|-----------|
| NOXA A | AELPPEFAAQLRKIGDKVYC   | 6         |
| NOXA B | PADLKDECAQLRRIGDKVNL   | 7         |
| HRK    | SSAAQLTAARLKALGDELHQ   | 8         |
| BNIP   | VVEGEKEVEALKKSADWVSD   | 9         |
| PUMA   | EQWAREIGAQLRRMADDLNA   | 10        |
| BMF    | HQAEVQIARKLQLIADQFHR   | 11        |
| huBAD  | NLWAAQRYGRELRRMSDEFVDSFKK | 12     |
| BAD mut| LWAAQRYGREARRMSDEFEGSFKGL | 13     |

Mitochondria are probed to determine a cell's state using this panel of sensitizer BH3-peptides, selective antagonists of antiapoptotic BCL-2 family members. Mitochondria that are primed for death are dependent on antiapoptotic protein function to prevent mitochondrial outer membrane permeabilization (MOMP), so that they release cytochrome c when exposed to sensitizer BH3 peptides. In contrast, unprimed cells do not release cytochrome c when exposed to sensitizer BH3 peptides. Any cell from which mitochondria can be isolated can therefore be so tested and categorized as being primed or unprimed. A "snapshot" of the apoptotic state at a given time may be taken with minimal perturbation of the extant apoptotic machinery. In summary, BH3 profiling allows capture of information about a fundamental aspect of cellular physiology. Importantly, mitochondrial behavior is correlated to whole cell behavior in several models, and BH3 profiling revealed a dependence on antiapoptotic proteins only when a cellular dependence was also demonstrated.

Not all cells are sensitive to antagonism of antiapoptotic proteins. Sensitive cells are "primed for death" with death signals carried by a select subset of proapoptotic proteins of the BCL-2 family. Some cancer cells may be tonically primed for death, and thus are selectively susceptible to agents that provoke or mimic sensitizer BH3-only domains. It has been postulated that inhibition of apoptosis is a requirement of oncogenesis (Green and Evan, (2002) Cancer Cell. 1(1):19-30; Hanahan and Weinberg, (2000) Cell. 100 (1):57-70). In what may be an attempt to meet this requirement, many types of cancer cells overexpress antiapoptotic BCL-2 family members. Understanding how these proteins function is therefore critical to understanding how cancer cells maintain survival.

The present invention provides a method for determining the "primed to die" state of a cell without using peptides. This method allows the investigation of whether a particular antiapoptotic BCL-2 family member, Mcl-1, controls mitochondrial outer membrane permeabilization (MOMP) and commitment to apoptosis. Antiapoptotic proteins show selective affinity for binding BH3 peptides derived from BH3-only proteins. For example, Mcl-1 binds selectively to the BH3 peptide Noxa. Furthermore, antagonism of Mcl-1 by Noxa results in MOMP only when Mcl-1 is "primed" with activator BH3 proteins, validating the critical role of activator BH3 domains in activating BAX/BAK. In cell culture models, activator "priming" can be observed following experimentally-induced death signaling, and that such priming confers dependence on antiapoptotic family members. The dependence on antiapoptotic BCL-2 family members can be captured functionally by the pattern of mitochondrial sensitivity to sensitizer BH3 domains, and Mcl-1 dependence can be identified by sensitivity to Noxa. Accordingly, the invention includes methods of determining the sensitivity of a cell to a class of therapeutic agents, Mcl-1 inhibitors. This method identifies whether or not a cell is primed for death through an Mcl-1 dependent mechanism by measuring mitochondrial sensitivity to the Mcl-1 specific inhibitor compounds of Formula I or Formula II.

Compounds that exhibit a high degree (>10-fold) of selectivity and specificity for any specific Bcl-2 family protein can be used identify whether a cell is primed for death via a mechanism that involves other Bcl-2 family proteins. The compounds ABT-737 and ABT-263 (Tse, et al. (2008) Cancer Res. 68, 3421-3428) are highly specific to Bcl-2 and Bcl-xL ($IC_{50}$<10 nM versus Bcl-2 and Bcl-xL) but much weaker binders to Mcl-1 ($IC_{50}$<500 nM) and can be used to treat cancer cells or mitochondria from cancer cells in order to determine if the cell is primed with Bcl-2 and/or Bcl-xL and to determine if the cancer cell is sensitive to Bcl-2 and/or Bcl-xL inhibition.

Additional aspects of this approach are discussed in U.S. Patent Publication Nos. 2008-0199890 and 2009-0280510 and U.S. Pat. No. 7,868,133, the contents of which are incorporated herein by reference in their entirety.

There is provided in accordance with one aspect of the invention, compounds of Formula I:

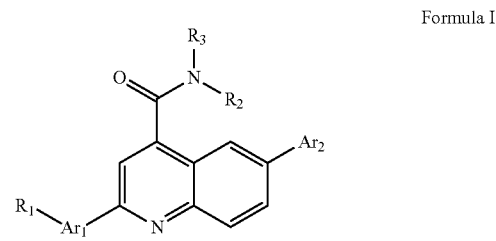

Formula I and stereoisomers thereof, tautomers thereof, solvates thereof, and pharmaceutically acceptable salts thereof, wherein:

$Ar_1$; $Ar_2$; $R_1$; $R_2$ and $R_3$ are defined as above for Formula I.
In some embodiments, $Ar_1$ is furanyl.
In other embodiments, $Ar_1$ is 2-methylfuranyl.
In other embodiments, $Ar_1$ is benzofuranyl.
In other embodiments, $Ar_1$ is pyrazolyl.
In other embodiments, $Ar_1$ is thiazolyl.
In other embodiments, $Ar_1$ is oxazolyl.
In some embodiments, $R_1$ is hydrogen.
In other embodiments, $R_1$ is alkyl.
In other embodiments, $R_1$ is heteroalkyl.
In some embodiments, $Ar_2$ is phenyl.
In some embodiments, $Ar_2$ is halo-substituted phenyl.
In some embodiments, $Ar_2$ is alkoxy-substituted phenyl.
In some embodiments, $Ar_2$ is aryl-substituted phenyl.
In some embodiments, $Ar_2$ is aryloxy-substituted phenyl.
In some embodiments, $Ar_2$ is heteroaryl.
In some embodiments, $Ar_2$ is monocyclic heteroaryl.
In some embodiments, $Ar_2$ is bicyclic heteroaryl.
In some embodiments, $Ar_2$ is alkyl-substituted heteroaryl.
In some embodiments, $Ar_2$ is benzothiazolyl.
In some embodiments, $Ar_2$ is indolyl.
In some embodiments, $Ar_2$ is benzimidazoyl.
In some embodiments, $Ar_2$ is indazoyl.
In some embodiments, $Ar_2$ is pyrazolyl.

In some embodiments, Ar₁ is furanyl and Ar₂ is halo-substituted phenyl.

In some embodiments, Ar₁ is furanyl and Ar₂ is alkoxy-substituted phenyl.

In some embodiments, Ar₁ is furanyl and Ar₂ is aryl-substituted phenyl.

In some embodiments, Ar₁ is furanyl and Ar₂ is aryloxy-substituted phenyl.

In some embodiments, Ar₁ is furanyl and Ar₂ is heteroaryl.

In some embodiments, Ar₁ is furanyl and Ar₂ is monocyclic heteroaryl.

In some embodiments, Ar₁ is furanyl and Ar₂ is bicyclic heteroaryl.

In some embodiments, Ar₁ is furanyl and Ar₂ is alkyl-substituted heteroaryl.

In some embodiments, Ar₁ is furanyl and Ar₂ is benzothiazolyl.

In some embodiments, Ar₁ is furanyl and Ar₂ is indolyl.

In some embodiments, Ar₁ is furanyl and Ar₂ is benzimidazoyl.

In some embodiments, Ar₁ is furanyl and Ar₂ is indazoyl.

In some embodiments, Ar₁ is furanyl and Ar₂ is pyrazolyl.

In some embodiments, R₂ and R₃ are not the same.

In some embodiments, R₂ and R₃ taken together form a cycloalkyl group.

In some embodiments, R₂ is hydrogen and R₃ is heteroaryl.

In some embodiments, R₂ is hydrogen and R₃ is pyridyl.

In some embodiments, R₂ is hydrogen and R₃ is alkyl.

In some embodiments, R₂ is hydrogen and R₃ is aryl.

In some embodiments, R₂ and R₃ taken together form an unsaturated heterocyclic group.

In some embodiments, R₂ is hydrogen and R₃ is cycloalkyl.

In some embodiments, R₂ is alkyl and R₃ is heteroaryl.

In other illustrative embodiments, compounds of Formula I are set forth below:

2-(furan-2-yl)-6-phenyl-N-(pyridin-3-yl)quinoline-4-carboxamide (1);

2-(furan-2-yl)-6-(1H-pyrazol-4-yl)-N-(pyridin-3-yl)quinoline-4-carboxamide (2);

6-(2-fluorophenyl)-2-(furan-2-yl)-N-(pyridin-3-yl)quinoline-4-carboxamide (3);

6-(3-fluorophenyl)-2-(furan-2-yl)-N-(pyridin-3-yl)quinoline-4-carboxamide (4);

6-(4-fluorophenyl)-2-(furan-2-yl)-N-(pyridin-3-yl)quinoline-4-carboxamide (5);

2-(furan-2-yl)-6-(3-methoxyphenyl)-N-(pyridin-3-yl)quinoline-4-carboxamide (6);

2-(furan-2-yl)-6-(4-methoxyphenyl)-N-(pyridin-3-yl)quinoline-4-carboxamide (7);

6-([1,1'-biphenyl]-4-yl)-2-(furan-2-yl)-N-(pyridin-3-yl)quinoline-4-carboxamide (8);

6-([1,1'-biphenyl]-3-yl)-2-(furan-2-yl)-N-(pyridin-3-yl)quinoline-4-carboxamide (9);

2-(furan-2-yl)-6-(3-(2-methoxyethoxyl)phenyl)-N-(pyridin-3-yl)quinoline-4-carboxamide (10);

2-(furan-2-yl)-6-(4-(2-methoxyethoxy)phenyl)-N-(pyridin-3-yl)quinoline-4-carboxamide (11);

2-(furan-2-yl)-6-(3-phenoxyphenyl)-N-(pyridin-3-yl)quinoline-4-carboxamide (12);

2-(furan-2-yl)-6-(4-phenoxyphenyl)-N-(pyridin-3-yl)quinoline-4-carboxamide (13);

2-(furan-2-yl)-N-(pyridin-3-yl)-6-(pyridin-4-yl)quinoline-4-carboxamide (14);

2-(furan-2-yl)-6-(1H-indol-6-yl)-N-(pyridin-3-yl)quinoline-4-carboxamide (15);

2-(furan-2-yl)-6-(1-methyl-1H-benzo[d]imidazol-5-yl)-N-(pyridin-3-yl)quinoline-4-carboxamide (16);

2-(furan-2-yl)-6-(1H-indazol-5-yl)-N-(pyridin-3-yl)quinoline-4-carboxamide (17);

6-(benzo[d]thiazol-5-yl)-2-(furan-2-yl)-N-(pyridin-3-yl)quinoline-4-carboxamide (18);

2-(furan-2-yl)-6-(naphthalen-2-yl)-N-(pyridin-3-yl)quinoline-4-carboxamide (19);

2-(furan-2-yl)-6-(1H-indol-3-yl)-N-(pyridin-3-yl)quinoline-4-carboxamide (20);

2-(furan-2-yl)-6-(2-oxo-2,3-dihydro-1H-benzo[d]imidazol-5-yl)-N-(pyridin-3-yl)quinoline-4-carboxamide (21);

2-(furan-2-yl)-N-(pyridin-3-yl)-[6,6'-biquinoline]-4-carboxamide (22);

2-(furan-2-yl)-6-(pyridin-2-yl)-N-(pyridin-3-yl)quinoline-4-carboxamide (23);

6-(1H-benzo[d]imidazol-5-yl)-2-(furan-2-yl)-N-(pyridin-3-yl)quinoline-4-carboxamide (26);

2-(furan-2-yl)-6-(1H-indol-5-yl)-N-(pyridin-3-yl)quinoline-4-carboxamide (28);

2'-(furan-2-yl)-N-(pyridin-3-yl)-[2,6'-biquinoline]-4'-carboxamide (29);

2-(5-methylfuran-2-yl)-6-phenyl-N-(pyridin-3-yl)quinoline-4-carboxamide (30);

2-(benzofuran-2-yl)-6-phenyl-N-(pyridin-3-yl)quinoline-4-carboxamide (31);

6-(benzo[d]thiazol-5-yl)-2-(furan-2-yl)-N-methylquinoline-4-carboxamide (32);

6-(benzo[d]thiazol-5-yl)-2-(furan-2-yl)-N-phenylquinoline-4-carboxamide (33);

2-(1,3-dimethyl-1H-pyrazol-4-yl)-6-phenyl-N-(pyridin-3-yl)quinoline-4-carboxamide (34);

2-(1-methyl-1H-pyrazol-4-yl)-6-phenyl-N-(pyridin-3-yl)quinoline-4-carboxamide (36);

6-phenyl-N-(pyridin-3-yl)-2-(1-(tetrahydro-2H-pyran-2-yl)-1H-pyrazol-4-yl)quinoline-4-carboxamide (37);

6-phenyl-2-(1H-pyrazol-4-yl)-N-(pyridin-3-yl)quinoline-4-carboxamide (38);

(6-(benzo[d]thiazol-5-yl)-2-(furan-2-yl)quinolin-4-yl)(4-methylpiperazin-1-yl)methanone (39);

6-(benzo[d]thiazol-5-yl)-N-cyclopropyl-2-(furan-2-yl)quinoline-4-carboxamide (40);

6-phenyl-N-(pyridin-3-yl)-2-(thiazol-2-yl)quinoline-4-carboxamide (41);

6-(benzo[d]thiazol-5-yl)-N-cyclohexyl-2-(furan-2-yl)quinoline-4-carboxamide (42);

2-(oxazol-2-yl)-6-phenyl-N-(pyridin-3-yl)quinoline-4-carboxamide (43);

6-(benzo[d]thiazol-5-yl)-2-(furan-2-yl)-N-(pyridin-4-yl)quinoline-4-carboxamide (44);

N-(benzo[d]thiazol-2-yl)-6-(benzo[d]thiazol-5-yl)-2-(furan-2-yl)quinoline-4-carboxamide (45);

methyl 1-(6-(benzo[d]thiazol-5-yl)-2-(furan-2-yl)quinoline-4-carbonyl)piperidine-3-carboxylate (46);

6-(benzo[d]thiazol-5-yl)-2-(furan-2-yl)-N-(pyridin-2-yl)quinoline-4-carboxamide (47);

6-(benzo[d]thiazol-5-yl)-2-(furan-2-yl)-N-methyl-N-(pyridin-3-yl)quinoline-4-carboxamide (48);

methyl 1-(6-(benzo[d]thiazol-5-yl)-2-(furan-2-yl)quinoline-4-carbonyl)piperidine-4-carboxylate (49);

N-(1H-benzo[d]imidazol-2-yl)-6-(benzo[b]thiazol-5-yl)-2-(furan-2-yl)quinoline-4-carboxamide (51);

6-(benzo[d]thiazol-5-yl)-N-methyl-2-(oxazol-2-yl)quinoline-4-carboxamide (52);

6-(benzo[d]thiazol-5-yl)-2-(oxazol-2-yl)-N-(pyridin-3-yl)quinoline-4-carboxamide (53);

6-(benzo[d]thiazol-5-yl)-2-(oxazol-2-yl)-N-(pyridin-3-yl)quinoline-4-carboxamide (57);

6-(benzo[d]thiazol-5-yl)-N-(4-methoxy-3-(piperidin-1-yl-sulfonyl)phenyl)-2-(oxazol-2-yl)quinoline-4-carboxamide (58);
N-(4-methoxy-3-(piperidin-1-ylsulfonyl)phenyl)-6-(1-methyl-1H-benzo[d]imidazol-5-yl)-2-(oxazol-2-yl)quinoline-4-carboxamide (59);
N-(4-methoxy-3-(piperidin-1-ylsulfonyl)phenyl)-2-(oxazol-2-yl)-6-phenylquinoline-4-carboxamide (60);
N-(4-methoxy-3-(piperidin-1-ylsulfonyl)phenyl)-2-(oxazol-2-yl)-[6,6'-biquinoline]-4-carboxamide (61);
N-(1H-benzo[d]imidazol-2-yl)-6-(benzo[d]thiazol-5-yl)-2-(oxazol-2-yl)quinoline-4-carboxamide (62);
N-(1H-benzo[d]imidazol-2-yl)-6-(1-methyl-1H-benzo[d]imidazol-5-yl)-2-(oxazol-2-yl)quinoline-4-carboxamide (63);
N-(1H-benzo[d]imidazol-2-yl)-2-(oxazol-2-yl)-6-phenylquinoline-4-carboxamide (64);
N-(1H-benzo[d]imidazol-2-yl)-2-(oxazol-2-yl)-[6,6'-biquinoline]-4-carboxamide (65), and;
6-(benzo[d]thiazol-5-yl)-N-methyl-2-(oxazol-2-yl)quinoline-4-carboxamide (66).

There is provided in accordance with an embodiment of the invention, compounds of Formula Ia:

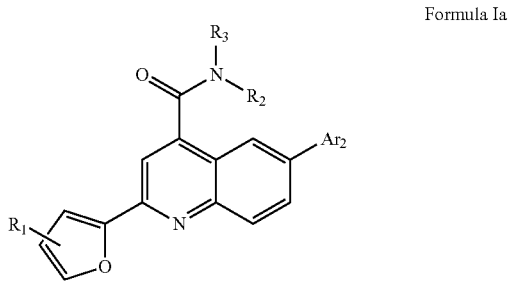

Formula Ia and stereoisomers thereof, tautomers thereof, solvates thereof, and pharmaceutically acceptable salts thereof, wherein:
$Ar_2$; $R_1$; $R_2$ and $R_3$ are defined as above for Formula I.

There is provided in accordance with another aspect of the invention, compounds of Formula II:

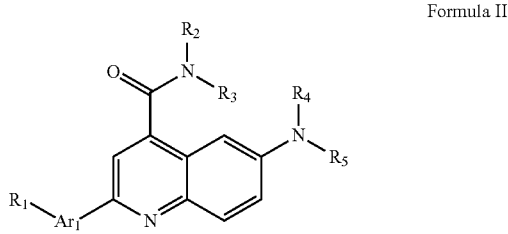

Formula II and stereoisomers thereof, tautomers thereof, solvates thereof, and pharmaceutically acceptable salts thereof, wherein:
$Ar_1$; $R_1$; $R_2$; $R_3$; $R_4$ and $R_5$ are as defined above for Formula II.

In some embodiments, $Ar_1$ is furanyl.
In some embodiments, $Ar_1$ is oxazolyl.
In some embodiments, $R_2$ is hydrogen and $R_3$ is heteroaryl.
In some embodiments, $R_2$ is hydrogen and $R_3$ is substituted aryl.
In some embodiments, $R_2$ is hydrogen and $R_3$ is alkyl.

In some embodiments, $R_4$ is hydrogen and $R_5$ is heteroaryl.
In some embodiments, $R_4$ is hydrogen and $R_5$ is aminoalkyl containing a tertiary amine.
In some embodiments, $R_4$ is hydrogen and $R_5$ is aminoalkyl containing a secondary amine.
In some embodiments, $R_4$ and $R_5$ taken together form an unsaturated heterocyclic group.
In some embodiments, $Ar_1$ is furanyl, $R_2$ is hydrogen and $R_3$ is heteroaryl.
In some embodiments, $Ar_1$ is furanyl, $R_2$ is hydrogen and $R_3$ is substituted aryl.
In some embodiments, $Ar_1$ is furanyl, $R_2$ is hydrogen and $R_3$ is alkyl.
In some embodiments, $Ar_1$ is furanyl, $R_4$ is hydrogen and $R_5$ is heteroaryl.
In some embodiments, $Ar_1$ is furanyl, $R_4$ is hydrogen and $R_5$ is aminoalkyl containing a tertiary amine.
In some embodiments, $Ar_1$ is furanyl, $R_4$ is hydrogen and $R_5$ is aminoalkyl containing a secondary amine.
In some embodiments, $Ar_1$ is furanyl, $R_4$ and $R_5$ taken together form an unsaturated heterocyclic group.

In other illustrative embodiments, compounds of Formula II are set forth below:
2-(furan-2-yl)-6-(pyridin-2-ylamino)-N-(pyridin-3-yl)quinoline-4-carboxamide (24);
6-((2-(benzyl(methyl)amino)ethyl)amino)-2-(furan-2-yl)-N-(pyridin-3-yl)quinoline-4-carboxamide (25);
2-(furan-2-yl)-6-((2-(phenylamino)ethyl)amino)-N-(pyridin-3-yl)quinoline-4-carboxamide (27);
2-(furan-2-yl)-6-((2-phenoxyethyl)amino)-N-(pyridin-3-yl)quinoline-4-carboxamide (35);
2-(furan-2-yl)-6-(4-phenylpiperazin-1-yl)-N-(pyridin-3-yl)quinoline-4-carboxamide (50);
2-(oxazol-2-yl)-6-((2-(phenylamino)ethyl)amino)-N-(pyridin-3-yl)quinoline-4-carboxamide (54);
N-(4-methoxy-3-(piperidin-1-ylsulfonyl)phenyl)-2-(oxazol-2-yl)-6-((2-(phenylamino)ethyl)amino)quinoline-4-carboxamide (55), and;
N-methyl-2-(oxazol-2-yl)-6-((2-(phenylamino)ethyl)amino)quinoline-4-carboxamide (56).

Methods of Using
A. Treatment with a Compound of Formula I or Formula II to Inhibit Bcl-2 Proteins The present invention describes, in part, anti-tumor efficacy and enhanced survivability in mouse models for hematological malignancies by treatment with a compound of Formula I or Formula II. Efficacy in certain animal models may be correlated to humans afflicted with B-cell lymphoma or other hematological or non-hematological cancers affected by Bcl-2 family proteins.

This treatment may be administered as a stand-alone therapy, or with other chemotherapy agents, or with radiation therapy. In one embodiment, a compound of Formula I or Formula II is used for the treatment of B-cell lymphoma or Multiple myeloma by inducing cancer cell death and preventing cancer cell migration to spleen or lymph nodes.

Because Mcl-1 has emerged as a key member of the Bcl-2 family of proteins for initiating and maintaining certain myeloid as well as B-cell and T-cell malignancies, it is an important target for treatment of many hematological diseases. This invention demonstrates, among others, the effectiveness of a compound of Formula I and Formula II in inhibiting BH3 binding to Mcl-1. Thus, these compounds are useful for treating Multiple Myeloma, B-cell lymphoma or other hematological cancers or other disease that are affected by Mcl-1 activity including prostate, liver, and ovarian cancers.

The compounds of Formula I and Formula II have activity against Mcl-1, therefore the compounds of Formula I and Formula II and/or other BH3 mimic compounds against Mcl-1 are useful therapeutic compounds in treating MM, NHL, CLL, AML and prostate, liver, and ovarian cancers, among others.

This activity will also direct the use of these compounds for treatment of certain autoimmune diseases that are affected by excess B or T cell proliferation.

The present invention relates to the use of a compound of Formula I or Formula II, as compositions in inhibiting the activity of Bcl-2 pro-survival proteins, most particularly Mcl-1, in tumor cells and thereby killing those cells. The unique ability of these compounds to inhibit Mcl-1 function in cells will makes these compounds effective anti-B-cell, T-cell, and myeloma cell cancer therapeutics for treating non-Hodgkin's lymphoma, CLL, MM, and AML as well as prostate, colon, ovarian, and liver cancer, among other diseases.

A compound of Formula I and Formula II, causes tumor regression, for example by killing a cancer cell, and increased survival in several mouse tumor models, including, for example, models for diffuse large B-cell lymphoma (DL-BCL) (Cattoretti, et al. (2005) Cancer Cell 7: 445-55), small B cell lymphoma/CLL (Zapata, et al. (2004) Proc. Natl. Acad. Sci. USA 101(47): 16600-5) and migrating B-cell lymphomas (Refaeli, et al. (3018) Proc. Natl. Acad. Sci. USA 102 (11): 4097-102), as well as an AML mouse tumor model (Lopes de Menezes, et al. (2005) Clin. Canc. Res. 11(14): 5281-91). All of the tumors from these cell models are characterized as having elevated pro-survival Bcl-2 family proteins, including Bcl-2, Bcl-xL, and Mcl-1.

Accordingly, the present invention relates to the use of a compound of Formula I and Formula II, in affecting tumor regression in human lymphoid and myeloid cancers. These compounds are effective in inducing apoptosis selectively in hematological cancers due to the hyper-dependence of lymphoid and myeloid-derived tumor cells on the activity of the Bcl-2 family anti-apoptotic proteins.

The Bcl-2 protein is a member of an entire family, the Bcl-2 family of proteins, that have structurally similar genes and that share sequence homology and participate in the control of programmed cell death or "apoptosis" (Corey, et al. (2002) Nat. Rev. Cancer 2: 647-656). Some members of this family (anti-apoptotic Bcl-2 family proteins), such as Bcl-2 Bcl-xL, BcL-w, Bfl-1(A1) and Mcl-1, protect cells from apoptosis. These proteins share sequence homology in four α-helical regions called the Bcl-2 homology (BH)-domains 1-4 (BH1-BH4). Another class of this family (pro-apoptotic Bcl-2 proteins), such as Bax and Bak, promote apoptosis and share three of these domains, BH1-BH3. A third class of Bcl-2 family proteins, such as Bim, Bad, Hrk, Bid, Puma, Noxa, and Bmf, share only one region, the BH3 domain, and are referred to as "BH3-only proteins." The BH3-only proteins are pro-apoptotic, and like Bax and Bak, the BH3-only proteins require an intact BH3 domain to promote apoptosis (Adams, et al. (1998) Science 281: 1322-26).

A complex interplay of the pro-apoptotic and anti-apoptotic proteins affects the integrity of the outer membrane of the mitochondria (Green, et al. (2004) Science 305: 626-29) either causing or preventing the release of certain molecules that activate the cystein aspartyl proteases (caspases). The caspases are the eventual effectors of apoptosis (Salvesen (2002) Cell Death and Differentiation 9: 3-5). Bax and Bak are essential for release of these apoptosis promoting molecules from the mitochondria (Wei, et al. (2001) Science 292: 727-30). The BH3-only proteins stimulate the activity of Bax and Bak while the anti-apoptotic proteins oppose their activity. Essentially all of these interactions occur by BH3 domain mediated binding (Chrittenden, et al. (1995) EMBO J. 14: 5589-96).

Anti-apoptotic family members Bcl-2, Bcl-xL and Mcl-1 are over-expressed in many types of cancers, including lymphomas, melanomas, myelomas, and cancer in the prostate and colon (Kitada, et al. (2002) Oncogene 21: 3459-74; Paul-Samojedny, et al. (2005) Biochem. Biophys. Acta. 1741 (1-2): 25-29; Pollack, et al. (2003) Cancer 97(7): 1630-8; Tas, et al. (2004) Melanoma Res. 14(6): 543-6). Animal model studies established that the continuous presence of anti-apoptotic family members is required for tumor survival and growth. Additionally, the pro-survival Bcl-2 proteins are important for the development of resistance of tumor cells to chemotherapies such as DNA damaging agents. The ratio of pro-apoptotic to anti-apoptotic family members has been shown in many cases to hold significant prognostic value for patient outcome. Over-expression of anti-apoptotic Bcl-2 family proteins has been reported in many of the hematopoietic malignancies. For example, increased expression of Bcl-2 protein that results from a translocation (t14; 18) of the BCL2 gene occurs in 80% to 90% of low-grade follicular non-Hodgkin lymphomas (NHLs) (Kitada, et al. (2002) supra).

Three different strategies for countering the tumorigenic effects of anti-apoptotic Bcl-2 family proteins in NHL, CLL, MM, and other types of cancer include: (1) inhibiting gene transcription; (2) using antisense oligonucleotides to cause mRNA degradation; and (3) directly inhibiting the proteins with small-molecule drugs (reviewed in Reed, et al. (2005) Blood 106: 408-418).

One of the desired characteristics of anti-tumor drugs is the ability to induce apoptosis in tumor cells and not in healthy cells. Conventional chemotherapy is mostly based on the evidence that proliferating cells are more sensitive to anticancer agents than non-dividing cells (Marchini, et al. (2004) Curr. Med. Chem. Anticancer Agents 4(3): 247-6). For instance, tumor cells are generally more sensitive to apoptosis induction by microtubule poisons such as taxol and DNA-damaging drugs such as doxorubicin, than healthy cells (Abal, et al. (2003) Curr. Cancer Drug Targets 3(3): 193-203).

However, in many types of cancer, levels of certain members of the anti-apoptotic Bcl-2 family proteins are elevated which causes cells to be less responsive to such drugs. This is especially true in B-cell lymphomas and other hematological malignancies. In these cancers elevated levels of anti-apoptotic Bcl-2 family proteins correlate highly with the onset of disease, maintenance of the disease state, and chemoresistance (Kitada et al. (2002) supra).

However, it was reported that cells over-expressing Bcl-xL exhibited increased sensitivity to an antimycin-A derivative compound that binds to and inhibits Bcl-2 and Bcl-xL (Manion, et al. (2004) J. Biol. Chem. 279(3): 2159-65; Kim, et al. (2001) Biochemistry 40: 4911-22). This finding has implications for the use of certain BH3 mimics as anti-tumor therapeutic compounds given that over-expression of Bcl-xL or Bcl-2 results in a general decrease in responsiveness to apoptotic cues and has been implicated in multi-drug resistance in cancer cells and carcinogenesis.

An understanding of the mechanisms for this observed change in response to Bcl-2 or Bcl-xL targeted compounds has been described (Letai, (2005) J. Clin. Invest. 115: 2648-55). In that report it was argued that the cell context in which elevated anti-apoptotic Bcl-2 proteins are found determines the occurrence or the degree of "sensitization" to apoptotic cues. Most notably, it is the presence of BH3-only proteins bound to these anti-apoptotic proteins that cause sensitization to apoptotic cues. For instance, the presence of the BH3-only protein Bad (Bcl-2 associated death promoter) bound to Bcl-2 or Bcl-xL sensitizes rather than kills cells, as is the case when the BH3-only protein Bim (Bcl-2-like 11) binds (Letai, et al. (2002) Cancer Cell 2(3): 183-92). Other arguments have been put forth that describe "hyper-dependence" on certain elevated anti-apoptotic Bcl-2 proteins in certain tumor cells (Kim, et al. (2001) Biochemistry 40: 4911-22).

The functions that the individual Bcl-2 family proteins have during hematopoiesis have been demarcated genetically using transgenic mice. For example, mice deficient in Bcl-2 have no overt problems during lymphocyte differentiation but do have excess apoptosis in peripheral lymphocytes after antigenic stimuli (Veis, et al. (1993) Cell 75: 229). Bcl-xL deficient mice are also viable but do show late maturation of erythroid cells (Wagner, et al. (2000) Development 127: 4949-58).

Mcl-1 deficiency has a pronounced, perhaps principal role in lymphocyte survival. Conditional knockouts have been used to determine the role of Mcl-1 in hematopoiesis and lymphocyte survival. Conditional deficiency of Mcl-1 results in apoptosis of differentiating lymphocytes and stops development of pre-B-cell and double negative T-cells as well as apoptosis in mature B and T lymphocytes (Rinkenberger, et al. (2000) Genes Dev. 14: 23). Thus the anti-apoptotic form of Mcl-1 plays a role in the development and survival of B and T lymphocytes, and may be an ideal target for treating excess growth of lymphoid cells.

The clinical implication is underscored by the observation that elevated Mcl-1 expressed in its active anti-apoptotic full length form positively correlates with increasing grade of B-cell lymphomas and plasma cell myelomas (Cho-Vega, et al. (2004) Hum. Pathol. 35 (9): 1095-100) as well as chronic lymphocytic leukemia (Petlickovski, et al. (2005) Blood 105: 4820-28).

Targeted gene knockouts for different pro-apoptotic BH3-only members of the Bcl-2 family members have been assessed for disease correlation. Transgenic mice deficient in Bim have extensive myeloid proliferation and autoreactive T and B cells that have lost responsiveness to apoptosis inducing drugs (Bouillet, et al. (1999) Science 286: 1735-38), while mice deficient in Bad display high incidence of diffuse large cell lymphoma (Ranger, et al. (2003) Proc. Natl. Acad. Sci. USA 100: 9324-29). Mice deficient in the pro-apoptotic BH3-only protein Bid demonstrated Hepatocarcinoma and a failure to respond to the death inducing cytokine fas (Yin, et al. (1999) Nature 400: 886-891). Both of the pro-apoptotic BH3-only proteins Puma and Noxa were shown to be required for all p53-mediated apoptosis (Villunger, et al. (2003) Science 302: 1036-1040).

Notably, conditional knockouts of the Mcl-1 gene caused profound reduction in B and T lymphocytes (Opferman, et al. (2003) Nature 426(6967): 671-6), which is the opposite of a deficiency in the BH3-only protein Bim and in keeping with the understanding that Mcl-1 selectively inhibits the pro-apoptotic protein Bim.

B. Combination Therapy

Embodiments of the present invention also include the combination of one or more compounds of Formula I and Formula II with other anti-tumor agents, such as proteasome inhibitors, to yield combination therapies. In some instances, these combination therapies may yield synergistic results as compared to the additive results of the component therapies when used alone. For example, these compounds may be particularly effective when used in combination with a class of therapeutics known as 26S proteasome inhibitors.

Compounds that have activity as 26S proteasome inhibitors have been suggested for use as anti-tumor therapeutics based on their ability to inhibit NF-κB signaling (Li, et al. (1995) Biophys. Biochem. Res. Corn. 215: 292-301). One such compound, the FDA approved drug Bortezomib (Velcade®), has been shown to cause elevated Mcl-1 in lymphocytes (Nencioni, et al. (2005) Blood 105(8): 3255-62). Elevated Mcl-1 has been shown to be causal in the establishment and maintenance of lymphoid and myeloid tumors. Unwanted side effect of elevated Mcl-1 can be rectified by inhibiting Mcl-1 using the compounds of Formula I or Formula II, and that these compounds will have utility in potentiating the effect of Bortezomib or other 26S proteasome inhibitors as anti-tumor therapeutics.

Proteasome inhibitors exhibit anti-tumor activity against malignancies of different histology. The rationale for looking at proteasome inhibitors as cancer therapeutics comes from the understanding that NF-kB is blocked by IkB which, following phosphorylation and ubiquination, is degraded in the 26S proteasome (Li, et al. (1995) supra). Following the degradation of IkB, NF-kB translocates to the nucleus where it functions as a transcription factor. NF-kB activates transcription of growth-promoting genes such as the interleukins as well as anti-apoptosis protein IAP and Bcl-2 (Wang, (1998) Science 281: 1680-83; Fahy, (2005) Cancer Chemother. Pharmacol. 56(1): 46-54). Blocking the 26S proteasome and degradation of Iκ-B then becomes an approach for inhibiting the growth-promoting and anti-apoptotic effects of NF-κB.

Empirical findings have indicated that actively proliferating cells are more sensitive to proteasome blockade than quiescent cells. For example human chronic lymphocytic leukemia (CLL) cells are much more sensitive to the proteasome inhibitor lactacystin than are normal lymphocytes. (Masdehors, et al. (1999) Br. J. Haematol. 105: 752-57). Oral squamous carcinoma cells are also more sensitive to lactacystin than normal oral epithelial cells (Kudo, et al. (2000) Clin. Cancer Res. 6: 916-923). The proteasome inhibitor Bortezomib or PS-341 or Velcade® (Hideshima, et al. (2001) Cancer Res. 61: 3071-76) has a more pronounced effect on human multiple myeloma compared to peripheral-blood mononuclear cells. Another proteasome inhibitor MG-132 demonstrates preferential killing of acute mylogenous leukemia (AML) cells over normal CD34+ cells (Guzman, et al. (2002) Proc. Natl. Acad. Sci. 99: 16220-25). Currently, the MG-132 compound is in pre-clinical studies while MLN-519, a lactacystin synthetic derivative, in phase 1 clinical trials. The therapeutic Bortezomib (Velcade®; Millennium Pharmaceuticals, and Johnson & Johnson Pharmaceutical Research & Development) has been approved for use in treatment of multiple myeloma. Introduced in the U.S. in 2003, Velcade provides an improvement in MM therapy, and is approved as a first line therapy in combination with oral melphalan and prednisone. Velcade is now widely prescribed in combination with dexamethasone (Doxil, Adriamycin) or with dexamethasone and the thalidamide drugs Revlicade (lenolidomide) and Thalidomid (thalidomide), the so-called RVD treatment.

Recent evidence indicates that some anti-apoptotic factors accumulate as a consequence of exposure to Bortezomib (Velcade®), possibly reducing its effectiveness as an anti cancer therapeutic. Most notably the Bcl-2 family member Mcl-1 is elevated in cells treated with Bortezomib (Velcade®) (Nencioni, et al. (2005) Blood 105(8): 3255-62). This is problematic as the proteasome-mediated reduction of Mcl-1 is an initiating signal for apoptosis in response to genotoxic stimuli (Cuconati, et al. (2003) Genes Dev. 17(23): 2922-32) and antigen receptor signaling in B-cells (Petlickovsky, et al. (2005) Blood 105(12): 4820-7). Further, sustained signaling through the B-cell receptor induces Mcl-1 and promotes survival of chronic lymphocytic leukemia B cells (Petlickovsky, et al. (2005) supra).

These observations suggest that elevated Mcl-1 may counteract Bortezomib (Velcade®) in CLL, AML and certain NHL cells. Consistent with this, the cytotoxic effects of proteasome inhibitors are enhanced when Mcl-1 levels are contained at normal levels or reduced in a cell culture (Nencioni, et al. (2005) supra). This finding demonstrated that Mcl-1 accumulation is an unwanted molecular consequence of exposure to proteasome inhibitors.

C. Screening Methods

The present invention also teaches a method for selecting appropriate BH3 mimic compounds in treating particular tumors. This selection is based on an understanding of the unique activity of compounds of Formula I and Formula II to mimic particular BH3 domains. Compounds from this group that have unique activity against either all of the anti-apoptotic Bcl-2 family proteins or a particular member of this family of proteins are useful against particular tumors. Expression levels of particular Bcl-2 family proteins can be assessed using standard assays, such as western blot or immunohistological staining of biopsied tumor tissue. Following this assessment, compounds with activity against the elevated proteins in the tumor sample will be selected as an appropriate therapeutic for treating that tumor.

It is of particular interest to establish the correlation of Mcl-1 expression levels to the occurrence of tumors. Based on the discovery that compounds of Formula I and Formula II inhibit Mcl-1 binding (see Example 1, below), it may be that cells that are hyper-dependent on Mcl-1, as a consequence of elevated Mcl-1 in the disease state, will be sensitized to compounds of Formula I and Formula II or other derivative BH3 mimic compounds that are shown to inhibit Mcl-1.

BH3 mimic compounds that do inhibit Mcl-1 will become important second line therapy for CLL given that tumor cells from patients who relapse from the current front line therapy Rituxan display high Mcl-1 to Bax ratio. (Bannerji, et al. (2003) J. Clin. Oncol. 21(8): 1466-71). Inhibition of Mcl-1 activity by a compound of Formula I or Formula II, or other BH3 mimic compounds will qualify those compounds as front line therapeutics against MM, CLL, AML, ALL, and NHL as well as prostate, liver, and ovarian cancers and other malignancies that are affected by elevated Mcl-1.

There is a clear indication that elevated expression of anti-apoptotic Bcl-2 family proteins is often the cause of chemoresistance (Kostanova-Poliakova, et al. (2005) Neoplasma 52(6): 441-9). Therefore, it will also be important to know which of the Bcl-2 family proteins are involved in chemoresistance when considering second line treatment for relapsed patients.

The present invention also teaches a method for determining selective activity of a BH3 mimic compound against the Bcl-2 family proteins. This method also uses this information to predict efficacy of a selective BH3 mimic compound in treating certain hematological malignancies that are defined by expression levels of Bcl-2 family proteins. Specific activity against such disease-profiled Bcl-2 family proteins is predicted to have the best anti-tumor activity and lowest toxicity against the non-tumor cells in the treated organism.

For instance, one skilled in the art can compare the blocking activity of BH3 mimic compounds to particular BH3 domain-containing peptides. The activity is the ability to block binding of certain BH3 domain-containing Bcl-2 proteins. To do this, BH3 mimic compounds and particular BH3-containing peptides are assessed for patterns of activity in inhibiting particular BH3 mediated protein/protein interactions. Patterns of activity are charted and an algorithm is used to determine overlap between the activity of certain BH3 peptides and certain BH3 mimic compounds. The ability to mimic particular BH3 domains is determined.

A compound that mimics a BH3 domain of a particular Bcl-2 family protein with a given physiological role will replicate the role of that particular BH3-containing protein. In a disease state where that protein is known to have impaired function, the compound would replace that particular function.

The acquired understanding enables one skilled in the art to predict the efficacy of a given BH3 mimic compound in a given disease tissue type by recognizing the protein with the most pronounced role in affecting the disease state. This prediction is based on the understanding of the role that a sub-set of Bcl-2 family protein interactions or one particular protein from this family plays in that tissue type and in the tissue specific disease.

Recent work has described unique functions of BH3-only proteins in affecting apoptosis. For instance, the BH3-only protein Bad, has been identified as having a "sensitizing" function compared to the BH3 protein Bid which has an "effector" function in causing cell death (Letai, (2005) J. Clin. Invest. 115: 2648-2655). Additionally, BH3-only proteins have distinct roles in maintaining the healthy organism. For instance, the BH3-only protein Bim is required for thymocyte killing in response to negative selection signals. Bim function is essential for the maintenance of the healthy thymocyte population. Bim recognizes cues such as cytoskeletal abnormalities while binding to the microtubule-associated dynein motor complex (Puthalakath, et al. (1999) Mol Cell. 3(3): 287-96). The sensing mechanism and the role that this BH3 protein plays are unique among all of the other BH3-only proteins.

BH3-only proteins have distinct roles in targeting particular members of the multi-domain Bcl-2 protein. The binding specificity of the various BH3 domains to particular multi-domain Bcl-2 family proteins can affect disease outcome. An example is the BH3-only protein Noxa that is highly selective for binding to Mcl-1 and not other Bcl-2 family proteins (Chen, et al. (2005) Mol Cell. 17(3): 393-403). The pro-apoptotic protein Bak is activated through Noxa-dependent displacement from Mcl-1 (Willis, et al. (2005) Genes & Dev. 19(11): 1294-305). Noxa becomes a more significant death effector protein in the context of a high Mcl-1 background, such as in lymphocytes and myeloid cells under certain conditions. Aberrant control of these interactions leads to lymphomagenesis and myeloid cancer.

The BH3-only protein Puma is up-regulated by the oncogene p53 and is strongly implicated in lymphomagenesis (Hemann, et al. (2004) Proc. Natl. Acad. Sci. USA 101: 9333-38). Deficiency in p53 activity causes tumor formation. Expression of Puma in certain lymphoid cell background suppresses such p53 deficiency mediated tumorigenesis (Hemann, et al. (2004) Proc. Natl. Acad. Sci. USA 101: 9333-38).

The invention teaches that selection of a BH3 mimic compound that matches the binding inhibition activity pattern of the Noxa BH3 domain peptide will result in a Noxa BH3 specific mimic. This compound will then be useful in affecting diseases that involve the Noxa-Mcl-1 interaction. These disease indications that would be served by such a compound/therapeutic include NHL, CLL, AML and ALL. A BH3 mimic compound that selectively mimics the Puma BH3 domain would suppress tumors resulting from certain types of p53 deficiency by restoring deficient response to DNA damage-mediated apoptotic signals. A Bim BH3 mimic compound is predicted to have selective efficacy against T-cells that have lost responsiveness to negative selection as happens in certain autoimmune disease or thymocyte malignancies. Such a BH3 mimic would provide an effective anti-autoimmune disease therapeutic for treatment of diseases such as Type I diabetes, rheumatoid arthritis, multiple sclerosis, myasthenia gravis, psoriasis, lupus, inflammatory bowel disease, and other diseases.

Also contemplated is the exploitation of unique features of the BH3-only protein Bad. Bad has been described as a sensitizing BH3 protein, unlike Bid or Bim that are effector BH3 proteins, capable of directly activating Bax or Bak and killing cells. It is therefore, likely that mimetic compounds that selectively mimic Bad may have less toxicity than that which mimics the BH3 protein Bid and therefore will be well suited as a general anti-tumor therapeutic.

The invention also teaches a method for recognizing small molecules that function to mimic distinct members of the BH3 domain containing family of proteins and in doing so, recognize small molecules more likely to become effective drug candidates.

D. Administration and Dosage
  i. Routes of Administration

A compound of Formula I or Formula II can be administered by any known administration method known to a person skilled in the art. Examples of routes of administration include but are not limited to oral, parenteral, intraperitoneal, intravenous, intraarterial, transdermal, topical, sublingual, intramuscular, rectal, transbuccal, intranasal, liposomal, via inhalation, vaginal, intraoccular, via local delivery by catheter or stent, subcutaneous, intraadiposal, intraarticular, intrathecal, or in a controlled or extended release dosage form. A compound of Formula I or Formula II can be administered in accordance with any dose and dosing schedule that achieves a dose effective to treat disease.

The route of administration of a compound of Formula I or Formula II can be independent of the route of administration of any additional anti-cancer agents that are used. Either at least one of the compounds of Formula I or Formula II or another compound can be administered, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a controlled or extended release dosage form.

For example, a compound of the invention can be administered in oral forms, for example, as tablets, capsules (each of which includes sustained release or timed release formulations), pills, powders, granules, elixirs, tinctures, suspensions, syrups, and emulsions. Likewise, a compound can be administered by intravenous (e.g., bolus or infusion), intraperitoneal, subcutaneous, intramuscular, or other routes using forms well known to those of ordinary skill in the pharmaceutical arts. Particularly useful routes of administration of a compound are oral administration and intravenous delivery.

A compound can also be administered in the form of a depot injection or implant preparation, which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

A compound can also be administered in the form of liposome delivery systems, such as small unilamellar vesicles, large unilamellar vesicles and multilamellar vesicles. Liposomes can be formed from a variety of phospholipids, such as cholesterol, stearylamine, or phosphatidylcholines. Liposome versions of a compound may be used to increase tolerance to the agents.

A compound can also be delivered by the use of monoclonal antibodies as individual carriers to which the compound molecules are coupled.

A compound can also be prepared with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, a compound can be prepared with biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

In a specific embodiment, a compound can be administered orally in a gelatin capsule, which can comprise excipients such as microcrystalline cellulose, croscarmellose sodium and magnesium stearate. For example, an embodiment can include 200 mg of solid compound with 89.5 mg of microcrystalline cellulose, 9 mg of sodium croscarmellose, and 1.5 mg of magnesium stearate contained in a gelatin capsule.

ii. Dosages and Dosage Schedules

The dosage regimen utilizing a compound of Formula I or Formula II can be selected in accordance with a variety of factors including type, species, age, weight, and sex of the patient; the type of disease being treated; the severity (e.g., stage) of the disease to be treated; the route of administration; the renal and hepatic function of the patient; and the particular compound or salt thereof employed, among others. A dosage regimen can be used, for example, to prevent, inhibit (fully or partially), or arrest the progress of the disease.

In accordance with the invention, a compound of Formula I or Formula II can be administered by continuous or intermittent dosages. For example, intermittent administration of a compound of Formula I or Formula II may be administered one to six days per week or it may be administered in cycles with rest periods in between the cycles (e.g., daily administration for two to eight consecutive weeks, then a rest period with no administration for up to one week between treatments) or it may be administered on alternate days.

For example, in one embodiment, a compound of Formula I or Formula II can be administered in a total daily dose of up to 800 mg. A compound of Formula I or Formula II can be administered once daily (QD), or divided into multiple daily doses such as twice daily (BID), and three times daily (TID). A compound of Formula I or Formula II, can be administered at a total daily dosage of up to 800 mg, for example, about 200 mg, 300 mg, 400 mg, 600 mg, or 800 mg, which can be administered in one daily dose or can be divided into multiple daily doses as described above. In specific aspects, the administration is oral or by intravenous delivery.

In one embodiment, the compound is administered once daily at a dose of about 200-600 mg. In another embodiment, the compound is administered twice daily at a dose of about 200-400 mg. In another embodiment, the compound is administered twice daily at a dose of about 200-400 mg intermittently, for example three, four or five days per week. In one embodiment, the daily dose is about 200 mg which can be administered once-daily, twice-daily or three-times daily. In one embodiment, the daily dose is about 300 mg which can be administered once-daily, twice-daily or three-times daily. In one embodiment, the daily dose is about 400 mg which can be administered once-daily, twice-daily or three-times daily.

A compound of Formula I or Formula II, can be administered in accordance with any dose and dosing schedule that achieves a dose effective to treat cancer. Each compound can be administered in a total daily dose that may vary from patient to patient, and may be administered at varying dosage schedules. For example, a compound of the invention can be administered to the patient at a total daily dosage of between 25-4000 mg/m$^2$. In particular, a compound of Formula I or Formula II can be administered in a total daily dose of up to 800 mg, including by oral or intravenous administration, once, twice or three times daily, continuously (every day) or intermittently (e.g., 3-5 days a week). In addition, the administration can be continuous, e.g., every day, or intermittently.

In addition, a compound of Formula I or Formula II may be administered according to any of the schedules described above, consecutively for a few weeks, followed by a rest period.

In one embodiment, the patient can receive intravenously or subcutaneously compounds of Formula I or Formula II in quantities sufficient to deliver between about 3-1500 mg/m$^2$ per day, for example, about 3, 30, 60, 90, 180, 300, 600, 900, 1200 or 1500 mg/m$^2$ per day. Such quantities may be administered in a number of suitable ways, e.g. large volumes of low concentrations of the compounds of Formula I or Formula II can be used during one extended period of time or several times a day. The quantities can be administered for one or more consecutive days, intermittent days or a combination thereof per week (7 day period). Alternatively, low volumes of high concentrations of the compounds of Formula I or Formula II can be used during a short period of time, e.g. once a day for one or more days either consecutively, intermittently or a combination thereof per week (7 day period). For example, a dose of 300 mg/m$^2$ per day can be administered for 5 consecutive days for a total of about 1500 mg/m$^2$ per treatment. In another dosing regimen, the number of consecutive days can also be 5, with treatment lasting for 2 or 3 consecutive weeks for a total of about 3000 mg/m$^2$ or about 4500 mg/m$^2$ total treatment.

Typically, an intravenous formulation may be prepared which contains a concentration of a compound of Formula I or Formula II of between about 1.0 mg/mL to about 10 mg/mL, e.g. about 2.0 mg/mL, 3.0 mg/mL, 4.0 mg/mL, 5.0 mg/mL, 6.0 mg/mL, 7.0 mg/mL, 8.0 mg/mL, 9.0 mg/mL and 10 mg/mL and administered in amounts to achieve the doses described above. In one example, a sufficient volume of intravenous formulation can be administered to a patient in a day such that the total dose for the day is between about 300 and about 1500 mg/m$^2$.

Subcutaneous formulations can be prepared according to procedures well known in the art at a pH in the range between about 5 and about 12, which include suitable buffers and are tonicity agents, as described below. They can be formulated to deliver a daily dose of any of compounds of Formula I or Formula II in one or more daily subcutaneous administrations, for example, one, two or three times each day.

It is apparent to a person skilled in the art that any one or more of the specific dosages and dosage schedules of a compound of Formula I or Formula II are also applicable to any one or more of the anti-cancer agents to be used in a combination treatment. Moreover, the specific dosage and dosage schedule of a compound of Formula I or Formula II can further vary, and the optimal dose, dosing schedule, and route of administration can be determined based upon the specific drug combination that is being used. Further, the various modes of administration, dosages, and dosing schedules described herein merely set forth specific embodiments and should not be construed as limiting the broad scope of the invention. Any permutations, variations, and combinations of the dosages and dosing schedules are included within the scope of the present invention.

iii. Formulation

An "effective amount" of a compound of Formula I or Formula II is the quantity which, when administered to a subject having a disease or disorder, results in regression of the disease or disorder in the subject. Thus, an effective amount of a compound of the disclosed invention is the quantity which, when administered to a subject having a cell proliferation disorder, results in, for example, regression of cell growth or cell death in a subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present invention effective when administered alone or in combination as an anti-proliferative agent. For example, an effective amount refers to an amount of the compound present in a formulation or on a medical device given to a recipient patient or subject sufficient to elicit biological activity, for example, anti-proliferative activity, such as for example, anti-cancer activity or anti-neoplastic activity. The combination of compounds optionally is a synergistic combination. Synergy, as described, for example, by Chou and Talalay, (1984) Adv. Enzyme Regul. 22: 27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, or increased anti-proliferative effect, or some other beneficial effect of the combination compared with the individual components.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A therapeutically effective amount of one or more of a compound can be formulated with a pharmaceutically acceptable carrier for administration to a human or an animal. Accordingly, a compound or a formulation can be administered, for example, via oral, parenteral, or topical routes, to provide an effective amount of the compound. In alternative embodiments, a compound is prepared in accordance with the present invention can be used to coat or impregnate a medical device, e.g., a stent.

The term "prophylactically effective amount" means an effective amount of a compound or compounds, of the present invention that is administered to prevent or reduce the risk of unwanted cellular proliferation.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

A "pharmaceutical composition" is a formulation containing a compound of Formula I or Formula II in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" can include both one and more than one such excipient.

A compound of Formula I or Formula II is capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacctic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of a compound of Formula I or Formula II can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile may be used. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxyl amine-containing and imine-containing compounds of the present invention.

A compound of Formula I or Formula II can also be prepared as esters, for example pharmaceutically acceptable esters. For example a carboxylic acid functional group in a compound can be converted to its corresponding ester, e.g., a methyl, ethyl, or other ester. Also, an alcohol group in a compound can be converted to its corresponding ester, e.g., an acetate, propionate, or other ester.

A compound of Formula I or Formula II can also be prepared as prodrugs, for example pharmaceutically acceptable prodrugs. The terms "pro-drug" and "prodrug" are used interchangeably herein and refer to any compound that releases an active parent drug in vivo. Since prodrugs are known to enhance numerous desirable qualities of pharmaceuticals (e.g., solubility, bioavailability, manufacturing, etc.) a compound of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxyl, amino, sulfhydryl, carboxyl, or carbonyl group is bonded to any group that may be cleaved in vivo to form a free hydroxyl, free amino, free sulfhydryl, free carboxyl or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxyl functional groups, ester groups (e.g. ethyl esters, morpholinocthanol esters) of carboxyl functional groups, N-acyl derivatives (e.g. N-acetyl), N-Mannich bases, Schiff bases and enaminones of amino functional groups, oximes, acetals, ketals and enol esters of ketone and aldehyde functional groups in compounds of the invention including compounds of Formula I or Formula II or derivatives, and the like, (see, Bundegaard, "Design of Prodrugs" pgs. 1-92, Elesevier, New York-Oxford (1985)).

All percentages and ratios used herein, unless otherwise indicated, are by weight.

"Combination therapy" (or "co-therapy") includes the administration of a compound of Formula I or Formula II and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks, depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

A compound of Formula I or Formula II, or pharmaceutically acceptable salts thereof, can be administered orally, nasally, transdermally, pulmonary, inhalationally, buccally, sublingually, intraperintoneally, subcutaneously, intramuscularly, intravenously, rectally, intrapleurally, intrathecally and parenterally. In certain embodiments, the compound is administered orally. One skilled in the art will recognize the advantages of certain routes of administration.

The dosage regimen utilizing the a compound is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ ed., Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one embodiment, a compound of Formula I or Formula II are prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, a compound of Formula I or Formula II or salts, solvates, tautomers or polymorphs thereof, can be combined with sterile aqueous or organic media to form injectable solutions or suspensions. Injectable compositions may be aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, or about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, or about 1 to 50%, of the active ingredient.

In some embodiments, a compound of Formula I or Formula II is formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, for example, typically less than about five minutes, less than about ninety seconds, less than about thirty seconds and less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

A compound of Formula I or Formula II can also be also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, for example, liquid formulations, including cyclic or acyclic encapsulating or solvating agents, for example, cyclodextrins, polyethers, or polysaccharides (e.g., methylcellulose), or polyanionic α-cyclodextrin derivatives with a sodium sulfonate salt group separate from the lipophilic cavity by an alkyl ether spacer group or polysaccharides. In one embodiment, the agent can be polyanionic cyclodextrin derivative with a sodium sulfonate salt separated from the lipophilic cavity by a butyl ether spacer group, e.g., CAPTISOL® (CyDex, Overland, and KS). One skilled in the art can evaluate suitable agent/disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

The invention is illustrated in the examples that follow. This section is set forth to aid in an understanding of the invention but is not intended to, and should not be construed to limit in any way the invention as set forth in the claims which follow thereafter.

METHODS OF MAKING

Examples of synthetic pathways useful for making compounds described herein are set forth in Schemes 1-6.

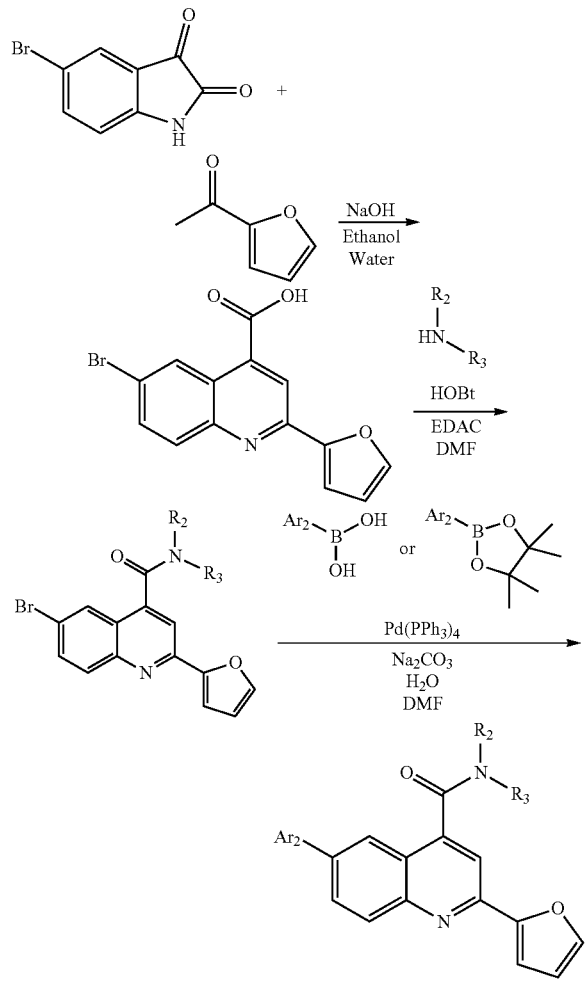

Preparation of 2-(furan-2-yl)-6-phenyl-N-(pyridin-3-yl)quinoline-4-carboxamide (1)

The title compound was prepared using the methods shown in Scheme 1 with the appropriate amine (3-pyridylamine) and boronic acid (phenylboronic acid) reagents.

To a 500 ml three necked round bottom flask was added 5-bromoisatin (20 g) and 2-acetyl-furan (9.7 g) in ethanol (150 ml) followed by NaOH (9.2 g) in one lot and the resulting brown solution was allowed to stir at RT for 5 minutes. To the above reaction mixture was added water (5 ml) at RT and the reaction mixture was heated to reflux for 2 hours. The completion of the reaction was monitored on TLC using MDC:MeOH (9:1) as a mobile phase. After completion of the reaction, the reaction mixture was filtered hot and water (150 ml) was added to filtrate. The filtrate was then acidified with 5N HCl to pH 6.0-6.5 and the precipitate formed was filtered and washed with water (3*50 ml) followed by ethanol (2*10 ml) to yield 6-bromo-2-(furan-2-yl)quinoline-4-carboxylic acid (20 g).

To a 250 ml three necked round bottom flask equipped with thermo pocket under argon atmosphere was added 6-bromo-2-(furan-2-yl)quinoline-4-carboxylic acid (5 g) in DMF (15 ml). The solution was stirred for 5 minutes. After 5 minutes, EDAC.HCl (N-(3-dimethylaminopropyl)-N-ethylcarbodiimide hydrochloride) (3.6 g), HOBT (2.54 g) and DMAP (3.83 g) were added at RT and the reaction mixture was stirred at room temperature for 0.5 h. 3-amino pyridine (1.6 g) was then added in one lot and the reaction was allowed to stir at RT for 12 hours. The completion of the reaction was monitored by TLC using ethyl acetate:hexanes (5:5) as a mobile phase. After completion of the reaction, the reaction mixture was diluted with ethyl acetate (100 ml) and then washed with water (5×100 ml). The ethyl acetate layer was dried over anhydrous sodium sulphate and then solvent was distilled out and the crude was subjected to purification by silica gel column chromatography, eluting with 1.5% methanol in methylene chloride to provide 6-bromo-2-(furan-2-yl)-N-(pyridin-3-yl)quinoline-4-carboxamide (2.0 g).

To a sealed tube under argon atmosphere was added 6-bromo-2-(furan-2-yl)-N-(pyridin-3-yl)quinoline-4-carboxamide (0.250 g) in DMF (5 ml), and the vessel was purged with argon under stirring for 5 minutes. After 5 minutes, 2N solution of sodium carbonate in water (3.3 ml) was added and the tube was purged with argon under stirring for 5 minutes. Phenylboronic acid (0.115 g) was then added and the tube was purged with argon under stirring for 15 minutes. Finally, palladium(0)tetrakis triphenylphosphine (0.034 g) was added under argon and the tube was sealed and heated to 90° C. for 16 hours. The completion of the reaction was monitored by TLC using ethyl acetate:hexanes (5:5) as a mobile phase. After completion of the reaction, the reaction mixture was diluted with ethyl acetate (100 ml) and then washed with water (5*100 ml). The ethyl acetate layer was dried over anhydrous sodium sulphate, and the solvent was removed by distillation and the crude product was subjected to purification by silica gel column chromatography, eluting with 1-2% methanol in methylene chloride to provide 0.154 g of 2-(furan-2-yl)-6-phenyl-N-(pyridin-3-yl)quinoline-4-carboxamide (1). $^1$H NMR (400 MHz, DMSO-$d_6$) δ ppm 11.13 (s, 1H), 8.59 (m, 1H), 8.39 (m, 1H), 8.37 (s, 1H), 8.30 (m, 1H), 8.25 (s, 1H), 8.19 (m, 2H), 8.02 (s, 1H), 7.79 (m, 2H), 7.55 (m, 3H), 7.46 (m, 2H), 6.79 (m, 1H); m/z 392.2 (MH$^+$).

Preparation of 2-(furan-2-yl)-6-(1H-pyrazol-4-yl)-N-(pyridin-3-yl)quinoline-4-carboxamide (2)

The title compound was prepared using the methods shown in Scheme 1 with the appropriate amine (3-pyridylamine) and boronic acid ((1H-pyrazol-4-yl)boronic acid) reagents.

Preparation of 6-(2-fluorophenyl)-2-(furan-2-yl)-N-(pyridin-3-yl)quinoline-4-carboxamide (3)

The title compound was prepared using the methods shown in Scheme 1 with the appropriate amine (3-pyridylamine) and boronic acid ((2-fluorophenyl)boronic acid) reagents.

Preparation of 6-(3-fluorophenyl)-2-(furan-2-yl)-N-(pyridin-3-yl)quinoline-4-carboxamide (4)

The title compound was prepared using the methods shown in Scheme 1 with the appropriate amine (3-pyridylamine) and boronic acid ((3-fluorophenyl)boronic acid) reagents.

Preparation of 6-(4-fluorophenyl)-2-(furan-2-yl)-N-(pyridin-3-yl)quinoline-4-carboxamide (5)

The title compound was prepared using the methods shown in Scheme 1 with the appropriate amine (3-pyridylamine) and boronic acid ((4-fluorophenyl)boronic acid) reagents.

Preparation of 2-(furan-2-yl)-6-(3-methoxyphenyl)-N-(pyridin-3-yl)quinoline-4-carboxamide (6)

The title compound was prepared using the methods shown in Scheme 1 with the appropriate amine (3-pyridylamine) and boronic acid ((3-methoxyphenyl)boronic acid) reagents.

Preparation of 2-(furan-2-yl)-6-(4-methoxyphenyl)-N-(pyridin-3-yl)quinoline-4-carboxamide (7)

The title compound was prepared using the methods shown in Scheme 1 with the appropriate amine (3-pyridylamine) and boronic acid ((4-methoxyphenyl)boronic acid) reagents.

Preparation of 6-([1,1'-biphenyl]-4-yl)-2-(furan-2-yl)-N-(pyridin-3-yl)quinoline-4-carboxamide (8)

The title compound was prepared using the methods shown in Scheme 1 with the appropriate amine (3-pyridylamine) and boronic acid ([1,1'-biphenyl]-4-ylboronic acid) reagents. $^1$H NMR (400 MHz, DMSO-$d_6$) δ ppm 9.85 (s, 1H), 7.70 (s, 1H), 7.15 (m, 1H), 7.12 (m, 1H), 7.03 (m, 1H), 6.97 (s, 1H), 6.95 (m, 1H), 6.94 (m, 1H), 6.74 (m, 1H), 6.62 (m, 2H), 6.55 (m, 2H), 6.46 (m, 2H), 6.25 (m, 2H), 6.21 (m, 2H), 6.12 (m, 1H), 5.51 (m, 1H); m/z 468.3 (MH$^+$).

Preparation of 6-([1,1'-biphenyl]-3-yl)-2-(furan-2-yl)-N-(pyridin-3-yl)quinoline-4-carboxamide (9)

The title compound was prepared using the methods shown in Scheme 1 with the appropriate amine (3-pyridylamine) and boronic acid ([1,1'-biphenyl]-3-ylboronic acid) reagents. $^1$H NMR (400 MHz, DMSO-$d_6$) δ ppm 11.13 (s, 1H), 8.97 (m, 1H), 8.44 (m, 1H), 8.39 (m, 1H), 8.30 (m, 3H), 8.26 (s, 1H), 8.21 (m, 1H), 8.01 (m, 2H), 7.77 (m, 2H), 7.72 (m, 1H), 7.62 (m, 1H), 7.46-7.54 (m, 4H), 7.42 (m, 1H), 6.80 (s, 1H); m/z 468.4 (MH$^+$).

Preparation of 2-(furan-2-yl)-6-(3-(2-methoxyethoxyl)phenyl)-N-(pyridin-3-yl)quinoline-4-carboxamide (10)

The title compound was prepared using the methods shown in Scheme 1 with the appropriate amine (3-pyridylamine) and boronic acid ((3-(2-methoxyethoxyl)phenyl)boronic acid) reagents. $^1$H NMR (400 MHz, DMSO-$d_6$) δ ppm 11.12 (s, 1H), 8.97 (m, 1H), 8.39 (m, 2H), 8.29 (m, 1H), 8.24 (s, 1H), 8.18 (m, 2H), 8.02 (s, 1H), 7.53 (m, 1H), 7.45 (m, 2H), 7.33 (m, 2H), 7.012 (m, 1H), 6.80 (broad s, 1H), 4.19 (m, 2H), 3.67 (m, 2H), 3.32 (s, 3H); m/z 466.0 (MH$^+$).

Preparation of 2-(furan-2-yl)-6-(4-(2-methoxyethoxyl)phenyl)-N-(pyridin-3-yl)quinoline-4-carboxamide (11)

The title compound was prepared using the methods shown in Scheme 1 with the appropriate amine (3-pyridylamine) and boronic acid ((4-(2-methoxyethoxyl)phenyl)boronic acid) reagents. $^1$H NMR (400 MHz, DMSO-$d_6$) δ ppm 11.11 (s, 1H), 8.97 (m, 1H), 8.40 (m, 1H), 8.30 (m, 2H), 8.22 (s, 1H), 8.15 (m, 2H), 8.01 (m, 1H), 7.73 (d, 1H), 7.49 (m, 2H), 7.10 (m, 2H), 6.78 (m, 1H), 4.15 (m, 2H), 3.69 (m, 2H), 3.33 (s, 3H); m/z 466.4 (MH$^+$).

Preparation of 2-(furan-2-yl)-6-(3-phenoxyphenyl)-N-(pyridin-3-yl)quinoline-4-carboxamide (12)

The title compound was prepared using the methods shown in Scheme 1 with the appropriate amine (3-pyridylamine) and boronic acid ((3-phenoxyphenyl)boronic acid) reagents. $^1$H NMR (400 MHz, DMSO-$d_6$) δ ppm 11.11 (s, 1H), 8.96 (s, 1H), 8.41 (m, 1H), 8.34 (m, 1H), 8.26 (m, 2H), 8.16 (m, 2H), 8.02 (s, 1H), 7.54 (m, 3H), 7.48 (m, 1H), 7.38 (m, 3H), 7.15 (m, 1H), 7.07 (m, 3H), 6.79 (broad s, 1H); m/z 484.3 (M$^{H+}$).

Preparation of 2-(furan-2-yl)-6-(4-phenoxyphenyl)-N-(pyridin-3-yl)quinoline-4-carboxamide (13)

The title compound was prepared using the methods shown in Scheme 1 with the appropriate amine (3-pyridylamine) and boronic acid ((4-phenoxyphenyl)boronic acid) reagents. $^1$H NMR (400 MHz, DMSO-$d_6$) δ ppm 11.12 (s, 1H), 8.97 (s, 1H), 8.35 (m, 2H), 8.25 (m, 2H), 8.17 (m, 2H), 8.02 (s, 1H), 7.81 (m, 2H), 7.48-7.67 (m, 4H), 7.09-7.19 (m, 5H), 6.79 (s, 1H); m/z 484.4 (MH$^+$).

Preparation of 2-(furan-2-yl)-N-(pyridin-3-yl)-6-(pyridin-4-yl)quinoline-4-carboxamide (14)

The title compound was prepared using the methods shown in Scheme 1 with the appropriate amine (3-pyridylamine) and boronic acid (pyridin-4-ylboronic acid) reagents to provide the target compound (0.012 g). $^1$H NMR (400 MHz, DMSO-$d_6$) δ ppm 11.15 (s, 1H), 8.98 (m, 1H), 8.70 (m, 2H), 8.53 (m, 1H), 8.40 (m, 1H), 8.29 (m, 2H), 8.25 (m, 2H), 8.04 (m, 1H), 7.83 (m, 2H), 7.57 (m, 1H), 7.48 (m, 1H), 6.81 (s, 1H); m/z 393.2 (MH$^+$).

Preparation of 2-(furan-2-yl)-6-(1H-indol-6-yl)-N-(pyridin-3-yl)quinoline-4-carboxamide (15)

The title compound was prepared using the methods shown in Scheme 1 with the appropriate amine (3-pyridylamine) and boronic acid ((1H-indol-6-yl)boronic acid) reagents to provide the target compound (0.020 g). $^1$H NMR (400 MHz, DMSO-$d_6$) δ ppm 11.24 (s, 1H), 11.14 (s, 1H), 8.99 (s, 1H), 8.39 (m, 2H), 8.30 (m, 2H), 8.23 (m, 2H), 8.18 (m, 1H), 8.01 (m, 1H), 7.78 (m, 1H), 7.67 (m, 1H), 7.51 (m, 1H), 7.47 (m, 1H), 7.44 (m, 1H), 7.42 (m, 1H), 6.79 (m, 1H), 6.48 (broad s, 1H); m/z 431.3 (MH$^+$).

Preparation of 2-(furan-2-yl)-6-(1-methyl-1H-benzo[d]imidazol-5-yl)-N-(pyridin-3-yl)quinoline-4-carboxamide (16)

The title compound was prepared using the methods shown in Scheme 1 with the appropriate amine (3-pyridylamine) and boronic acid ((1-methyl-1H-benzo[d]imidazol-5-yl)boronic acid) reagents to provide the target compound (0.014 g). $^1$H NMR (400 MHz, DMSO-$d_6$) δ ppm 11.14 (s, 1H), 8.97 (m, 1H), 8.40 (m, 2H), 8.31 (m, 1H), 8.28 (s, 1H), 8.26 (m, 1H), 8.25 (s, 1H), 8.19 (m, 1H), 8.05 (m, 2H), 7.72 (m, 2H), 7.53 (m, 1H), 7.48 (m, 1H), 6.79 (m, 1H), 3.89 (s, 3H); m/z 446.2 (MH$^+$).

Preparation of 2-(furan-2-yl)-6-(1H-indazol-5-yl)-N-(pyridin-3-yl)quinoline-4-carboxamide (17)

The title compound was prepared using the methods shown in Scheme 1 with the appropriate amine (3-pyridylamine) and boronic acid ((1H-indazol-5-yl)boronic acid) reagents to provide the target compound (0.012 g). $^1$H NMR (400 MHz, DMSO-d$_6$) δ ppm 13.20 (s, 1H), 11.14 (s, 1H), 8.98 (m, 1H), 8.40 (m, 2H), 8.30 (m, 1H), 8.26 (m, 1H), 8.25 (m, 2H), 8.20 (m, 2H), 8.03 (s, 1H), 7.79 (m, 1H), 7.68 (m, 1H), 7.53 (m, 1H), 7.47 (m, 1H), 6.79 (m, 1H); m/z 432.2 (MH$^+$).

Preparation of 6-(benzo[d]thiazol-5-yl)-2-(furan-2-yl)-N-(pyridin-3-yl)quinoline-4-carboxamide (18)

The title compound was prepared using the methods shown in Scheme 1 with the appropriate amine (3-pyridylamine) and boronic ester (5-(4,4,5,5-tetramethyl-1,3,2-dioxaborolan-2-yl)benzo[d]thiazole) reagents to provide the target compound (0.118 g). $^1$H NMR (400 MHz, DMSO-d$_6$) δ ppm 11.16 (s, 1H), 9.49 (s, 1H), 8.99 (s, 1H), 8.50 (m, 2H), 8.40 (m, 1H), 8.33 (m, 3H), 8.27 (s, 1H), 8.22 (m, 1H), 8.05 (m, 1H), 7.94 (m, 1H), 7.56 (m, 1H), 7.47 (m, 1H), 6.60 (m, 1H); m/z 449.1 (MH$^+$).

Preparation of 2-(furan-2-yl)-6-(naphthalen-2-yl)-N-(pyridin-3-yl)quinoline-4-carboxamide (19)

The title compound was prepared using the methods shown in Scheme 1 with the appropriate amine (3-pyridylamine) and boronic acid (naphthalen-2-ylboronic acid) reagents to provide the target compound (0.025 g). $^1$H NMR (400 MHz, DMSO-d$_6$) δ ppm 11.17 (s, 1H), 8.97 (s, 1H), 8.51 (s, 1H), 8.39 (m, 1H), 8.35 (m, 2H), 8.29 (m, 2H), 8.26 (m, 1H), 8.07 (m, 2H), 8.01 (s, 1H), 7.95 (m, 2H), 7.56 (m, 3H), 7.49 (m, 1H), 6.80 (s, 1H); m/z 442.3 (MH$^+$).

Preparation of 2-(furan-2-yl)-6-(1H-indol-3-yl)-N-(pyridin-3-yl)quinoline-4-carboxamide (20)

The title compound was prepared using the methods shown in Scheme 1 with the appropriate amine (3-pyridylamine) and boronic ester (tert-butyl 3-(4,4,5,5-tetramethyl-1,3,2-dioxaborolan-2-yl)-1H-indole-1-carboxylate) reagents. The resulting t-butyl carbamates protected intermediate was treated with 4N HCl in dioxane at RT for 16 hours, then concentrated and purified by silica gel column chromatography to provide the target compound (0.016 g). $^1$H NMR (400 MHz, DMSO-d$_6$) δ ppm 11.60 (s, 1H), 11.18 (s, 1H), 9.00 (m, 1H), 8.48 (m, 1H), 8.42 (m, 1H), 8.31 (m, 1H), 8.24 (m, 1H), 8.20 (s, 1H), 8.15 (s, 1H), 8.00 (m, 2H), 7.94 (m, 1H), 7.50 (m, 3H), 7.18 (m, 1H), 7.06 (m, 1H), 6.79 (m, 1H); m/z 431.2 (MH$^+$).

Preparation of 2-(furan-2-yl)-6-(2-oxo-2,3-dihydro-1H-benzo[d]imidazol-5-yl)-N-(pyridin-3-yl)quinoline-4-carboxamide (21)

The title compound was prepared using the methods shown in Scheme 1 with the appropriate amine (3-pyridylamine) and boronic acid ((2-oxo-2,3-dihydro-1H-benzo[d]imidazol-5-yl)boronic acid) reagents to provide the target compound (0.015 g). $^1$H NMR (400 MHz, DMSO-d$_6$) δ ppm 11.15 (s, 1H), 10.77 (s, 1H), 10.73 (s, 1H), 9.00 (s, 1H), 8.43 (m, 1H), 8.37 (m, 2H), 8.24 (m, 1H), 8.14 (m, 2H), 8.01 (s, 1H), 7.51 (m, 2H), 7.40 (m, 1H), 7.34 (s, 1H), 7.06 (m, 1H), 6.78 (m, 1H); m/z 448.2 (MH$^+$).

Preparation of 2-(furan-2-yl)-N-(pyridin-3-yl)-[6,6'-biquinoline]-4-carboxamide (22)

The title compound was prepared using the methods shown in Scheme 1 with the appropriate amine (3-pyridylamine) and boronic acid (quinolin-6-ylboronic acid) reagents to provide the target compound (0.017 g). $^1$H NMR (400 MHz, DMSO-d$_6$) δ ppm 11.18 (s, 1H), 8.99 (m, 1H), 8.95 (m, 1H), 8.57 (m, 1H), 8.52 (m, 1H), 8.45 (m, 1H), 8.39 (m, 1H), 8.35 (m, 1H), 8.25-8.31 (m, 3H), 8.22 (m, 1H), 8.18 (m, 1H), 8.05 (m, 1H), 7.60 (m, 1H), 7.56 (m, 1H), 7.49 (m, 1H), 6.81 (m, 1H); m/z 443.2 (MH$^+$).

Preparation of 2-(furan-2-yl)-6-(pyridin-2-yl)-N-(pyridin-3-yl)quinoline-4-carboxamide (23)

The title compound was prepared using the methods shown in Scheme 1 with the appropriate amine (3-pyridylamine) and stannane reagent (rather than boronic acid or ester) for the final reaction step (2-(tributylstannyl)pyridine) to provide the target compound (0.015 g). $^1$H NMR (400 MHz, DMSO-d$_6$) δ ppm 11.17 (s, 1H), 8.99 m, 1H), 8.85 (m, 1H), 8.73 (m, 1H), 8.55 (m, 1H), 8.40 (m, 1H), 8.31 (m, 1H), 8.26 (s, 1H), 8.21 (m, 1H), 8.05 (s, 1H), 7.96 (m, 1H), 7.56 (m, 1H), 7.49 (m, 1H), 7.43 (m, 1H), 6.80 (s, 1H); m/z 393.2 (MH$^+$).

Preparation of 2-(furan-2-yl)-6-(pyridin-2-ylamino)-N-(pyridin-3-yl)quinoline-4-carboxamide (24)

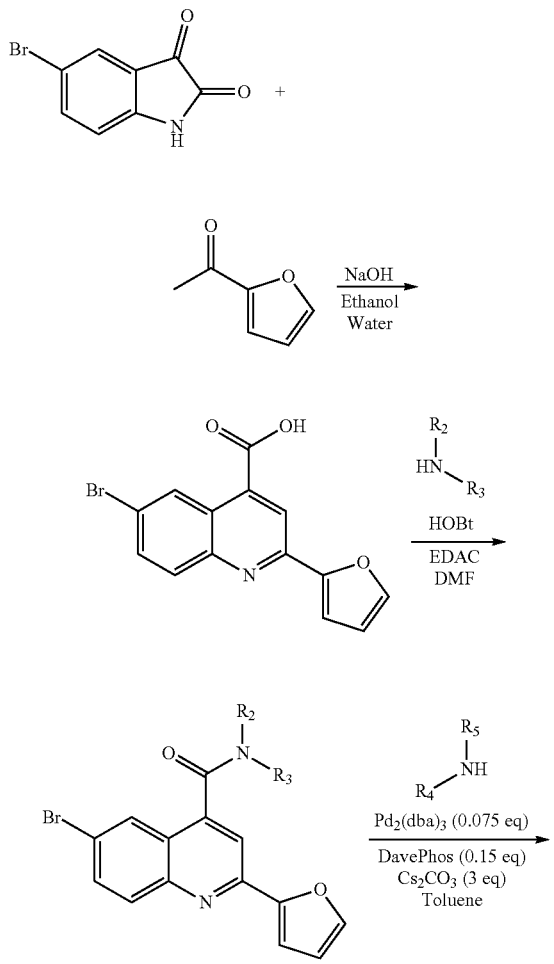

Scheme 2

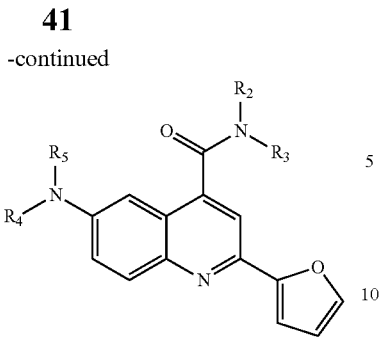

The title compound was prepared using the methods shown in Scheme 2 with the appropriate amine in step 2, amide coupling (3-pyridylamine) and the appropriate amine in step 3, Buchwald coupling (NR$_4$R$_5$) (2-aminopyridine) reagents.

6-bromo-2-(furan-2-yl)-N-(pyridin-3-yl)quinoline-4-carboxamide (prepared as described above, 0.080 g) was added to a sealed tube and dissolved in toluene (5 ml). The vessel was purged with argon for 5 minutes, and 2-aminopyridine (0.029 g, 1.50 eq.) was then added. The vessel was purged with argon for an additional 5 minutes, cesium carbonate (0.200 g) was added, and the tube was purged with argon for an additional 15 minutes. DavePhos (2-(2-dicyclohexylphosphanylphenyl)-N,N-dimethylaniline, 0.012 g) and Pd$_2$(dba)$_3$ (tris(dibenzylideneacetone)dipalladium(0), 0.014 g) were added, the tube was flushed with argon and sealed. The reaction mixture was heated to 90° C. for 16 hours, and completion of the reaction was monitored by TLC using ethyl acetate:hexanes (5:5) as a mobile phase. After completion of the reaction, the reaction mixture was diluted with ethyl acetate (10 ml), filtered through celite bed, which was washed with ethyl acetate (3*10 ml). The ethyl acetate was removed by distillation and the crude product was subjected to silica gel column chromatography purification. Elution of the compound with 20% ethyl acetate in hexanes provided 2-(furan-2-yl)-6-(pyridin-2-ylamino)-N-(pyridin-3-yl)quinoline-4-carboxamide (0.015 g). $^1$H NMR (400 MHz, DMSO-d$_6$) δ ppm 11.06 (s, 1H), 9.62 (s, 1H), 8.99 (m, 1H), 8.57 (m, 1H), 8.41 (m, 1H), 8.27 (m, 2H), 8.05 (m, 2H), 8.00 (m, 1H), 7.95 (m, 1H), 7.61 (m, 1H), 7.50 (m, 1H), 7.38 (m, 1H), 6.92 (m, 1H), 6.81 (m, 1H), 6.74 (m, 1H); m/z 408.2 (MH$^+$).

Preparation of 6-((2-(benzyl(methyl)amino)ethyl)amino)-2-(furan-2-yl)-N-(pyridin-3-yl)quinoline-4-carboxamide (25)

Scheme 3

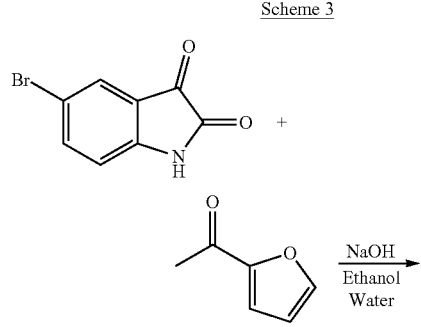

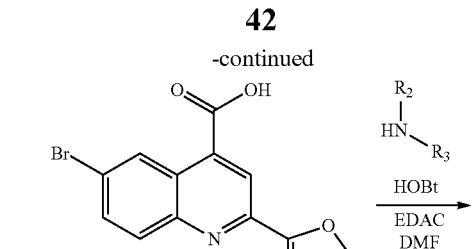

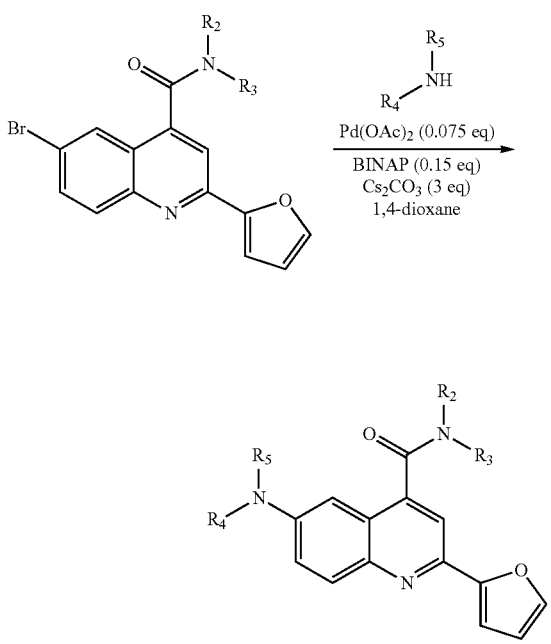

The title compound was prepared using the methods shown in Scheme 3 with the appropriate amine in step 2, amide coupling (3-pyridylamine) and the appropriate amine in step 3, Buchwald coupling (NR$_4$R$_5$) (N1-benzyl-N1-methylethane-1,2-diamine) to provide the title compound (0.011 g). $^1$H NMR (400 MHz, DMSO-d$_6$) δ ppm 10.94 (s, 1H), 8.98 (s, 1H), 8.41 (m, 1H), 8.37 (m, 1H), 8.04 (s, 1H), 7.90 (m, 1H), 7.75 (s, 1H), 7.52 (m, 2H), 7.36-7.26 (broad m, 7H), 7.10 (m, 1H), 6.67 (broad s, 1H), 3.86 (m, 2H), 3.46 (m, 2H), 2.93 (m, 2H), 2.48 (m, 3H); m/z 478.4 (MH$^+$).

Preparation of 6-(1H-benzo[d]imidazol-5-yl)-2-(furan-2-yl)-N-(pyridin-3-yl)quinoline-4-carboxamide (26)

The title compound was prepared using a modified version of the methods shown in Scheme 1. The appropriate amine (3-pyridylamine) was used for the amide bond formation reaction as shown (step 2). However, alternative conditions (Bis(di-tbutyl)4-dimethylaminophenyl)phosphine)dichloro palladium (II) (0.01 eq.), potassium carbonate (2.00 eq), (1H-benzo[d]imidazol-5-yl)boronic acid (1.5 eq.), dioxane, water) were used for Suzuki coupling (step 3). The target compound was obtained with a yield of 0.045 g. $^1$H NMR (400 MHz, DMSO-d$_6$) δ ppm 13.02 (broad s, 1H), 11.17 (s, 1H), 8.99 (s, 1H), 8.40 (m, 3H), 8.31 (m, 1H), 8.25 (m, 2H), 8.20 (m, 1H), 8.03 (m, 2H), 7.75 (m, 1H), 7.66 (m, 1H), 7.54 (m, 1H), 7.47 (m, 1H); 6.80 (m, 1H); m/z 432.2 (MH+).

Preparation of 2-(furan-2-yl)-6-((2-(phenylamino)ethyl)amino)-N-(pyridin-3-yl)quinoline-4-carboxamide (27)

Scheme 4

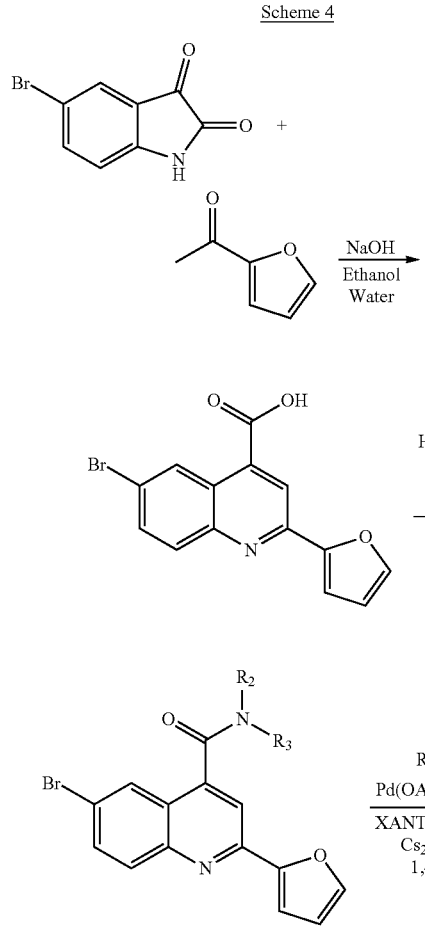

The title compound was prepared using the methods shown in Scheme 4 with the appropriate amine in step 2, amide coupling (3-pyridylamine) and the appropriate amine in step 3, Buchwald coupling (NR$_4$R$_5$) (N1-phenylethane-1,2-diamine) to provide the title compound (0.020 g). $^1$H NMR (400 MHz, DMSO-d$_6$) δ ppm 10.96 (s, 1H), 8.96 (s, 1H), 8.39 (m, 1H), 8.32 (m, 1H), 8.25 (m, 1H), 7.98 (s, 1H), 7.90 (m, 1H), 7.82 (m, 1H), 7.46 (m, 1H), 7.33 (m, 1H), 7.26 (m, 1H), 7.06 (m, 2H), 7.02 (m, 1H), 6.71 (m, 1H), 6.57 (m, 2H), 7.51 (m, 1H), 5.68 (broad s, 1H), 3.29 (m, 4H); m/z 450.3 (MH+).

Preparation of 2-(furan-2-yl)-6-(1H-indol-5-yl)-N-(pyridin-3-yl)quinoline-4-carboxamide (28)

Scheme 5

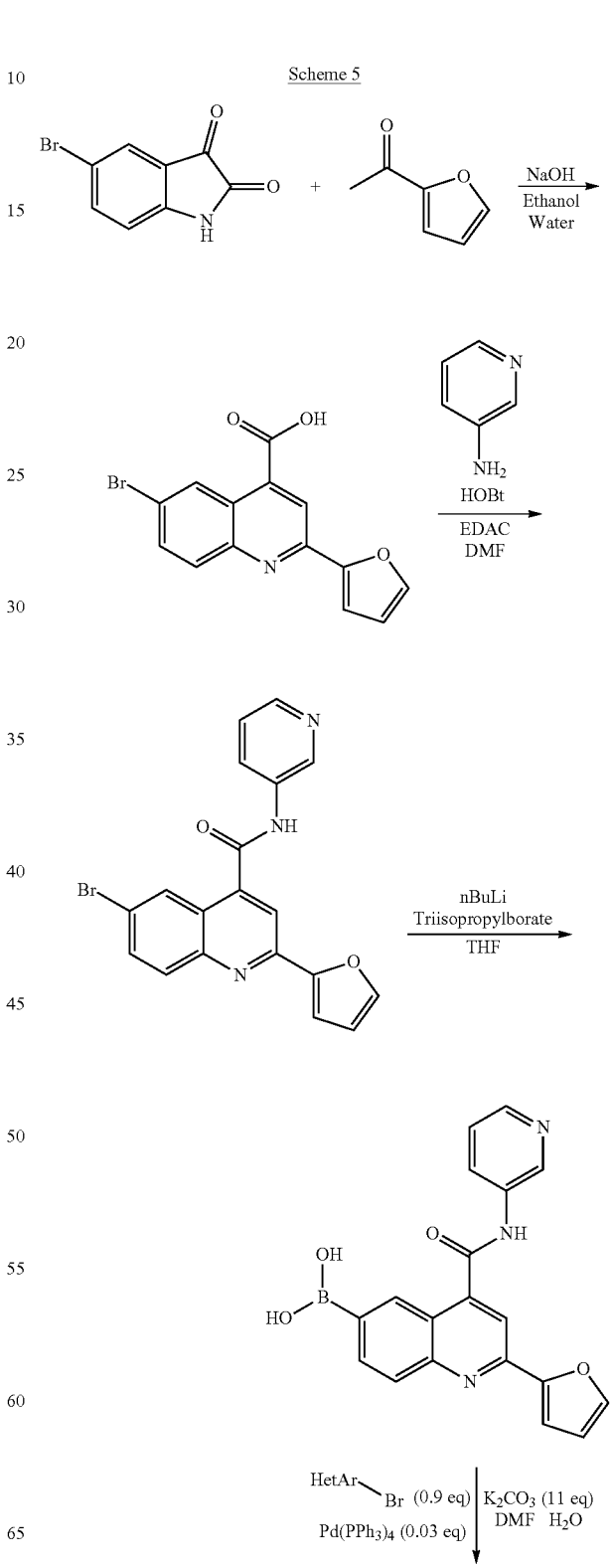

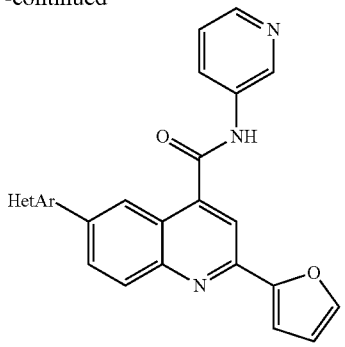

The title compound was prepared using the methods shown in Scheme 5.

6-bromo-2-(furan-2-yl)-N-(pyridin-3-yl)quinoline-4-carboxamide (0.4 g, prepared as described above for compound 1) was dissolved in THF (15 ml) in a round-bottomed flask under argon atmosphere. The solution was cooled to −78° C., then n-BuLi (15% in hexanes, 1.0 ml, 1.5 eq) was added dropwise. The reaction was maintained at this temperature for 45 minutes, at which time triisopropylborate (0.376 g, 2.0 eq.) was added dropwise. The reaction was allowed to warm to RT and stirred for an additional 3 hours. The completion of the reaction was monitored on TLC using methanol:dichloromethane (1:9) as a mobile phase. After completion of the reaction, the reaction mixture was quenched with saturated NH$_4$Cl solution (10 ml), then was extracted with ethyl acetate (2*10 ml) which was discarded. The aqueous layer was added Conc.HCl to adjust pH up to 6-7. The solid was precipitated which further was filtered on Buckner funnel and washed with water (10 ml). The solid was dried to obtain (2-(furan-2-yl)-4-(pyridin-3-ylcarbamoyl)quinolin-6-yl)boronic acid (0.300 g) which was used as such in next step.

To a sealed tube under argon atmosphere was added (2-(furan-2-yl)-4-(pyridin-3-ylcarbamoyl)quinolin-6-yl)boronic acid (0.120 g) in DMF (4 ml) and the vessel was purged with argon under stirring for 5 minutes. After 5 minutes, a 2N aqueous solution of potassium carbonate was added (1.8 ml, 11 eq) and the tube was purged with argon under stirring for 5 minutes. 5-bromoindole (0.057 g, 0.9 eq) was then added and the vessel was purged with argon under stirring for 15 minutes. Finally tetrakistriphenylphosphine palladium(0) (0.011 g, 0.03 eq.) was added under argon and the tube was sealed. The reaction mixture was heated to 90° C. for 5 hours. The completion of the reaction was monitored by TLC using ethyl acetate:hexanes (5:5) as a mobile phase. After completion of the reaction, the reaction mixture was diluted with ethyl acetate (10 ml) and then washed with water (5*10 ml). The ethyl acetate layer was dried over anhydrous sodium sulfate and the solvent was removed by distillation and the crude product was subjected to purification by high performance liquid chromatography to provide 2-(furan-2-yl)-6-(1H-indol-5-yl)-N-(pyridin-3-yl)quinoline-4-carboxamide (0.008 g). $^1$H NMR (400 MHz, DMSO-d$_6$) δ ppm 11.34 (s, 1H), 11.19 (s, 1H), 9.00 (m, 1H), 8.41 (m, 1H), 8.35 (m, 1H), 8.30 (m, 1H), 8.20 (m, 1H), 8.12 (m, 2H), 7.85 (m, 1H), 7.70 (m, 1H), 7.4 (m, 1H), 7.58 (m, 1H), 7.50 (m, 2H), 7.43 (m, 1H), 7.12 (m, 1H), 6.54 (m, 1H); m/z 431.2 (MH$^+$).

Preparation of 2'-(furan-2-yl)-N-(pyridin-3-yl)-[2,6'-biquinoline]-4'-carboxamide (29)

The title compound was prepared using the methods shown in Scheme 5 with the appropriate amine in step 2, amide coupling (3-pyridylamine) and the appropriate bromide in step 4, Suzuki coupling (2-bromoquinoline) to provide the title compound (0.010 g). $^1$H NMR (400 MHz, DMSO-d$_6$) δ ppm 11.19 (s, 1H), 9.02 (m, 1H), 8.54 (m, 1H), 8.47 (m, 1H), 8.43 (m, 1H), 8.30 (m, 2H), 8.18 (m, 2H), 8.10 (m, 1H), 8.04 (m, 1H), 7.90 (m, 1H), 7.84 (m, 1H), 7.74 (m, 2H), 7.64 (m, 2H), 7.50 (m, 1H); m/z 443.2 (MH$^+$).

Preparation of 2-(5-methylfuran-2-yl)-6-phenyl-N-(pyridin-3-yl)quinoline-4-carboxamide (30)

Scheme 6

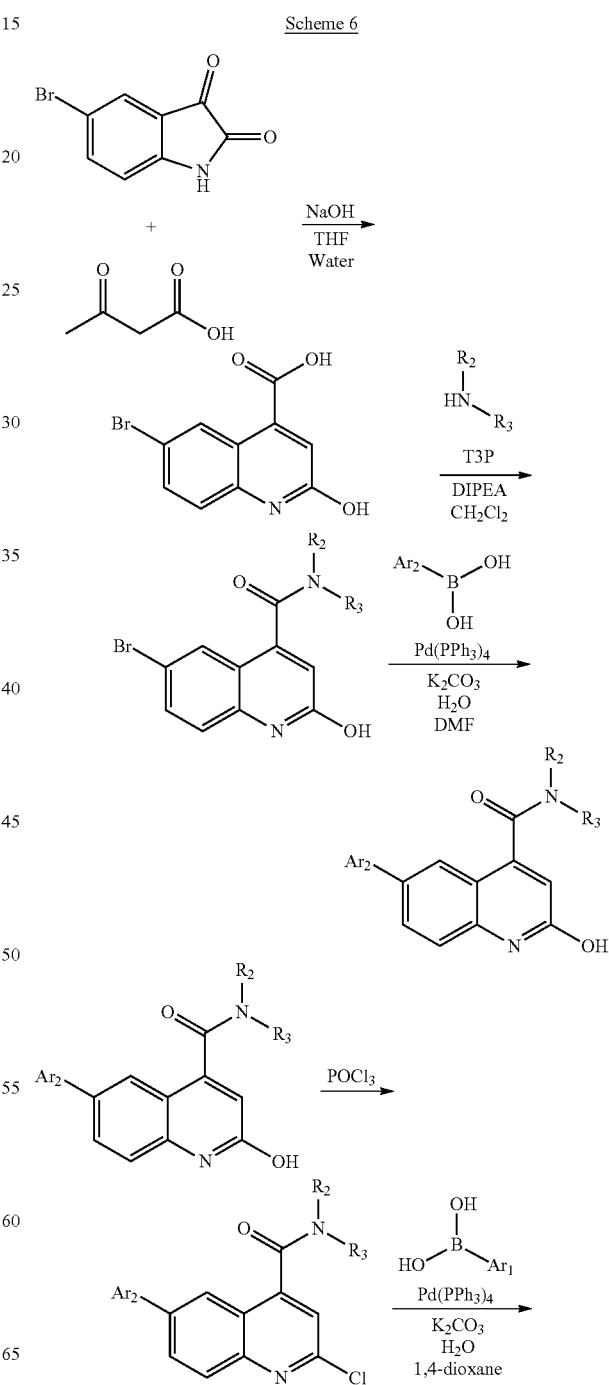

-continued

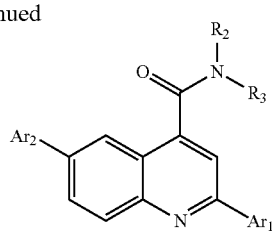

The title compound was prepared using the methods shown in Scheme 6.

5-bromoindoline-2,3-dione (0.250 g) was dissolved in THF (3 ml) in a round-bottomed flask and malonic acid (2 eq) was added. The vessel was connected to a reflux condenser and heated to reflux overnight by conventional heating. After 12 hours, solid precipitate was observed. Suspension was concentrated under reduced pressure to remove solvent, water was added, and the suspension was refluxed for 4 hours. The suspension was then filtered to provide 6-bromo-2-hydroxyquinoline-4-carboxylic acid (0.150 g) as a solid.

A solution of 6-bromo-2-hydroxyquinoline-4-carboxylic acid (9.0 g) was dissolved in dichloromethane and cooled to 0° C. 3-aminopyridine (1 eq), T3P (2,4,6-tripropyl-1,3,5,2,4,6-trioxatriphosphinane 2,4,6-trioxide, 50% solution in ethyl acetate, 1.2 eq.), and DIPEA (diisopropylethylamine, 2.0 eq) were added. The solution was stirred at 0° C. for 30 minutes and then allowed to warm to room temperature overnight. The solution was washed with water, sat. sodium chloride, dried, and concentrated. Purification by silica gel column chromatography provided 6-bromo-2-hydroxy-N-(pyridin-3-yl)quinoline-4-carboxamide (9.0 g).

To a round-bottomed flask under argon atmosphere was added 6-bromo-2-hydroxy-N-(pyridin-3-yl)quinoline-4-carboxamide (3.00 g) in DMF (50 ml), and the vessel was purged with argon under stirring for 5 minutes. After 5 minutes, 2N solution of potassium carbonate in water (11 eq) was added and the flask was purged with argon under stirring for 5 minutes. Phenylboronic acid (1.5 eq) was then added and the tube was purged with argon under stirring for 15 minutes. Finally, palladium(0)tetrakis triphenylphosphine (0.03 eq) was added under argon and the flask was affixed to a reflux condenser and heated to 80° C. for 5 hours. The completion of the reaction was monitored on TLC using ethyl acetate:hexanes (5:5) as a mobile phase. After completion of the reaction, reaction mixture was diluted with ethyl acetate (100 ml) and then washed with water (5*100 ml). The ethyl acetate layer was dried over anhydrous sodium sulphate and then solvent was distilled out and the crude was subjected to purification by silica gel column chromatography to provide 9.0 g of 2-hydroxy-6-phenyl-N-(pyridin-3-yl)quinoline-4-carboxamide.

A solution of 2-hydroxy-6-phenyl-N-(pyridin-3-yl)quinoline-4-carboxamide (1.64 g) in phosphorus oxychloride (3 eq) was prepared and heated to reflux for 4 hours. The phosphorus oxychloride was removed by concentration under reduced pressure and the resulting residue was added to ice water, extracted with ethyl acetate, washed with water, brine, dried, and concentrated to provide 2-chloro-6-phenyl-N-(pyridin-3-yl)quinoline-4-carboxamide (1.07 g).

To a round-bottomed flask under argon atmosphere was added 2-chloro-6-phenyl-N-(pyridin-3-yl)quinoline-4-carboxamide (0.100 g) in 1,4-dioxane (3 ml), and the vessel was purged with argon under stirring for 5 minutes. After 5 minutes, a 2N solution of potassium carbonate in water (11 eq) was added and the flask was purged with argon under stirring for 5 minutes. (5-methylfuran-2-yl)boronic acid (1.5 eq) was then added and the tube was purged with argon under stirring for 15 minutes. Finally, palladium(0)tetrakis triphenylphosphine (0.05 eq) was added under argon and the flask was affixed to a reflux condenser and heated to 90° C. for 5 hours. The completion of the reaction was monitored on TLC using ethyl acetate:hexanes as a mobile phase. After completion of the reaction, reaction mixture was diluted with ethyl acetate (100 ml) and then washed with water (5*100 ml). The ethyl acetate layer was dried over anhydrous sodium sulphate and then solvent was distilled out and the crude was subjected to purification by silica gel column chromatography to provide 0.01 g of 2-(5-methylfuran-2-yl)-6-phenyl-N-(pyridin-3-yl)quinoline-4-carboxamide. $^1$H NMR (400 MHz, DMSO-d$_6$) δ ppm 11.12 (s, 1H), 8.97 (s, 1H), 8.41 (m, 1H), 8.39 (s, 1H), 8.30 (m, 1H), 8.19 (m, 3H), 7.78 (m, 2H), 7.55 (m, 2H), 7.48 (m, 1H), 7.44 (m, 2H), 6.43 (broad s, 1H), 2.48 (s, 3H); m/z 406.2 (MH$^+$).

Preparation of 2-(benzofuran-2-yl)-6-phenyl-N-(pyridin-3-yl)quinoline-4-carboxamide (31)

The title compound was prepared using the methods shown in Scheme 6 with the appropriate amine in step 2, amide coupling (3-pyridylamine), the appropriate boronic acid in step 3, Suzuki coupling (phenylboronic acid), and the appropriate boronic acid in step 5, Suzuki coupling (benzofuran-2-ylboronic acid) to provide the title compound (0.019 g). $^1$H NMR (400 MHz, DMSO-d$_6$) δ ppm 11.20 (s, 1H), 9.00 (s, 1H), 8.48 (m, 1H), 8.45 (s, 1H), 8.42 (m, 1H), 8.33 (m, 1H), 8.30 (s, 1H), 8.26 (m, 1H), 8.02 (s, 1H), 7.77-7.85 (broad m, 4H), 7.56 (m, 2H), 7.45-7.53 (broad m, 3H), 7.38 (m, 1H); m/z 442.3 (MH$^+$).

Preparation of 6-(benzo[d]thiazol-5-yl)-2-(furan-2-yl)-N-methylquinoline-4-carboxamide (32)

The title compound was prepared using the methods shown in Scheme 1 with the appropriate amine for step 2, amide formation (methylamine) and boronic acid for step 3, Suzuki coupling (benzo[d]thiazol-5-ylboronic acid) reagents to provide the title compound (0.023 g). $^1$H NMR (400 MHz, DMSO-d$_6$) δ ppm 9.51 (s, 1H), 8.90 (m, 1H), 8.50 (m, 2H), 8.36 (m, 1H), 8.28 (m, 1H), 8.18 (m, 1H), 8.03 (m, 2H), 7.92 (m, 1H), 7.49 (m, 1H), 6.79 (broad s, 1H), 2.94 (m, 3H); m/z 386.2 (MH$^+$).

Preparation of 6-(benzo[d]thiazol-5-yl)-2-(furan-2-yl)-N-phenylquinoline-4-carboxamide (33)

The title compound was prepared using the methods shown in Scheme 1 with the appropriate amine for step 2, amide formation (aniline) and boronic acid for step 3, Suzuki coupling (benzo[d]thiazol-5-ylboronic acid) reagents to provide the title compound (0.014 g). $^1$H NMR (400 MHz, DMSO-d$_6$) δ ppm 10.94 (s, 1H), 9.49 (s, 1H), 8.47 (m, 2H), 8.32 (m, 2H), 8.22 (m, 2H), 8.03 (s, 1H), 7.91 (m, 1H), 7.86 (m, 2H), 7.57 (s, 1H), 7.44 (m, 2H), 7.19 (m, 1H), 6.80 (broad s, 1H); m/z 448.3 (MH$^+$).

Preparation of 2-(1,3-dimethyl-1H-pyrazol-4-yl)-6-phenyl-N-(pyridin-3-yl)quinoline-4-carboxamide (34)

The title compound was prepared using the methods shown in Scheme 6 with the appropriate amine in step 2, amide coupling (3-pyridylamine), the appropriate boronic acid in step 3, Suzuki coupling (phenylboronic acid), and the appropriate boronic acid in step 5, Suzuki coupling ((1,3-dimethyl-1H-pyrazol-4-yl)boronic acid) to provide the title compound (0.009 g). $^1$H NMR (400 MHz, DMSO-$d_6$) δ ppm 11.09 (s, 1H), 9.00 (s, 1H), 8.55 (s, 1H), 8.40 (m, 1H), 8.33 (s, 1H), 8.29 (m, 1H), 8.12 (m, 2H), 8.05 (m, 1H), 7.77 (m, 2H), 7.50 (m, 2H), 7.46 (m, 1H), 7.41 (m, 1H), 3.87 (m, 3H), 2.66 (s, 1H); m/z 420.4 (MH$^+$).

Preparation of 2-(furan-2-yl)-6-((2-phenoxyethyl)amino)-N-(pyridin-3-yl)quinoline-4-carboxamide (35)

The title compound was prepared using the methods shown in Scheme 4 with the appropriate amine in step 2, amide coupling (3-pyridylamine) and the appropriate amine in step 3, Buchwald coupling (NR$_4$R$_5$) (2-phenoxyethanamine) to provide the title compound (0.010 g). $^1$H NMR (400 MHz, DMSO-$d_6$) δ ppm 10.95 (s, 1H), 8.96 (s. 1H), 8.37 (m, 1H), 8.25 (m, 1H), 7.97 (m, 1H), 7.91 (s, 1H), 7.83 (m, 1H), 7.46 (m, 1H), 7.38 (m, 1H), 7.32 (m, 1H), 7.28 (m, 2H), 7.05 (s, 1H), 6.96 (m, 2H), 6.93 (m, 1H), 6.72 (m, 1H), 4.16 (m, 2H), 3.50 (m, 2H); m/z 451.4 (MH$^+$).

Preparation of 2-(1-methyl-1H-pyrazol-4-yl)-6-phenyl-N-(pyridin-3-yl)quinoline-4-carboxamide (36)

The title compound was prepared using the methods shown in Scheme 6 with the appropriate amine in step 2, amide coupling (3-pyridylamine), the appropriate boronic acid in step 3, Suzuki coupling (phenylboronic acid), and the appropriate boronic acid in step 5, Suzuki coupling ((l-methyl-1H-pyrazol-4-yl)boronic acid) to provide the title compound (0.015 g). $^1$H NMR (400 MHz, DMSO-$d_6$) δ ppm 8.97 (broad s, 1H), 8.61 (s, 1H), 8.40 (m, 1H), 8.26-8.33 (broad m, 3H), 8.17 (s, 1H), 8.14 (m, 2H), 7.78 (m, 2H), 7.53 (m, 2H), 7.41-7.48 (broad m, 2H), 3.96 (s, 3H); m/z 406.2 (MH$^+$).

Preparation of 6-phenyl-N-(pyridin-3-yl)-2-(1-(tetrahydro-2H-pyran-2-yl)-1H-pyrazol-4-yl)quinoline-4-carboxamide (37)

The title compound was prepared using the methods shown in Scheme 6 with the appropriate amine in step 2, amide coupling (3-pyridylamine), the appropriate boronic acid in step 3, Suzuki coupling (phenylboronic acid), and the appropriate boronic acid in step 5, Suzuki coupling ((1-(tetrahydro-2H-pyran-2-yl)-1H-pyrazol-4-yl)boronic acid) to provide the title compound (0.012 g). $^1$H NMR (400 MHz, DMSO-$d_6$) δ ppm 8.98 (broad s, 1H), 8.84 (s, 1H), 8.41 (m, 1H), 8.26-8.35 (broad m, 4H), 8.15 (m, 2H), 7.78 (m, 2H), 7.53 (m, 2H), 7.47 (m, 1H), 7.44 (m, 1H), 5.52 (m, 1H), 4.00 (m, 1H), 3.70 (m, 1H), 2.17 (m, 1H), 2.00 (m, 2H), 1.73 (m, 1H), 1.60 (m, 2H); m/z 476.3 (MH$^+$).

Preparation of 6-phenyl-2-(1H-pyrazol-4-yl)-N-(pyridin-3-yl)quinoline-4-carboxamide (38)

The title compound was prepared using the methods shown in Scheme 6 with the appropriate amine in step 2, amide coupling (3-pyridylamine), the appropriate boronic acid in step 3, Suzuki coupling (phenylboronic acid), and the appropriate boronic acid in step 5, Suzuki coupling ((1H-pyrazol-4-yl)boronic acid) to provide the title compound (0.012 g). $^1$H NMR (400 MHz, DMSO-$d_6$) δ ppm 13.29 (broad s, 1H), 11.11 (s, 1H), 8.98 (s, 1H), 8.67 (s, 1H), 8.40 (m, 1H), 8.32 (m, 2H), 8.22 (s, 1H), 8.14 (m, 2H), 7.77 (m, 2H), 7.53 (m, 2H), 7.48 (m, 1H), 7.42 (m, 2H); m/z 392.2 (MH$^+$).

Preparation of (6-(benzo[d]thiazol-5-yl)-2-(furan-2-yl)quinolin-4-yl)(4-methylpiperazin-1-yl)methanone (39)

The title compound was prepared using the methods shown in Scheme 1 with the appropriate amine for step 2, amide formation (N-methylpiperazine) and boronic acid for step 3, Suzuki coupling (benzo[d]thiazol-5-ylboronic acid) reagents to provide the title compound (0.012 g). $^1$H NMR (400 MHz, DMSO-$d_6$) δ ppm 9.51 (s, 1H), 8.48 (s, 1H), 8.37 (m, 1H), 8.30 (m, 1H), 8.20 (m, 1H), 8.00 (m, 2H), 7.96 (s, 1H), 7.93 (m, 1H), 7.51 (m, 1H), 6.78 (m, 1H), 3.95 (m, 1H), 3.75 (m, 1H), 3.25 (m, 2H), 2.55 (m, 2H), 2.34 (m, 1H), 2.21 (m, 3H), 2.15 (m, 1H); m/z 455.2 (MH$^+$).

Preparation of 6-(benzo[d]thiazol-5-yl)-N-cyclopropyl-2-(furan-2-yl)quinoline-4-carboxamide (40)

The title compound was prepared using the methods shown in Scheme 1 with the appropriate amine for step 2, amide formation (cyclopropylamine) and boronic acid for step 3, Suzuki coupling (benzo[d]thiazol-5-ylboronic acid) reagents to provide the title compound (0.030 g). $^1$H NMR (400 MHz, DMSO-$d_6$) δ ppm 9.51 (s, 1H), 9.01 (m, 1H), 8.47 (m, 2H), 8.38 (m, 1H), 8.29 (m, 1H), 8.18 (m, 1H), 8.00 (m, 2H), 7.91 (m, 1H), 7.49 (m, 1H), 6.78 (m, 1H), 3.03 (m, 1H), 0.80 (m, 2H), 0.67 (m, 2H); m/z 412.2 (MH$^+$).

Preparation of 6-phenyl-N-(pyridin-3-yl)-2-(thiazol-2-yl)quinoline-4-carboxamide (41)

The title compound was prepared using the methods shown in Scheme 6 with the appropriate amine in step 2, amide coupling (3-pyridylamine), the appropriate boronic acid in step 3, Suzuki coupling (phenylboronic acid), and the appropriate boronic acid in step 5, Suzuki coupling (thiazol-2-ylboronic acid) to provide the title compound (0.006 g). $^1$H NMR (400 MHz, DMSO-$d_6$) δ ppm 11.22 (s, 1H), 8.98 (m, 1H), 8.55 (s, 1H), 8.48 (m, 1H), 8.41 (m, 1H), 8.25-8.30 (m, 3H), 8.16 (m, 1H), 8.07 (m, 1H), 7.83 (m, 2H), 7.55 (m, 2H), 7.47 (m, 2H); m/z 409.2 (MH$^+$).

Preparation of 6-(benzo[d]thiazol-5-yl)-N-cyclohexyl-2-(furan-2-yl)quinoline-4-carboxamide (42)

The title compound was prepared using the methods shown in Scheme 1 with the appropriate amine for step 2, amide formation (cyclohexylamine) and boronic acid for step 3, Suzuki coupling (benzo[d]thiazol-5-ylboronic acid) reagents to provide the title compound (0.004 g). $^1$H NMR (400 MHz, DMSO-$d_6$) δ ppm 9.51 (s, 1H), 8.85 (m, 1H), 8.44 (m, 2H), 8.37 (m, 1H), 8.28 (m, 1H), 8.18 (m, 1H), 8.03 (m, 1H), 7.96 (s, 1H), 7.90 (m, 1H), 7.48 (m, 1H), 6.78 (m, 1H), 3.94 (m, 1H), 1.99 (m, 2H), 1.77 (m, 2H), 1.64 (m, 1H), 1.36 (m, 3H), 1.19 (m, 2H); m/z 454.2 (MH$^+$).

Preparation of 2-(oxazol-2-yl)-6-phenyl-N-(pyridin-3-yl)quinoline-4-carboxamide (43)

The title compound was prepared using the methods shown in Scheme 6 with the appropriate amine in step 2, amide coupling (3-pyridylamine), the appropriate boronic acid in step 3, Suzuki coupling (phenylboronic acid), and the appropriate boronic acid in step 5, Suzuki coupling (oxazol-2- ylboronic acid) to provide the title compound (0.032 g). $^1$H NMR (400 MHz, DMSO-d$_6$) δ ppm 11.21 (s, 1H), 9.00 (s, 1H), 8.49 (m, 3H), 8.41 (m, 1H), 8.33 (m, 1H), 8.28 (m, 2H), 7.84 (m, 2H), 7.64 (m, 1H), 7.55 (m, 2H), 7.47 (m, 2H); m/z 393.2 (MH$^+$).

Preparation of 6-(benzo[d]thiazol-5-yl)-2-(furan-2-yl)-N-(pyridin-4-yl)quinoline-4-carboxamide (44)

The title compound was prepared using the methods shown in Scheme 1 with slight modification. For step 2, amide formation, the carboxylic acid starting material was treated with 4-pyridylamine (1.0 eq), HATU (1.2 eq), dimethylaminopyridine (1.1 eq), and triethylamine (3 eq) in DMF, followed by aqueous workup and purification by silica gel column chromatography, to provide the amide product. Step 3, Suzuki coupling was performed as shown in Scheme 1, utilizing the appropriate boronic acid reagent (benzo[d]thiazol-5-ylboronic acid) to provide the title compound (0.040 g). $^1$H NMR (400 MHz, DMSO-d$_6$) δ ppm 11.30 (s, 1H), 9.49 (s, 1H), 8.58 (m, 2H), 8.49 (m, 2H), 8.33 (m, 2H), 8.28 (s, 1H), 8.25 (m, 1H), 8.04 (s, 1H), 7.93 (m, 1H), 7.84 (m, 2H), 7.56 (m, 1H), 6.80 (m, 1H); m/z 449.2 (MH$^+$).

Preparation of N-(benzo[d]thiazol-2-yl)-6-(benzo[d]thiazol-5-yl)-2-(furan-2-yl)quinoline-4-carboxamide (45)

The title compound was prepared using the methods shown in Scheme 1 with the appropriate amine for step 2, amide formation (2-aminobenzothiazole) and boronic acid for step 3, Suzuki coupling (benzo[d]thiazol-5-ylboronic acid) reagents to provide the title compound (0.021 g). $^1$H NMR (400 MHz, DMSO-d$_6$) δ ppm 13.41 (m, 1H), 9.50 (s, 1H), 8.59 (broad m, 1H), 8.52 (m, 1H), 8.40 (s, 1H), 8.36 (m, 2H), 8.24 (m, 1H), 8.09 (m, 1H), 8.05 (s, 1H), 7.96 (m, 1H), 7.83 (m, 1H), 7.55 (m, 1H), 7.50 (m, 1H), 7.39 (m, 1H), 6.81 (m, 1H); m/z 505.1 (MH$^+$).

Preparation of methyl 1-(6-(benzo[d]thiazol-5-yl)-2-(furan-2-yl)quinoline-4-carbonyl)piperidine-3-carboxylate (46)

The title compound was prepared using the methods shown in Scheme 1 with the appropriate amine for step 2, amide formation (methyl piperidine-3-carboxylate) and boronic acid for step 3, Suzuki coupling (benzo[d]thiazol-5-ylboronic acid) reagents to provide the title compound (0.017 g). $^1$H NMR (400 MHz, DMSO-d$_6$) δ ppm 9.51 (m, 1H), 8.53 (m, 1H), 8.36 (m, 1H), 8.29 (m, 1H), 8.18 (m, 1H), 7.91-8.09 (broad m, 4H), 7.49 (m, 1H), 6.78 (m, 1H), 4.07 (m, 1H), 3.69 (m, 2H), 3.39 (s, 3H), 2.87 (m, 1H), 1.98 (m, 2H), 1.78 (m, 2H), 1.58 (m, 1H); m/z 498.2 (MH$^+$).

Preparation of 6-(benzo[d]thiazol-5-yl)-2-(furan-2-yl)-N-(pyridin-2-yl)quinoline-4-carboxamide (47)

The title compound was prepared using the methods shown in Scheme 1 with slight modification. For step 2, amide formation, the carboxylic acid starting material was treated with 2-pyridylamine (1.0 eq), HATU (1.2 eq), dimethylaminopyridine (1.1 eq), and triethylamine (3 eq) in DMF, followed by aqueous workup and purification by silica gel column chromatography, to provide the amide product. Step 3, Suzuki coupling was performed as shown in Scheme 1, utilizing the appropriate boronic acid reagent (benzo[d]thiazol-5-ylboronic acid) to provide the title compound (0.038 g). $^1$H NMR (400 MHz, DMSO-d$_6$) δ ppm 11.46 (s, 1H), 9.49 (s, 1H), 8.48 (m, 2H), 8.44 (m, 1H), 8.37 (m, 1H), 8.34 (m, 2H), 8.21 (m, 2H), 8.03 (m, 1H), 7.93 (m, 2H), 7.53 (m, 1H), 7.24 (m, 1H), 6.80 (m, 1H); m/z 449.2 (MH$^+$).

Preparation of 6-(benzo[d]thiazol-5-yl)-2-(furan-2-yl)-N-methyl-N-(pyridin-3-yl)quinoline-4-carboxamide (48)

The title compound was prepared using the methods shown in Scheme 1 with slight modification. For step 2, amide formation, the carboxylic acid starting material was treated with N-methyl-3-aminopyridine (1.0 eq), HATU (1.2 eq), dimethylaminopyridine (1.1 eq), and triethylamine (3 eq) in DMF, followed by aqueous workup and purification by silica gel column chromatography, to provide the amide product. Step 3, Suzuki coupling was performed as shown in Scheme 1, utilizing the appropriate boronic acid reagent (benzo[d]thiazol-5-ylboronic acid) to provide the title compound (0.020 g). $^1$H NMR (400 MHz, DMSO-d$_6$) δ ppm 9.12 (s, 1H), 8.55 (broad s, 1H), 8.47 (m, 1H), 8.32 (m, 1H), 8.23 (m, 1H), 8.18 (m, 1H), 8.14 (m, 1H), 8.08 (m, 1H), 7.85 (m, 1H), 7.62 (m, 1H), 7.56 (m, 1H), 7.42 (m, 1H), 7.18 (m, 1H), 7.07 (m, 1H), 6.60 (m, 1H), 3.71 (m, 3H); m/z 463.2 (MH$^+$).

Preparation of methyl 1-(6-(benzo[d]thiazol-5-yl)-2-(furan-2-yl)quinoline-4-carbonyl)piperidine-4-carboxylate (49)

The title compound was prepared using the methods shown in Scheme 1 with the appropriate amine for step 2, amide formation (methyl piperidine-4-carboxylate) and boronic acid for step 3, Suzuki coupling (benzo[d]thiazol-5-ylboronic acid) reagents to provide the title compound (0.018 g). $^1$H NMR (400 MHz, DMSO-d$_6$) δ ppm 9.50 (s, 1H), 8.47 (m, 1H), 8.32 (m, 1H), 8.27 (m, 1H), 8.19 (m, 1H), 8.00 (m, 1H), 7.95 (m, 1H), 7.90 (m, 2H), 7.45 (m, 1H), 6.75 (m, 1H), 4.58 (m, 1H), 3.63 (s, 3H), 3.42 (m, 1H), 3.20 (m, 2H), 2.72 (m, 1H), 2.09 (m, 1H), 1.78 (m, 2H), 1.51 (m, 2H); m/z 498.3 (MH$^+$).

Preparation of 2-(furan-2-yl)-6-(4-phenylpiperazin-1-yl)-N-(pyridin-3-yl)quinoline-4-carboxamide (50)

The title compound was prepared using the methods shown in Scheme 3 with the appropriate amine in step 2, amide coupling (3-pyridylamine) and the appropriate amine in step 3, Buchwald coupling (NR$_4$R$_5$) (N-phenylpiperazine) to provide the title compound (0.010 g). $^1$H NMR (400 MHz, DMSO-d$_6$) δ ppm 11.02 (s, 1H), 8.97 (m, 1H), 8.40 (m, 1H), 8.28 (m, 1H), 8.08 (s, 1H), 7.97 (m, 1H), 7.94 (m, 1H), 7.80 (m, 1H), 7.48 (m, 1H), 7.44 (m, 1H), 7.35 (m, 1H), 7.24 (m, 2H), 7.01 (m, 2H), 6.83 (m, 1H), 6.75 (m, 1H), 3.45 (m, 4H), 3.35 (m, 4H); m/z 476.3 (MH$^+$).

Preparation of N-(1H-benzo[d]imidazol-2-yl)-6-(benzo[d]thiazol-5-yl)-2-(furan-2-yl)quinoline-4-carboxamide (51)

The title compound was prepared using the methods shown in Scheme 1 with the appropriate amine for step 2, amide formation (2-aminobenzimidazole) and boronic acid for step 3, Suzuki coupling (benzo[d]thiazol-5-ylboronic acid) reagents to provide the title compound (0.008 g). $^1$H NMR (400 MHz, DMSO-d$_6$) δ ppm 12.78 (broad m, 2H), 9.50 (s, 1H), 9.10 (m, 1H), 8.54 (m, 1H), 8.45 (m, 1H), 8.33 (m, 1H), 8.29 (m, 1H), 8.20 (m, 1H), 8.05 (s, 1H), 7.96 (m, 1H), 7.50 (m, 2H), 7.48 (m, 1H), 7.20 (m, 2H), 6.80 (m, 1H); m/z 488.2 (MH$^+$).

Preparation of 6-(benzo[d]thiazol-5-yl)-N-methyl-2-(oxazol-2-yl)quinoline-4-carboxamide (52)

The title compound was prepared using the methods shown in Scheme 6 with the appropriate amine in step 2, amide coupling (methylamine), the appropriate boronic acid in step 3, Suzuki coupling (benzo[d]thiazol-5-ylboronic acid), and the appropriate boronic acid in step 5, Suzuki coupling (oxazol-2-ylboronic acid) to provide the title compound (0.0040 g). $^1$H NMR (400 MHz, DMSO-d$_6$) δ ppm 9.52 (s, 1H), 9.00 (m, 1H), 8.61 (m, 1H), 8.53 (m, 1H), 8.47 (m, 1H), 8.38 (m, 2H), 8.33 (s, 1H), 8.28 (m, 1H), 7.95 (m, 1H), 7.63 (s, 1H), 2.95 (m, 3H); m/z 387.2 (MH$^+$).

Preparation of 6-(benzo[d]thiazol-5-yl)-2-(oxazol-2-yl)-N-(pyridin-3-yl)quinoline-4-carboxamide (53)

The title compound was prepared using the methods shown in Scheme 6 with the appropriate amine in step 2, amide coupling (3-aminopyridine), the appropriate boronic acid in step 3, Suzuki coupling (benzo[d]thiazol-5-ylboronic acid), and the appropriate boronic acid in step 5, Suzuki coupling (oxazol-2-ylboronic acid) to provide the title compound (0.006 g). $^1$H NMR (400 MHz, DMSO-d$_6$) δ ppm 11.22 (s, 1H), 9.50 (s, 1H), 8.99 (s, 1H), 8.63 (m, 1H), 8.56 (m, 1H), 8.50 (m, 2H), 8.42 (m, 2H), 8.36 (m, 2H), 8.31 (m, 1H), 7.96 (m, 1H), 7.64 (s, 1H), 7.48 (m, 1H); m/z 450.2 (MH$^+$).

The following compounds can be made by utilization of the procedures described above:
2-(oxazol-2-yl)-6-((2-(phenylamino)ethyl)amino)-N-(pyridin-3-yl)quinoline-4-carboxamide (54)
N-(4-methoxy-3-(piperidin-1-ylsulfonyl)phenyl)-2-(oxazol-2-yl)-6-((2-(phenylamino)ethyl)amino)quinoline-4-carboxamide (55)
N-methyl-2-(oxazol-2-yl)-6-((2-(phenylamino)ethyl)amino)quinoline-4-carboxamide (56)
6-(benzo[d]thiazol-5-yl)-2-(oxazol-2-yl)-N-(pyridin-3-yl)quinoline-4-carboxamide (57)
6-(benzo[d]thiazol-5-yl)-N-(4-methoxy-3-(piperidin-1-ylsulfonyl)phenyl)-2-(oxazol-2-yl)quinoline-4-carboxamide (58)
N-(4-methoxy-3-(piperidin-1-ylsulfonyl)phenyl)-6-(1-methyl-1H-benzo[d]imidazol-5-yl)-2-(oxazol-2-yl)quinoline-4-carboxamide (59)
N-(4-methoxy-3-(piperidin-1-ylsulfonyl)phenyl)-2-(oxazol-2-yl)-6-phenylquinoline-4-carboxamide (60)
N-(4-methoxy-3-(piperidin-1-ylsulfonyl)phenyl)-2-(oxazol-2-yl)-[6,6'-biquinoline]-4-carboxamide (61)
N-(1H-benzo[d]imidazol-2-yl)-6-(benzo[d]thiazol-5-yl)-2-(oxazol-2-yl)quinoline-4-carboxamide (62)
N-(1H-benzo[d]imidazol-2-yl)-6-(1-methyl-1H-benzo[d]imidazol-5-yl)-2-(oxazol-2-yl)quinoline-4-carboxamide (63)
N-(1H-benzo[d]imidazol-2-yl)-2-(oxazol-2-yl)-6-phenylquinoline-4-carboxamide (64)
N-(1H-benzo[d]imidazol-2-yl)-2-(oxazol-2-yl)-[6,6'-biquinoline]-4-carboxamide (65)
6-(benzo[d]thiazol-5-yl)-N-methyl-2-(oxazol-2-yl)quinoline-4-carboxamide (66).

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Inhibition of Mcl-1 by Compounds of Formula I or Formula II

The expression level of Mcl-1 correlates directly to chemosensitivity and survival of certain non-Hodgkin's lymphomas (Petlickovsk, et al. (2005) Blood 105(12): 4820-7) as well as prostate cancer (Royuela, et al. (2001) Eur. Cytokine Netw. 12(4): 654-63), liver cancer (Fleischer, et al. (2006) Int. J. Oncol. 28(1): 25-32) and other cancers. Mcl-1 is therefore an ideal target for treating these cancers. This example shows that the BH3 mimic compounds of Formula I or Formula II inhibit the binding of the BH3 domain of the Bcl-2 family protein Bim to Mcl-1. Accordingly, this example indicates that compounds of Formula I or Formula II are effective in treating certain hematological malignancies that are affected principally by the Bcl-2 family protein Mcl-1.

Materials and Methods

An ELISA-like streptavidin plate assay was used to demonstrate the activity of the BH3 mimic compounds of Formula I or Formula II to inhibit Mcl-1 to Bim BH3 as described in Wang, et al. (2006) J Med Chem 49: 6139-6142.

Recombinant GST-Mcl-1 fusion protein, used as described below, were generated in *E. coli* and purified using glutathione-sepharose beads using conventional techniques known to those skilled in the fields of biochemistry and molecular biology. (methods for preparation are described in Strategies for Protein Purification and Characterization, Marshak, et al. CSH press, Cold Spring Harbor, N.Y.). Binding of the recombinant proteins to the fluorescent Bim BH3 domain was confirmed by titration of increasing concentrations of the recombinant proteins against a constant amount of labeled Bim peptide (4 nM). Quantitation of binding was accomplished by FP assay with mP measurements made on the Analyst-GT reader (Molecular Devices, Sunnyvale, Calif.).

A streptavidin-coated plate (Thermo Scientific, NUNC #436014) was washed three times with 300 μL of PBS-0.05% Tween solution. A biotinylated twenty-six amino acid peptide, corresponding to the BH3 domain of Bim, with the sequence biotin-(β)A-D-M-R-P-E-I-W-I-A-Q-E-L-R-R-I-G-D-E-F-N-A-Y-Y-A-R-R-amide (SEQ ID No. 14), hereafter referred to as biotin-Bim, was obtained (Tufts). The biotin-Bim peptide was diluted to 0.018 μg/mL (5 nM) in SuperBlock blocking buffer in PBS (Thermo Scientific, #37515), and 100 μL of this solution was incubated in the streptavidin-coated plate for 2.5 hours while shaking. Separately, a compound of Formula I or Formula II, which had been prepared in a 10 mM stock DMSO solution, was then incubated with 20 nM GST-Mcl-1 fusion protein in PBS. Compounds were tested in six three-fold dilutions ranging from 20 μM to 0.6 μM, 10 μM to 0.3 or 5 μM to 0.15 μM. In addition, Bim peptide (New England Peptide) was utilized as a control and tested in six-fold dilutions ranging from 100 nM to 3.3 nM. The streptavidin-coated plate which had previously been treated with biotin-Bim peptide was then washed three times with 300 μL of PBS-0.05% Tween solution. A solution of GST-MCL-1 and a compound of Formula I or Formula II (100 uL) was then added to the streptavidin-coated plate, with two wells utilized as controls (PBS buffer only, no GST-MCL-1 or biotin-Bim) and two wells as an alternative control (containing GST-MCL-1 but no biotin-Bim), and four three-fold dilutions of DMSO (0.2%, 0.06%, 0.02%, and 0.008%). All wells containing compounds of Formula I or Formula II were loaded in duplicate. The plate was incubated for 2 hours at RT, then washed three times with 300 µL of PBS-0.05% Tween solution. Anti-GST HRP (GE Healthcare, #RPN1236) is diluted 1:20,000 in freshly prepared PBS, 0.1% Tween20, and 0.5% BSA was then added to the plate and the plate was incubated for 30 minutes. The plate was then washed five times with 300 µL of PBS-0.05% Tween solution. A solution of color reagents A (stabilized peroxide solution) and B (stabilized chrommogen solution) (R&D Systems, #DY999) is mixed in a 1:1 ratio and added to each well in a quantity of 80 uL. The wells were allowed to develop until control wells containing DMSO are blue (approximately 5-10 minutes). A solution of ELISA stop solution (1M sulfuric acid, 20 uL per well) was then added. Absorbance at 450 nM was read on a Tecan GeniosPro plate reader. Percent inhibition was then calculated as follows: Percent inhibition=1−((Absorbance−Absorbance of PBS-only well)/(Average Absorbance DMSO well−Absorbance of PBS-only well))×100.

In the calculation above, the average absorbance calculated for each compound of Formula I or Formula II (of two wells) was calculated and utilized to calculate the percent inhibition. Percent inhibition was then utilized to calculate IC50 values for each compound of Formula I or Formula II.

Results

Compounds of Formula I or Formula II were effective at inhibiting the Bim-BH3 peptide from Mcl-1 with a drug concentration that provokes a response halfway between baseline and maximum ($IC_{50}$) that ranged from 0.6 µM-20 µM, as shown in FIG. 1A-FIG. 1I.

Example 2

Activity of Compounds of Formula I or Formula II in Killing Human Tumor Cell Lines This example demonstrates the activity of the compounds of Formula I and Formula II and derivatives, in killing certain human tumor-derived cell lines grown in culture. Leukemia and myeloid cells used to assess cell tumor killing activity of the compounds are described. Compounds active in these cell lines have good potential as therapies to treat leukemia and myeloid cancers.

Materials and Methods

Cell Culture

The lymphoid derived cell lines DHL-6, DHL-10 were obtained from Anthony Letai of the Dana Farber Cancer Research Institute, Boston, Mass. The myeloid derived cell line NCI-H929 was obtained from the NIH/NCI cell repository. The mouse leukemia-derived cell line MCL-1-1780 (Ryan et al., Proc. Nat. Acad. Sci USA, 107, 12895-12900) was obtained from Anthony Letai of the Dana Farber Cancer Research Institute, Boston, Mass. Cells were grown in RPMI 1640 medium (GIBCO-BRL) with 2 mM L-glutamine, 4.5 g/L glucose, 1.0 mM sodium pyruvate and 5% fetal bovine serum.

$EC_{50}$ Growth Inhibition Assays

Cells were expanded in tissue culture in appropriate media and then sub-cultured into 96-well plates at a seeding density of 20,000 cells per well. After incubation for 24 hours, cells were treated with compounds that are titrated into appropriate medium with FCS. Cells were treated for 48 hours and scored for viability using the MTS assay (Promega). Growth inhibition was calculated as a percentage of control cell growth. Growth was determined by measuring the $A_{570}$ (control cells)−$A_{570}$ (treated cells)/$A_{570}$ (control cells). $GI_{50}$ values were calculated using Graphpad Prizm software.

Results

The $EC_{50}$ values in the cell lines listed above for compounds of the invention are shown in FIG. 1A-FIG. 1I. In the lymphoid cell line NCI-H929, the $EC_{50}$ values for the compounds of Formula I and Formula II are between 2.3 µM and >25 µM. In the lymphoid cell line DHL6, the $EC_{50}$ values for the compounds of Formula I and Formula II are between 1.8 µM and >25 µM. In the mouse leukemia-derived cell line MCL-1-1780, the $EC_{50}$ values for the compounds of Formula I and Formula II are between 1.0 µM and >25 µM. These data indicate that compounds of this invention are effective at killing tumor cells in culture and are anti-lymphoid and anti-myeloid tumor compounds. Certain compounds of the invention display $EC_{50}$ values of >25 uM in the lymphoid cell line DHL10. The DHL10 cell line is BAX/BAK deficient and therefore will not respond to apoptosis signaling through the BCL-2 pathway. This data indicates that compounds of the invention selectively kill BAX/BAK expressing cell lines over a BAX/BAK deficient cell line, indicating on-target activity of compounds of Formula I and Formula II as MCL-1 inhibitors.

Conclusions

Lymphoid and myeloid cells that have elevated expression of Mcl-1 tend to be resistant to certain chemotherapies. This includes multiple myeloma (MM) (Zhang, et al. (2002), Blood 99:1885-1893), non-Hodgkin's lymphomas (Cho-Vega, et. al (2004) Hum. Pathol. 35(9): 1095-100) and chronic lymphocytic leukemia (CLL) (Michels, et al. (2004), Oncogene 23:4818-4827) cells. As shown in Example 1 above, the compounds of Formula I and Formula II target Mcl-1. This example sets out to show that elevated Mcl-1 would cause hypersensitivity to these compounds under certain conditions. It is more likely that hypersensitivity will occur when the BH3-only protein, Bim, Puma or Noxa are also elevated. Both of these proteins have BH3-mediated binding to Mcl-1. Therefore these cells will be more sensitive to whichever of the BH3 mimic compounds of Formula I or Formula II that have activity in disrupting Bim, Puma or Noxa BH3 mediated binding to Mcl-1.

This, in turn, would qualify these compounds as being most effective in killing tumor cells that have elevated Mcl-1, and those that have elevated Mcl-1 and elevated BH3-only protein Noxa and/or Puma. This finding demonstrates that the BH3 mimic compounds of Formula I and Formula II would be effective at treating chemo-resistant MM, CLL, NHL, AML, and ALL cells that display elevated Mcl-1. This finding also demonstrates that these compounds would be effective as second line therapy in patients treated with proteasome inhibitors such as Bortezomib (Velcade®) who display elevated Mcl-1 with or without elevated Bim, Puma or elevated Noxa.

Example 3

Activity of Mcl-1 Inhibitors in Inducing Cytochrome c Release in an In Situ Mitochondrial Assay The on-target activity of compound II-19 was validated. Changes in mitochondrial integrity were observed utilizing anti-cytochrome c conjugated to Alexa488 (BD). When the mitochondria are intact, they retain cytochrome c and have bright, punctate staining with the antibody whereas cells with compromised mitochondrial integrity will lose cytochrome c and will not stain with the antibody. This can be observed by microscopy as well as measured by a shift in fluorescence on the FL1 channel of a flow cytometer.

The selective response of mitochondria in semi-permeabilized cell lines to the compounds was observed. The assay was adapted from (Campos et al. (2006) Cytometry Part A. 69 (A):515-523).

Materials and Methods

Suspension cell lines SUDHL10 and SUDHL6 were grown in RPMI, washed once in 1×PBS and re-suspended at a concentration of 2e6/ml in assay buffer with 0.0025% Digitonin. Assay buffer; 300 mM Trehalose, 10 mM HEPES-KOH pH 7.7, 80 mM KCl, 1 mM EGTA, 1 mM EDTA, 0.1% BSA, 5 mM Succinate. Cells are incubated with test and control compounds at 106 cells/treatment for 1 hour at room temperature. Samples are fixed with 4% formaldehyde in PBS for 20 minutes, washed once in PBS, and blocked with 2% FBS/0.5% TritonX-100 in PBS. Samples are re-suspended in blocking buffer with 1:250 anti-cytochrome c conjugated to Alexa488 (BD Cat#56028) for 1 hour at 4° C., washed once with blocking buffer and re-suspended in 200 ul PBS. Cytochrome c loss was measured by microscopy. At least 100 cells per treatment were counted and scored as positive for cytochrome c loss if they lacked staining. In both methods DMSO was calculated as 0% cytochrome c loss and the Bim response for DHL6 was used to determine 100% cytochrome c loss.

Results

These data indicate direct activity of compounds 18, 33, 37, and 38 at 20 uM on primed mitochondria, and that the Bax/Bak activity is required for activity (compare activity in Bax/Bak-functional cell line (DHL-6) to lack of activity in Bax/Bak-deficient cell line (DHL-10) (FIG. 2). This is consistent with the activity profile of these compounds in cell studies, and indicates that the compounds exert their biological effect through the mitochondrial apoptosis pathway.

Example 4

Activity of Mcl-1 Inhibitors to Potentiate the Tumor Cell Killing Activity of Proteasome Inhibitors Such as Velcade®

This example is intended to demonstrate the efficacy of compounds of Formula I and Formula II and derivative compounds in potentiating the tumor cell killing activity of Bortezomib (Velcade®).

Proteasome inhibitors such as Bortezomib induce apoptosis and have been recognized as a class of anti-tumor therapeutics (Adams (2004) Cancer Cell 5: 417-421).

The chemical structure of Bortezomib is shown below:

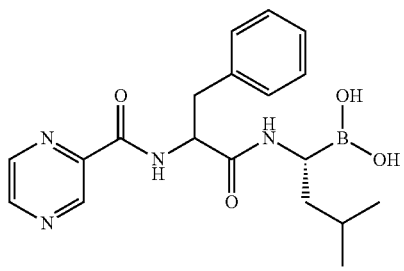 [SMILES: CC(C)C[C@H](NC(=O)C(Cc1ccccc1)NC(=O)c1cnccn1)B(O)O]

Bortezomib (Velcade®) has been approved to treat A-myeloid leukemias and is in phase 3 trials for treatment of solid tumors. Bortezomib is known to dysregulate proteasome-mediated maintenance of Mcl-1 levels in the cell. Accumulated Mcl-1 in Bortezomib-treated cells has been shown to reduce cell killing and promote tumorigenesis, while reduction of Mcl-1 in cells enhances the effectiveness of Bortezomib in inducing apoptosis (Nencioni, et al. (2005) Blood 105: 3255-62). Further, Bortezomib has been shown to cause elevated expression of the BH3-only protein, Noxa (Qin, et al. (2005) Cancer Res. 65(14): 6282-93). The combination of elevated expression of Mcl-1 and Noxa is likely to lead to a cell state previously described as BH3 "sensitization" (Letai, et al. (2002) Cancer Cell. 2(3): 183-92.) and make these cells particularly responsive to Mcl-1 specific inhibition. This example will demonstrate the ability of the compounds of Formula I and Formula II, or derivatives to sensitize tumor cells to Bortezomib or other proteasome-inhibiting drugs as well as taxol and doxarubicen, in particular by inhibiting Mcl-1.

Materials and Methods

The experiments are performed in Jurkat cells or in primary A-myeloid leukemia cells. Cells are treated with Bortezomib alone or in combination with the compounds of Formula I or Formula II or derivatives and $GI_{50}$ values are determined using the MTS assay as described in Example 2.

Jurkat cells are obtained from the American Type Culture Collection (ATCC) Manassas, Va. Primary AML cells are described (Milella, et al. (2002) Blood 99(9): 3461-64) and can be obtained from Dr. Michael Andreeff, M.D. Anderson Cancer Center, Houston, Tex. Mcl-1 rabbit polyclonal anti-Human Mcl-1 IgG is available from Cell Signaling Technologies (Beverly, Mass.). RPMI 1640 medium is available from GIBCO-BRL (Carlsbad, Calif.).

MTS cell viability reagents are available from Promega, (Madison, Wis.). Bortezomib (Velcade®, Millennium Pharmaceutical, Cambridge, Mass.) is available with prescription from any pharmacy.

Cells are planted in 96-well plates at $2 \times 10^4$ cells/well and incubated in 200 µl RPMI with 10% fetal calf serum with antibiotics for 48 hours. Bortezomib is titrated in a 2 fold serial dilution that ranges from 5 to 320 ng/ml (5, 10, 20, 40, 80, 160, 320 ng/ml). Treated cells are allowed to incubate for 48 hours. Treated cells are then assessed for viability using the MTS assay as described in Example 3. The $GI_{50}$ is determined.

Combination treatment of Bortezomib and the compounds of Formula I or Formula II is performed after the $GI_{50}$ of Bortezomib is established. Cells are treated with three concentrations of Bortezomib: the $GI_{50}$ and 2.5 and 5 fold lower concentrations. To these treated cells, the compounds of Formula I or Formula II are added simultaneously in concentrations of 10, 5, 2.5, 1.25, 0.67, 0.34, 0.17, 0.08, 0.04 and 0.02 µM. Combination treated cells and cells treated with either Bortezomib alone or a BH3 mimetic, such as the compounds of Formula I or Formula II, alone are assessed for viability following 24, 48, and 72 hours using the MTS assay as described in Example 2.

Further analysis of cell death is conducted using fluorescence-activated cell sorting (FACS) analysis of annexin V positive staining with the vital dye propidium iodide by standard methods and as described in Wilkins, et al. (2002) Cytometry 48(1): 14-9. Determination of enhanced killing with Bortezomib is correlated with expression levels of Mcl-1 as determined by western blotting of Bortezomib treated and non-treated cells, as well as combinations of treated cell lysates with anti-Mcl-1 antibodies (Cell Signaling Technologies, Beverly, Mass.).

Results

Treatment of cells with the Bortezomib (Velcade®) has been shown to cause elevated Mcl-1 as well as elevated Noxa in lymphoid cells (Perez-Galan, et al. (2005) Blood 107(1): 257-64; Qin, et al. (2005) Cancer Res. 15: 65(14): 6282-93). This combination of elevated Mcl-1 with elevated Noxa leads to the condition described by Letai as "primed" to respond to a Mcl-1 inhibitor. The compound or compounds among the compounds of Formula I and Formula II that best inhibit Mcl-1 will be most effective in synergizing with Bortezomib and increasing its effective range.

Because the chemotherapeutic compounds, taxol and doxorubicin, mediate cell death through the activation of the tumor suppressor p53, and because Noxa is downstream of p53, these treatments will also cause Mcl-1 over-expressing cells to become "primed" for Noxa mediated death when the Mcl-1/Noxa complex is disrupted, as would be the case in treating with a Mcl-1 specific BH3 mimic compound. Therefore one of the compounds of Formula I and Formula II that best inhibit Mcl-1 will be most effective in synergizing with taxol or doxorubicin and increasing the effective range of these compounds in killing tumor cells in vitro. This efficacy will transfer to killing of tumor cell in vivo in animal models for hematological malignancies and to therapeutic value in treating hematological malignancies in humans.

Example 5

Activity of Compounds of Formula I in a Mouse/Human Xenograft Model for Lymphoma In vivo activity of Mcl-1 inhibitor compounds of Formula I or Formula II is assessed in a Human B-cell SCID mouse xenograft tumor model. A dose escalation study is initially performed to determine the maximum tolerated dose that can be safely used for the xenograft study without causing overt toxic side effects. Compound is administered to the mouse i.p. or by oral gavage and at increasing doses from 1 mg/kg to 500 mg/kg and the animals are observed for 24 h for emesis, diarrhea, behavioral abnormalities, or death.

The T Lymphoblastic Leukemic Cell Line CCRF-CEM is purchased from American Type Culture Consortium (ATCC). These cells are maintained in RPMI-1640 medium supplemented with 10% of fetal bovine serum, 2 mM glutamine, and 1 mM sodium pyruvate. The cells are cultured at 37° C. in 95% air/5% $CO_2$ and 100% humidity. Medium in the culture is changed every 48 h and cells are passaged weekly.

For cell implantation to mice, cells are harvested by centrifugation. Cell pellets are resuspended in PBS and counted using a hemacytometer and Trypan Blue dye to measure the number of viable cells in the suspension. The harvested cells are washed once with PBS and resuspended in serum-free medium at a density of $1 \times 10^7$ cells/100 µl.

Study Design

For this xenograft study, animals are divided into 4 groups of 10 mice each. Groups are treated with either test compounds by i.p. injection at the maximum tolerated dose or a vehicle control.

Cell Implantation

Mice are inoculated with the CCRF-CEM cells ($10^7$ cells) by tail vein injection. The cell suspension s have the tendency to form clumps, and are therefore, mixed well prior to drawing into the syringe for cell inoculation. Gauge 28 needles were used for the mouse injection.

Assay Procedure

Test articles are dissolved in an appropriate vehicle and administered to the animals in 100 µl aliquots 5× per week beginning 7 days after cells are transplanted into mice. Throughout the entire study, clinical observations are conducted daily for signs of leukemia development, including lethargy, ruffled fur, lack of responsiveness to stimuli, weight loss, and becoming moribund. On Day 21 after cell inoculation, blood samples are drawn from all groups. The white blood cells of all the blood samples are measured with a Nucleo Counter (ChemMetec, Denmark). The clinical observations are continued until animals either die spontaneously or are sacrificed should they became moribund. Improved survival rates among the treated groups compared to the vehicle control group is indicative of in vivo compound efficacy.

Compound Pharmacokinetics

Pharmacokinetic studies are conducted on compounds of Formula I to assess plasma clearance and distribution in the mouse. Compound is administered i.p. (as in the xenograft study) at 10 mg/kg. Blood plasma samples are obtained at time points of 0, 15 min, 30 min, 60 min, 2 h, 4 h 8 h and 24 h. Compound concentration in the plasma is quantified by LC-MS and the data is fit to standard pharmacokinetic models using WinNonLin software. Compounds of Formula I that exhibited particularly good stability in the mouse (plasma half-lives >2 h) are particularly desirable. These data are then correlated with drug levels obtained in the xenograft model efficacy study and related to the potency required in ex vivo studies in order to demonstrate that drug exposure is sufficient to exert a therapeutic effect.

White Blood Cell Counts in Treated and Untreated Mice

After 14 days of treatment, blood samples are taken from all the mice via orbital bleeding while mice are anesthetized using isoflurane inhalation. Approximately 100 µl of blood is taken from each mouse. The white blood cells are counted. Reductions in white blood cell count are indicative of in vivo compound efficacy.

Example 6

BH3 Profiling with Compounds of Formula I or Formula II Predicts Sensitivity to Mcl-1 Inhibitors and Determines Whether a Cell is Dependent Upon Mcl-1 for Survival As another test of the ability of BH3 profiling to detect in vivo Mcl-1 dependence, the cancer cell line NCI 929 (obtained from ATCC) is examined. Mitochondria are isolated from this cell line and exposed to the panel of BH3 peptides in Table 1 and to compounds of Formula I or Formula II. MOMP is quantitated by JC-1 fluorescence and cytochrome c release is quantitated by ELISA as described in Examples 4 and 5. NCI 929 cells are sensitive to treatment with compounds of Formula I or Formula II in vitro. The mitochondria from these cells demonstrate a sensitivity to Noxa peptide that is diagnostic of Mcl-1 sensitivity while lacking a response to the Bcl-xL reactive peptide Bad. On the other hand, treatment of the mitochondria with compounds of Formula I or Formula II induces MOMP as measured by a decrease in the red JC-1 aggregate fluorescence and as measured by an increase in cytochrome c release. This provides support that compounds of formula identified Formula I or Formula II can substitute for Noxa in the mitochondrial BH3 profiling assay and that the mitochondrial response to these compounds is a powerful predictor of what cells are sensitive to Mcl-1 inhibiting drugs in vitro and in vivo.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

The entire disclosure of each of the patent documents and scientific publications disclosed hereinabove is expressly incorporated herein by reference for all purposes.

What is claimed is:

1. A method for treating chronic myeloid leukemia, pancreatic cancer, hepatocellular carcinoma, esophageal squamous cell carcinoma, melanoma, human non-small cell lung cancer, breast cancer, colon cancer, or rectal cancer, comprising administering an effective amount of a compound of Formula II,

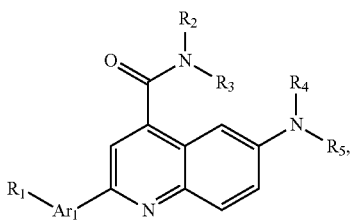

Formula II or a stereoisomer thereof, tautomer thereof, solvate thereof, or a pharmaceutically acceptable salt thereof, to a patient in need thereof,
wherein:
$Ar_1$ is $C_{5-10}$ heteroaryl which is optionally substituted with one or more substituent $R_1$ wherein the substituents may be the same or different;
$R_1$ is independently selected from hydrogen, substituted $C_{1-6}$ alkyl, and unsubstituted $C_{1-6}$ alkyl;
$R_2$ and $R_3$ are each independently selected from hydrogen, substituted or unsubstituted $C_{1-6}$ alkyl, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted $C_{1-10}$ aminoalkyl, substituted or unsubstituted $C_{5-10}$ aryl, and substituted or unsubstituted saturated or unsaturated 3-11 member heteroaryl or heteroarylalkyl containing 1, 2, 3, or 4 heteroatoms selected independently from N, O, S, and $S(O)_2$, or $R_2$ and $R_3$ may be combined with the nitrogen to which they are attached to form a 3, 4, 5, 6, or 7 membered heterocycle in which one or more of the carbons may be substituted with a heteroatom selected from O, N, and S and in which any of the hydrogens of the heterocycle may be substituted with $C_{1-6}$ alkyl, F, Cl, Br, I, cyano, $C_{1-6}$ alkoxy, or $C_{6-10}$ aryloxy; and $R_4$ and $R_5$ are independently selected from hydrogen, substituted or unsubstituted $C_{1-6}$ alkyl, substituted or unsubstituted $C_{1-6}$ aminoalkyl, and substituted or unsubstituted saturated or unsaturated 3-11 member heteroaryl or heteroarylalkyl containing 1, 2, 3, or 4 heteroatoms selected independently from N, O, S, and $S(O)_2$.

2. The method of claim 1, wherein $Ar_1$ is selected from the group consisting of furanyl and oxazolyl.

3. The method of claim 1, wherein $R_1$ is selected from the group consisting of hydrogen and alkyl.

4. The method of claim 1, wherein $R_2$ is selected from the group consisting of hydrogen and alkyl.

5. The method of claim 1, wherein $R_3$ is selected from the group consisting of hydrogen, alkyl, heteroaryl, and substituted aryl.

6. The method of claim 1, wherein $R_4$ is selected from the group consisting of hydrogen and as part of an unsaturated heterocyclic group.

7. The method of claim 1, wherein $R_5$ is selected from the group consisting of heteroaryl, aminoalkyl, and as part of an unsaturated heterocyclic group.

8. The method of claim 1, wherein the compound is selected from the group consisting of 2-(furan-2-yl)-6-(pyridin-2-ylamino)-N-(pyridin-3-yl) quinoline-4-carboxamide (24);

6-((2-(benzyl(methyl)amino)ethyl)amino)-2-(furan-2-yl)-N-(pyridin-3-yl)quinoline-4-carboxamide (25);

2-(furan-2-yl)-6-((2-(phenylamino)ethyl)amino)-N-(pyridin-3-yl)quinoline-4-carboxamide (27);

2-(furan-2-yl)-6-((2-phenoxyethyl)amino)-N-(pyridin-3-yl)quinoline-4-carboxamide (35);

2-(furan-2-yl)-6-(4-phenylpiperazin-1-yl)-N-(pyridin-3-yl)quinoline-4-carboxamide (50);

2-(oxazol-2-yl)-6-((2-(phenylamino)ethyl)amino)-N-(pyridin-3-yl)quinoline-4-carboxamide (54);

N-(4-methoxy-3-(piperidin-1-ylsulfonyl)phenyl)-2-(oxazol-2-yl)-6-((2-(phenylamino)ethyl)amino)quinoline-4-carboxamide (55); and N-methyl-2-(oxazol-2-yl)-6-((2-(phenylamino)ethyl) amino)quinoline-4-carboxamide (56).

9. The method of claim 1, wherein the method is for treating human non-small cell lung cancer or breast cancer.

10. A pharmaceutical composition comprising a compound of Formula I,

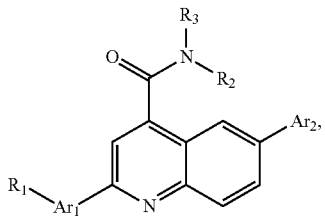

Formula I or a stereoisomer thereof, tautomer thereof, solvate thereof, or a pharmaceutically acceptable salt thereof, and a pharmaceutically acceptable carrier, wherein:
$Ar_1$ is $C_{5-10}$ heteroaryl which is optionally substituted with one or more substituent $R_1$ wherein the substituents may be the same or different;
$Ar_2$ is phenyl substituted with one or more substituent selected from $C_{1-6}$ alkyl, F, Cl, Br, I, cyano, $C_{1-6}$ alkoxy, $C_{6-10}$ aryloxy, and $C_{5-10}$ aryl, wherein the substituents may be the same or different;
$R_1$ is independently selected from hydrogen, substituted $C_{1-6}$ alkyl, and unsubstituted $C_{1-6}$ alkyl; and
$R_2$ and $R_3$ are each independently selected from hydrogen, substituted or unsubstituted $C_{1-6}$ alkyl, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted $C_{1-10}$ aminoalkyl, substituted or unsubstituted $C_{5-10}$ aryl, and substituted or unsubstituted saturated or unsaturated 3-11 member heteroaryl or heteroarylalkyl containing 1, 2, 3, or 4 heteroatoms selected independently from N, O, S, and $S(O)_2$, or $R_2$ and $R_3$ may be combined with the nitrogen to which they are attached to form a 3, 4, 5, 6, or 7 membered heterocycle in which one or more of the carbons may be substituted with a heteroatom selected from O, N, and S and in which any of the hydrogens of the heterocycle may be substituted with $C_{1-6}$ alkyl, F, Cl, Br, I, cyano, $C_{1-6}$ alkoxy, or $C_{6-10}$ aryloxy.

11. The composition of claim 10, wherein $Ar_2$ is selected from the group consisting of halo-substituted phenyl, alkoxy-substituted phenyl, aryl-substituted phenyl, and aryloxy-substituted phenyl.

12. The composition of claim 10, wherein the compound is selected from the group consisting of:
6-(2-fluorophenyl)-2-(furan-2-yl)-N-(pyridin-3-yl)quinoline-4-carboxamide (3);
6-(3-fluorophenyl)-2-(furan-2-yl)-N-(pyridin-3-yl)quinoline-4-carboxamide (4);
6-(4-fluorophenyl)-2-(furan-2-yl)-N-(pyridin-3-yl)quinoline-4-carboxamide (5);
2-(furan-2-yl)-6-(3-methoxyphenyl)-N-(pyridin-3-yl)quinoline-4-carboxamide (6);
2-(furan-2-yl)-6-(4-methoxyphenyl)-N-(pyridin-3-yl)quinoline-4-carboxamide (7);
6-([1,1'-biphenyl]-4-yl)-2-(furan-2-yl)-N-(pyridin-3-yl)quinoline-4-carboxamide (8);
6-([1,1'-biphenyl]-3-yl)-2-(furan-2-yl)-N-(pyridin-3-yl)quinoline-4-carboxamide (9);
2-(furan-2-yl)-6-(3-(2-methoxyethoxy)phenyl)-N-(pyridin-3-yl)quinoline-4-carboxamide (10);
2-(furan-2-yl)-6-(4-(2-methoxyethoxy)phenyl)-N-(pyridin-3-yl)quinoline-4-carboxamide (11);
2-(furan-2-yl)-6-(3-phenoxyphenyl)-N-(pyridin-3-yl)quinoline-4-carboxamide (12); and
2-(furan-2-yl)-6-(4-phenoxyphenyl)-N-(pyridin-3-yl)quinoline-4-carboxamide (13).

13. A method for treating chronic myeloid leukemia, pancreatic cancer, hepatocellular carcinoma, esophageal squamous cell carcinoma, melanoma, human non-small cell lung cancer, breast cancer, colon cancer, or rectal cancer, comprising administering an effective amount of a compound of Formula I,

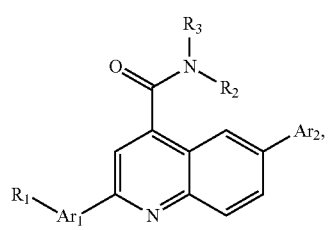

Formula I or a stereoisomer thereof, tautomer thereof, solvate thereof, or a pharmaceutically acceptable salt thereof, wherein:
$Ar_1$ is $C_{5-10}$ heteroaryl which is optionally substituted with one or more substituent $R_1$ wherein the substituents may be the same or different;
$Ar_2$ is phenyl substituted with one or more substituent selected from $C_{1-6}$ alkyl, F, Cl, Br, I, cyano, $C_{1-6}$ alkoxy, $C_{6-10}$ aryloxy, and $C_{5-10}$ aryl, wherein the substituents may be the same or different;
$R_1$ is independently selected from hydrogen, substituted $C_{1-6}$ alkyl, and unsubstituted $C_{1-6}$ alkyl; and
$R_2$ and $R_3$ are each independently selected from hydrogen, substituted or unsubstituted $C_{1-6}$ alkyl, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted $C_{1-10}$ aminoalkyl, substituted or unsubstituted $C_{5-10}$ aryl, and substituted or unsubstituted saturated or unsaturated 3-11 member heteroaryl or heteroarylalkyl containing 1, 2, 3, or 4 heteroatoms selected independently from N, O, S, and $S(O)_2$, or $R_2$ and $R_3$ may be combined with the nitrogen to which they are attached to form a 3, 4, 5, 6, or 7 membered heterocycle in which one or more of the carbons may be substituted with a heteroatom selected from O, N, and S and in which any of the hydrogens of the heterocycle may be substituted with $C_{1-6}$ alkyl, F, Cl, Br, I, cyano, $C_{1-6}$ alkoxy, or $C_{6-10}$ aryloxy.

14. The method of claim 13, wherein $Ar_2$ is selected from the group consisting of halo-substituted phenyl, alkoxy-substituted phenyl, aryl-substituted phenyl, and aryloxy-substituted phenyl.

15. The method of claim of claim 13, wherein the compound is selected from the group consisting of:
6-(2-fluorophenyl)-2-(furan-2-yl)-N-(pyridin-3-yl)quinoline-4-carboxamide (3);
6-(3-fluorophenyl)-2-(furan-2-yl)-N-(pyridin-3-yl)quinoline-4-carboxamide (4);
6-(4-fluorophenyl)-2-(furan-2-yl)-N-(pyridin-3-yl)quinoline-4-carboxamide (5);

2-(furan-2-yl)-6-(3-methoxyphenyl)-N-(pyridin-3-yl)quinoline-4-carboxamide (6);
2-(furan-2-yl)-6-(4-methoxyphenyl)-N-(pyridin-3-yl)quinoline-4-carboxamide (7);
6-([1,1'-biphenyl]-4-yl)-2-(furan-2-yl)-N-(pyridin-3-yl)quinoline-4-carboxamide (8);
6-([1,1'-biphenyl]-3-yl)-2-(furan-2-yl)-N-(pyridin-3-yl)quinoline-4-carboxamide (9);
2-(furan-2-yl)-6-(3-(2-methoxyethoxy)phenyl)-N-(pyridin-3-yl)quinoline-4-carboxamide (10);
2-(furan-2-yl)-6-(4-(2-methoxyethoxy)phenyl)-N-(pyridin-3-yl)quinoline-4-carboxamide (11);
2-(furan-2-yl)-6-(3-phenoxyphenyl)-N-(pyridin-3-yl)quinoline-4-carboxamide (12); and
2-(furan-2-yl)-6-(4-phenoxyphenyl)-N-(pyridin-3-yl)quinoline-4-carboxamide (13).

16. The method of claim 13, wherein the method is for treating human non-small cell lung cancer or breast cancer.

17. A pharmaceutical composition comprising a compound selected from the group consisting of:
2-(furan-2-yl)-6-(naphthalen-2-yl)-N-(pyridin-3-yl)quinoline-4-carboxamide (19);
2-(5-methylfuran-2-yl)-6-phenyl-N-(pyridin-3-yl)quinoline-4-carboxamide (30);
2-(benzofuran-2-yl)-6-phenyl-N-(pyridin-3-yl)quinoline-4-carboxamide (31);
2-(1,3-dimethyl-1H-pyrazol-4-yl)-6-phenyl-N-(pyridin-3-yl)quinoline-4-carboxamide (34);
2-(1-methyl-1H-pyrazol-4-yl)-6-phenyl-N-(pyridin-3-yl)quinoline-4-carboxamide (36);
6-phenyl-N-(pyridin-3-yl)-2-(1-(tetrahydro-2H-pyran-2-yl)-1H-pyrazol-4-yl)quinoline-4-carboxamide (37);
6-phenyl-2-(1H-pyrazol-4-yl)-N-(pyridin-3-yl)quinoline-4-carboxamide (38);
6-phenyl-N-(pyridin-3-yl)-2-(thiazol-2-yl)quinoline-4-carboxamide (41);
2-(oxazol-2-yl)-6-phenyl-N-(pyridin-3-yl)quinoline-4-carboxamide (43);
N-(4-methoxy-3-(piperidin-1-ylsulfonyl)phenyl)-2-(oxazol-2-yl)-6-phenylquinoline-4-carboxamide (60); and
N-(1H-benzo[d]imidazol-2-yl)-2-(oxazol-2-yl)-6-phenylquinoline-4-carboxamide (64);
or a stereoisomer thereof, tautomer thereof, solvate thereof, or a pharmaceutically acceptable salt thereof, and a pharmaceutically acceptable carrier.

18. A method for treating chronic myeloid leukemia, pancreatic cancer, hepatocellular carcinoma, esophageal squamous cell carcinoma, melanoma, human non-small cell lung cancer, breast cancer, colon cancer, or rectal cancer, comprising administering an effective amount of a compound selected from the group consisting of:
2-(furan-2-yl)-6-phenyl-N-(pyridin-3-yl)quinoline-4-carboxamide (1);
2-(furan-2-yl)-6-(naphthalen-2-yl)-N-(pyridin-3-yl)quinoline-4-carboxamide (19);
2-(5-methylfuran-2-yl)-6-phenyl-N-(pyridin-3-yl)quinoline-4-carboxamide (30);
2-(benzofuran-2-yl)-6-phenyl-N-(pyridin-3-yl)quinoline-4-carboxamide (31);
2-(1,3-dimethyl-1H-pyrazol-4-yl)-6-phenyl-N-(pyridin-3-yl)quinoline-4-carboxamide (34);
2-(1-methyl-1H-pyrazol-4-yl)-6-phenyl-N-(pyridin-3-yl)quinoline-4-carboxamide (36);
6-phenyl-N-(pyridin-3-yl)-2-(1-(tetrahydro-2H-pyran-2-yl)-1H-pyrazol-4-yl)quinoline-4-carboxamide (37);
6-phenyl-2-(1H-pyrazol-4-yl)-N-(pyridin-3-yl)quinoline-4-carboxamide (38);
6-phenyl-N-(pyridin-3-yl)-2-(thiazol-2-yl)quinoline-4-carboxamide (41);
2-(oxazol-2-yl)-6-phenyl-N-(pyridin-3-yl)quinoline-4-carboxamide (43);
N-(4-methoxy-3-(piperidin-1-ylsulfonyl)phenyl)-2-(oxazol-2-yl)-6-phenylquinoline-4-carboxamide (60); and
N-(1H-benzo[d]imidazol-2-yl)-2-(oxazol-2-yl)-6-phenylquinoline-4-carboxamide (64);
or a stereoisomer thereof, tautomer thereof, solvate thereof, or a pharmaceutically acceptable salt thereof.

19. The method of claim 18, wherein the method is for treating human non-small cell lung cancer or breast cancer.

* * * * *